United States Patent
Ewing et al.

(10) Patent No.: US 8,710,049 B2
(45) Date of Patent: Apr. 29, 2014

(54) DIAMINOCYCLOHEXANE COMPOUNDS AND USES THEREOF

(75) Inventors: William R. Ewing, Yardley, PA (US); Yeheng Zhu, Stockton, NJ (US); Chongqing Sun, East Windsor, NJ (US); Yanting Huang, Pennington, NJ (US); Maheswaran Sivasamban Karatholuvhu, Periyar Nagar (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/549,717

(22) Filed: Jul. 16, 2012

(65) Prior Publication Data

US 2013/0184262 A1    Jul. 18, 2013

Related U.S. Application Data

(60) Provisional application No. 61/508,842, filed on Jul. 18, 2011.

(51) Int. Cl.
| | |
|---|---|
| *A61K 31/55* | (2006.01) |
| *A61K 31/4418* | (2006.01) |
| *C07D 209/52* | (2006.01) |
| *A61K 31/403* | (2006.01) |
| *C07D 413/10* | (2006.01) |
| *A61K 31/454* | (2006.01) |
| *C07D 401/12* | (2006.01) |
| *C07D 401/04* | (2006.01) |
| *A61K 31/506* | (2006.01) |
| *C07D 207/14* | (2006.01) |
| *A61K 31/402* | (2006.01) |
| *A61K 31/4545* | (2006.01) |
| *C07D 223/12* | (2006.01) |
| *C07D 417/12* | (2006.01) |
| *A61K 45/06* | (2006.01) |
| *C07D 211/56* | (2006.01) |

(52) U.S. Cl.
USPC ...... 514/217.11; 514/239; 514/412; 514/326; 514/323; 514/275; 514/426; 514/318; 546/224; 546/557; 546/209; 546/211; 546/201; 546/194; 548/452; 548/557; 544/323; 540/605

(58) Field of Classification Search
None
See application file for complete search history.

(56) References Cited

FOREIGN PATENT DOCUMENTS

| EP | 2 404 896 | 1/2012 | |
|---|---|---|---|
| WO | WO 2008/052769 | 5/2008 | |
| WO | WO2013052394 A1 * | 11/2013 | ........... C07D 401/00 |

OTHER PUBLICATIONS

International Search Report mailed Sep. 3, 2012.

* cited by examiner

*Primary Examiner* — Jeffrey S. Lundgren
*Assistant Examiner* — Tori M Strong
(74) *Attorney, Agent, or Firm* — Elliott Korsen

(57) ABSTRACT

The present invention provides compounds of Formula (I):

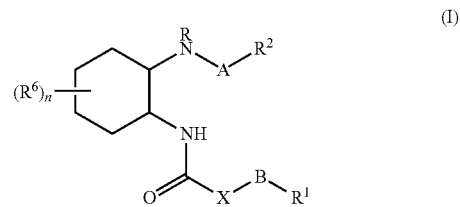

or a stereoisomer, or a pharmaceutically acceptable salt thereof, wherein all of the variables are as defined herein. These compounds are agonists, partial agonists and modulators of the NPY Y4 receptor and may be used for the treatment and prophylaxis of various diseases and conditions.

10 Claims, No Drawings

DIAMINOCYCLOHEXANE COMPOUNDS AND USES THEREOF

FIELD OF THE INVENTION

The present invention provides substituted diaminocyclohexanes, and analogues thereof, which are agonists, partial agonists or modulators of the NPY Y4 receptor, compositions containing the compounds, and methods of using them, for example, for the treatment or prophylaxis of obesity, to control appetite, feeding, food intake, energy expenditure, caloric intake, gastric motility, diabetes and other related conditions.

BACKGROUND OF THE INVENTION

Obesity and its associated disorders are common and very serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia.

Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al., *Br. Med. J.* 301:835-837 (1990)). Obesity is also a risk factor for the group of conditions called insulin resistance syndrome, or "Syndrome X" and metabolic syndrome. The worldwide medical cost of obesity and associated disorders is enormous.

Obesity remains a poorly treatable, chronic, essentially intractable metabolic disorder. Accordingly, a need exists for new therapies useful in weight reduction and/or weight maintenance in a subject. Such therapies would lead to a profound beneficial effect on the subject's health.

The present invention provides methods and compositions useful in the control, treatment, and prevention of obesity and obesity-related conditions, disorders, and diseases, such as those referenced above.

The PP-fold family of peptides, Neuropeptide Y (NPY), Peptide YY (PYY), and Pancreatic Polypeptide ((PP) are naturally secreted homologous, 36 amino acid, C-terminally amidated peptides, which are characterized by a common three-dimensional structure—the PP-fold—which is important for the receptor recognition of the peptides.

NPY is a very wide spread Neuropeptide with multiple actions in various parts of both central and peripheral nervous system acting through a number of different receptor subtypes in man such as Y1, Y2, Y4 and Y5.

PP is a hormone, which is released from endocrine cells in the pancreatic islets, almost exclusively governed by vagal cholinergic stimuli elicited especially by food intake. PP has various effects on the gastrointestinal tract, but none of these are observed in isolated cells and organs, and all appear to be dependent on an intact vagal nerve supply. In accordance with this, the PP receptors, which are called Y4 receptors, are located in the brain stem with a strong expression in vagal motor neurons; the activation of which results in the peripheral effects of PP. Additionally, there is a strong expression in the nucleus tractus solitarirus (NTS), the activation of which results in the effects of PP as a satiety hormone.

It should be noted that PP from the brain has access to this area of the brain since the blood brain barrier is leaky in this area where various hormones from the periphery are sensed. Recently it has been surmised that part of the effect of PP on food intake may be mediated through an action on neurons, especially the POMC/CVART neurons in the arcuate nucleus. PP acts through Y4 receptors for which it has a subnanomolar affinity as opposed to PYY and NPY which have nanomolar affinity for this receptor. PP also has an appreciable affinity for the Y5 receptor, but it is not likely of physiological importance in relation to circulating PP due to both lack of access to the cells in the CNS where this receptor is especially expressed and due to the relatively low affinity for PP.

There are four well established types of PP-fold peptide receptors in man, Y1, Y2, Y4 and Y5, which all recognize NPY1-36 and PYY1-36 with similar affinity. Affinity studies suggest that the Y4 receptors bind PP with a subnanomolar affinity corresponding to the concentrations found in plasma whereas NPY and PYY are recognized with much lower affinity.

PP-fold peptides and analogs of these have been suggested for use in the treatment of obesity and associated diseases, including for example, Prader Willi's syndrome, based on the demonstrated effects of certain of these peptides in animal models ands in man and on the fact that obese people have shown low basal levels of PP and PYY as well as lower meal responses of these peptides. It has also been shown since the mid seventies that PP could affect food intake in rodents. In 1993, it was reported that infusion of PP in morbidly obese patients with Prader Willi's syndrome decreased food intake. Recently this finding was confirmed by infusion of PP in normal human subjects where a long lasting suppression of appetite and reduced food intake over 24 hours was observed.

It was suggested in the seventies that PP might be involved in the control of food intake. Recently, evidence from rodent studies has shown that PP is in fact a powerful and efficient anorexigenic peptide when administered peripherally. Since PP has no effect on appetite, food intake, etc., in Y4 knock out animals, it is very likely that PP acts through the Y4 receptor to reduce appetite and food intake. PP has also been shown to have an effect on food intake in diet induced obese animals. Y4 receptors have been found especially in the brain stem in area postreama and on vagal motor neurons where the blood-brain barrier is not efficient and where circulating hormones such as PP can get access to the neurons. Thus, it is likely that the Y4 receptors in the NTS in the brain stem are a major target through which PP acts to suppress appetite and food intake. However, more recent evidence points to the possibility that PP may also act through Y4 receptors in the arcuate nucleus conceivably on the POMC and perhaps also the NPY/AgRP neurons. Low levels of PP are found in obese subjects especially those with Prader-Willi syndrome. High PP levels are found in patients with anorexia nervosa. Importantly, infusion of PP in man decreases appetite and food intake for up to 24 hours. Thus, the effect of PP on food intake was observed after the PP levels in the circulation had returned to normal levels. Infusion of PP has also been shown to decrease food intake in morbidly obese patients with Prader-Willi syndrome.

For the treatment of conditions responsive to Y4 receptor modulation, such as obesity and intestinal hypersecretion, it would be desirable to use PP-fold peptides or peptide mimics such as small molecules which were specific for the Y4 receptor. In particular, it would be highly desirable to use such agents which are selective for the Y4 receptor over the Y1 receptor. This is particularly important since activation of the Y1 receptor is expected to potentially cause unwanted cardiovascular and renal side effects such as vasoconstriction and natriuresis.

Thus, use of selective and efficacious Y4 receptor agonists over Y1 and Y2 receptor agonists would be particularly useful in diseases and conditions susceptible to Y4 receptor activation.

The present invention relates to novel substituted diaminocyclohexane compounds which have the ability to activate, partially activate and/or modulate the NPY Y4 receptor. Such compounds are therefore potentially useful for the treatment or prophylaxis of obesity, to control appetite, feeding, food intake, energy expenditure, caloric intake, gastric motility, diabetes and other related conditions.

SUMMARY OF THE INVENTION

The present invention provides substituted diaminocyclohexanes compounds, and analogues thereof, which are useful as agonists, partial agonists or modulators of the NPY Y4 receptor, including stereoisomers, tautomers, pharmaceutically acceptable salts, or solvates thereof.

The present invention also provides pharmaceutical compositions comprising a pharmaceutically acceptable carrier and one or more of the compounds of the present invention or stereoisomers, tautomers, pharmaceutically acceptable salts, or solvates thereof.

The compounds of the invention may be used in the treatment and/or prophylaxis of multiple diseases or disorders associated with the NPY Y4 receptor, such as obesity, appetite control, feeding behavior, food intake, energy expenditure, caloric intake, gastric motility, Metabolic Syndrome and its component conditions, disorders of glucose metabolism, diabetes and related conditions, microvascular complications associated with diabetes, the macrovascular complications associated with diabetes, cardiovascular diseases and other maladies.

The compounds of the invention may be used in therapy.

The compounds of the invention may be used for the manufacture of a medicament for the treatment and/or prophylaxis of multiple diseases or disorders associated with the NPY Y4 receptor.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides, a compound of Formula (I):

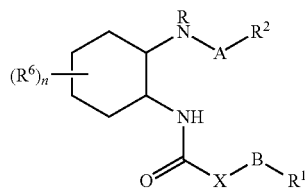

(I)

wherein
A is a nitrogen containing 5- to 8-membered heterocyclyl or an azabicycloalkyl, each optionally substituted with $(C_1\text{-}C_6)$alkyl, —OH or halogen;
X is $CH_2$, O, or NH;
B is absent or is —$(CH_2)_m$—;
R is H or $(C_1\text{-}C_6)$alkyl;
$R^1$ is $(C_6)$aryl or 5- to 8-membered cycloalkyl or 5- to 8-membered heteroaryl, said heteroaryl containing 1-4 heteroatoms selected from N, O, and S, wherein the cycloalkyl, aryl and heteroaryl may be optionally substituted with one or more $R^3$;
$R^2$ is $(C_6)$aryl or 5- to 8-membered heteroaryl, said heteroaryl containing 1-4 heteroatoms selected from N, O, and S, wherein both the aryl and heteroaryl may be optionally substituted with one or more $R^4$, wherein $R^2$ is connected to ring A through the nitrogen atom;
$R^3$ is independently one or more halogen, —OH, —CN, —$NO_2$, —COOH, —$CO_2(C_1\text{-}C_6)$alkyl, —$CF_3$, —$OCHF_2$, —$OCF_3$, —$(C_1\text{-}C_6)$-alkyl, —$(C_1\text{-}C_6)$-alkyloxy, —$CONR^9R^{10}$, —$O(C=O)NR^9R^{10}$, —$NR^9R^{10}$, —$(C_1\text{-}C_6)$-alkylCOOH, —$(C_1\text{-}C_6)$-alkyl-$CO_2(C_1\text{-}C_6)$-alkyl, —$(C_1\text{-}C_6)$-alkylOH, —$(C_1\text{-}C_6)$-alkylCONR$^9$R$^{10}$, —$(C_{6\text{-}10})$aryl, a 5- to 8-membered heteroaryl, which contains 1-4 heteroatoms selected from N, O, and S; and a 5- to 10-membered heterocyclyl, which contains 1-4 heteroatoms selected from N, O, and S; wherein any alkyl, aryl, heteroaryl, and heterocyclyl may be optionally substituted with one or more substituents selected from the group consisting of: halo, —OH, cyano, nitro, —$CF_3$, —$OCF_3$, —$OCF_2$, $(C_1\text{-}C_6)$-alkyl, $(C_2\text{-}C_6)$-alkynyl, $(C_1\text{-}C_6)$-alkyloxy, —COOH, —$CO_2(C_1\text{-}C_6)$-alkyl, —$CONR^9R^{10}$, —$NR^9R^{10}$, —$O(C=O)$—$(C_1\text{-}C_6)$-alkyl, —$O(C=O)NR^9R^{10}$; —$(C_1\text{-}C_6)$-alkylCOOH, —$(C_1\text{-}C_6)$-alkylOH, —$(C_1\text{-}C_6)$-alkylCONR$^9$R$^{10}$, —$(C_1\text{-}C_6)$-alkyl-$CO_2(C_1\text{-}C_6)$-alkyl, $(C_{6\text{-}10})$aryl, a 5- to 8-membered heteroaryl, which contains 1-4 heteroatoms selected from N, O, and S, a 5- to 10-membered heterocyclyl, which contains 1-4 heteroatoms selected from N, O, and S;
or $R^3$ and another $R^3$ can optionally be taken together with the carbon atom that they are attached to form a —$(C_4\text{-}C_8)$cycloalkyl, —$(C_6)$aryl, a 5- to 8-membered heterocyclyl, which contains 1-4 heteroatoms selected from N, O, and S, or a 5- to 8-membered heteroaryl ring, which contains 1-4 heteroatoms selected from N, O, and S, that may be optionally substituted with one or more substituents selected from the group consisting of: halo, —OH, cyano, nitro, —$CF_3$, —$OCF_3$, —$OCF_2$, $(C_1\text{-}C_6)$-alkyl, $(C_2\text{-}C_6)$-alkenyl, $(C_2\text{-}C_6)$-alkynyl, $(C_1\text{-}C_6)$-alkyloxy, —COOH, —$CO_2(C_1\text{-}C_6)$-alkyl, —$CONR^9R^{10}$, —$NR^9R^{10}$, —$O(C=O)$—$(C_1\text{-}C_6)$-alkyl, —$O(C=O)NR^9R^{10}$; —$(C_1\text{-}C_6)$-alkylCOOH, —$(C_1\text{-}C_6)$-alkylOH, —$(C_1\text{-}C_6)$-alkylCONR$^9$R$^{10}$, —$(C_1\text{-}C_6)$-alkyl-$CO_2(C_1\text{-}C_6)$-alkyl, $(C_{6\text{-}10})$aryl, a 5- to 8-membered heteroaryl, which contains 1-4 heteroatoms selected from N, O, and S, a 5- to 10-membered heterocyclo, which contains 1-4 heteroatoms selected from N, O, and S; halo$(C_1\text{-}C_6)$alkyl, and halo$(C_1\text{-}C_6)$alkyloxy;
$R^4$ is halogen, —OH, $CF_3$, —$OCF_2$, —$OCF_3$, —CN, —$NO_2$, —COOH, $(C_1\text{-}C_6)$-alkyl, $(C_1\text{-}C_6)$-alkyloxy, —$CO(C_1\text{-}C_6)$-alkyl, —$CO_2(C_1\text{-}C_6)$-alkyl, —$CONR^9R^{10}$, —$NR^9R^{10}$, or a 5- to 10-membered heteroaryl containing 1-4 heteroatoms selected from N, O, and S, optionally substituted with one or more $R^5$;
$R^5$ is halogen, —OH, —$CF_3$, —$OCF_2$, —$OCF_3$, —CN, —$NO_2$, —$(C_1\text{-}C_6)$alkyl, or —$(C_1\text{-}C_6)$alkyloxy;
$R^6$ is halogen, —OH, $(C_1\text{-}C_6)$-alkyl or $(C_3\text{-}C_6)$-cycloalkyl;

$R^9$ and $R^{10}$, at each occurrence, are independently hydrogen or $(C_1-C_8)$-alkyl, wherein the alkyl may be optionally substituted with one or more $R^{11}$'s;

or $R^9$ and $R^{10}$ are taken together with the nitrogen to which both are attached to form a 3- to 8-membered ring, which may optionally contain 1-4 heteroatoms selected from N, O, and S and be optionally substituted with one or more $R^{11}$'s;

$R^{11}$ is halo, —OH, cyano, $(C_1-C_6)$-alkyl;

m is 1, 2, to 3;

n is 1, 2 or 3;

or a stereoisomer, tautomer, or pharmaceutically acceptable salt thereof.

In a second aspect, the invention is directed to a compound of formula Ia

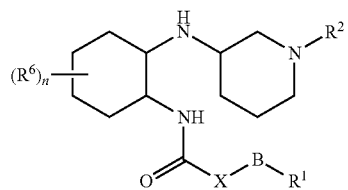

(Ia)

or a stereoisomer, tautomer, or pharmaceutically acceptable salt thereof.

In a third aspect, the invention is directed to a compound of formula Ia wherein:

$R^2$ is $(C_6)$aryl or 5- to 6-membered heteroaryl, said heteroaryl containing 1-4 heteroatoms selected from N, and O, wherein both the aryl and heteroaryl may be optionally substituted with one or more $R^4$;

$R^4$ is fluoro, chloro, $CF_3$, —$OCF_2$, —$OCF_3$, —CN, —$NO_2$, or a 5- to 6-membered heteroaryl containing 1-4 heteroatoms selected from N, O, and S, optionally substituted with one or more $R^5$;

$R^5$ is halogen, —OH, —$CF_3$, —$OCF_2$, —$OCF_3$, —CN, —$(C_1-C_6)$alkyl, or —$(C_1-C_6)$alkyloxy;

or a stereoisomer, tautomer, or pharmaceutically acceptable salt thereof.

In a fourth aspect, the invention is directed to a compound of formula Ia wherein:

$R^1$ is $(C_6)$aryl or 5- to 6-membered heteroaryl, said heteroaryl containing 1-4 heteroatoms selected from N, O, and S, wherein aryl and heteroaryl may be optionally substituted with one or more $R^3$;

$R^3$ is independently chosen from halogen, —OH, —CN, —$CF_3$, —$OCHF_2$, —$OCF_3$, —$(C_1-C_6)$alkyl, —$(C_1-C_6)$-alkyloxy, —$CONR^9R^{10}$, —$O(C=O)NR^9R^{10}$, —$(C_1-C_6)$-alkylCONR$^9$R$^{10}$, —$(C_6-C_{10})$aryl, a 5- to 6-membered heteroaryl, which contains 1-4 heteroatoms selected from N, O, and S; and a 5- to 7-membered heterocyclyl, which contains 1-4 heteroatoms selected from N, O, and S; wherein any alkyl, aryl, heteroaryl, and heterocyclyl may be optionally substituted with one or more substituents selected from the group consisting of halo, —OH, cyano, —$CF_3$, —$OCF_3$, —$OCF_2$, $(C_1-C_6)$-alkyl, $(C_1-C_6)$-alkyloxy, —$CONR^9R^{10}$ and —$O(C=O)NR^9R^{10}$;

or a stereoisomer, tautomer, or pharmaceutically acceptable salt thereof.

In another aspect, the invention is directed to a compound of formula Ia wherein:

$R^2$ is phenyl, pyridyl, pyrimidinyl, pyridazinyl, or pyrazinyl, substituted with one or more $R^4$;

$R^4$ is fluoro, chloro, $CF_3$, —$OCF_2$, —$OCF_3$, —CN or —$NO_2$; or a stereoisomer, tautomer, or pharmaceutically acceptable salt thereof.

In another aspect, the invention is directed to a compound of formula Ia wherein:

$R^2$ is phenyl, pyridyl, pyrimidinyl, pyridazinyl, or pyrazinyl, substituted with one or more $R^4$;

$R^4$ is tetrazole, oxadiazole, oxazole, pyrazole or isoxazole, optionally substituted with one or more $R^5$;

$R^5$ is halogen, —OH, —$CF_3$, —$OCF_2$, —$OCF_3$, —CN, methyl, ethyl, cyclopropyl, methoxy, ethoxy or cyclopropyloxy;

or a stereoisomer, tautomer, or pharmaceutically acceptable salt thereof.

In another aspect, the invention is directed to a compound of formula Ib

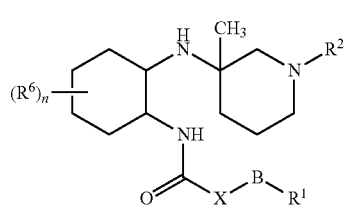

(Ib)

or a stereoisomer, tautomer, or pharmaceutically acceptable salt thereof.

In another aspect, the invention is directed to a compound of formula Ib wherein:

$R^2$ is $(C_6)$aryl or 5- to 6-membered heteroaryl, said heteroaryl containing 1-4 heteroatoms selected from N, and O, wherein both the aryl and heteroaryl may be optionally substituted with one or more $R^4$;

$R^4$ is fluoro, chloro, $CF_3$, —$OCF_2$, —$OCF_3$, —CN, —$NO_2$, or a 5- to 6-membered heteroaryl containing 1-4 heteroatoms selected from N, O, and S, optionally substituted with one or more $R^5$;

$R^5$ is halogen, —OH, —$CF_3$, —$OCF_2$, —$OCF_3$, —CN, —$(C_1-C_6)$alkyl, or —$(C_1-C_6)$alkyloxy;

or a stereoisomer, tautomer, or pharmaceutically acceptable salt thereof.

In another aspect, the invention is directed to a compound of formula Ib wherein:

$R^1$ is $(C_6)$aryl or 5- to 6-membered heteroaryl, said heteroaryl containing 1-4 heteroatoms selected from N, O, and S, wherein aryl and heteroaryl may be optionally substituted with one or more $R^3$;

$R^3$ is independently chosen from halogen, —OH, —CN, —$CF_3$, —$OCHF_2$, —$OCF_3$, —$(C_1-C_6)$alkyl, —$(C_1-C_6)$-alkyloxy, —$CONR^9R^{10}$, —$O(C=O)NR^9R^{10}$, —$(C_1-C_6)$-alkylCONR$^9$R$^{10}$, —$(C_6-C_{10})$aryl, a 5- to 6-membered heteroaryl, which contains 1-4 heteroatoms selected from N, O, and S; and a 5- to 7-membered heterocyclyl, which contains 1-4 heteroatoms selected from N, O, and S; wherein any alkyl, aryl, heteroaryl, and heterocyclyl may be optionally substituted with one or more substituents selected from the group consisting of halo, —OH, cyano, —$CF_3$, —$OCF_3$, —$OCF_2$, $(C_1-C_6)$-alkyl, $(C_1-C_6)$-alkyloxy, —$CONR^9R^{10}$ and —$O(C=O)NR^9R^{10}$;

or a stereoisomer, tautomer, or pharmaceutically acceptable salt thereof.

In another aspect, the invention is directed to a compound of formula Ib wherein:
$R^2$ is phenyl, pyridyl, pyrimidinyl, pyridazinyl, or pyrazinyl, substituted with one or more $R^4$;
$R^4$ is fluoro, chloro, $CF_3$, $-OCF_2$, $-OCF_3$, $-CN$ or $-NO_2$;
or a stereoisomer, tautomer, or pharmaceutically acceptable salt thereof.

In another aspect, the invention is directed to a compound of formula Ib wherein:
$R^2$ is phenyl, pyridyl, pyrimidinyl, pyridazinyl, or pyrazinyl, substituted with one or more $R^4$;
$R^4$ is tetrazole, oxadiazole, oxazole, pyrazole or isoxazole, optionally substituted with one or more $R^5$;
$R^5$ is halogen, $-OH$, $-CF_3$, $-OCF_2$, $-OCF_3$, $-CN$, methyl, ethyl, cyclopropyl, methoxy, ethoxy or cyclopropyloxy;
or a stereoisomer, tautomer, or pharmaceutically acceptable salt thereof.

In another aspect, the invention is directed to a compound of formula Ic

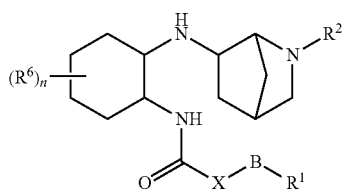

(Ic)

or a stereoisomer, tautomer, or pharmaceutically acceptable salt thereof.

In another aspect, the invention is directed to a compound of formula Ic wherein:
$R^2$ is $(C_6)$aryl or 5- to 6-membered heteroaryl, said heteroaryl containing 1-4 heteroatoms selected from N, and O, wherein both the aryl and heteroaryl may be optionally substituted with one or more $R^4$;
$R^4$ is fluoro, chloro, $CF_3$, $-OCF_2$, $-OCF_3$, $-CN$, $-NO_2$, or a 5- to 6-membered heteroaryl containing 1-4 heteroatoms selected from N, O, and S, optionally substituted with one or more $R^5$;
$R^5$ is halogen, $-OH$, $-CF_3$, $-OCF_2$, $-OCF_3$, $-CN$, $-(C_1-C_6)$alkyl or $-(C_1-C_6)$alkyloxy;
or a stereoisomer, tautomer, or pharmaceutically acceptable salt thereof.

In another aspect, the invention is directed to a compound of formula Ic wherein:
$R^1$ is $(C_6)$aryl or 5- to 6-membered heteroaryl, said heteroaryl containing 1-4 heteroatoms selected from N, O, and S, wherein aryl and heteroaryl may be optionally substituted with one or more $R^3$;
$R^3$ is independently chosen from halogen, $-OH$, $-CN$, $-CF_3$, $-OCHF_2$, $-OCF_3$, $-(C_1-C_6)$alkyl, $-(C_1-C_6)$-alkyloxy, $-CONR^9R^{10}$, $-O(C=O)NR^9R^{10}$, $-(C_1-C_6)$-alkylCONR$^9R^{10}$, $-(C_6-C_{10})$aryl, a 5- to 6-membered heteroaryl, which contains 1-4 heteroatoms selected from N, O, and S; and a 5- to 7-membered heterocyclyl, which contains 1-4 heteroatoms selected from N, O, and S; wherein any alkyl, aryl, heteroaryl, and heterocyclyl may be optionally substituted with one or more substituents selected from the group consisting of halo, $-OH$, cyano, $-CF_3$, $-OCF_3$, $-OCF_2$, $-(C_1-C_6)$-alkyl, $-(C_1-C_6)$-alkyloxy, $-CONR^9R^{10}$ and $-O(C=O)NR^9R^{10}$;

or a stereoisomer, tautomer, or pharmaceutically acceptable salt thereof.

In another aspect, the invention is directed to a compound of formula Ic wherein:
$R^2$ is phenyl, pyridyl, pyrimidinyl, pyridazinyl, or pyriazinyl, substituted with one or more $R^4$;
$R^4$ is fluoro, chloro, $CF_3$, $-OCF_2$, $-OCF_3$, $-CN$ or $-NO_2$;
or a stereoisomer, tautomer, or pharmaceutically acceptable salt thereof.

In another aspect, the invention is directed to a compound of formula Ic wherein:
$R^2$ is phenyl, pyridyl, pyrimidinyl, pyridazinyl, or pyrazinyl, substituted with one or more $R^4$;
$R^4$ is tetrazole, oxadiazole, oxazole, pyrazole or isoxazole, optionally substituted with one or more $R^5$;
$R^5$ is halogen, $-OH$, $-CF_3$, $-OCF_2$, $-OCF_3$, $-CN$, methyl, ethyl, cyclopropyl, methoxy, ethoxy or cyclopropyloxy;
or a stereoisomer, tautomer, or pharmaceutically acceptable salt thereof.

In another aspect, the invention provides a compound selected from those exemplified or a stereoisomer, tautomer, or pharmaceutically acceptable salt thereof.

II. OTHER EMBODIMENTS OF THE INVENTION

In another embodiment, the present invention provides a composition comprising one or more of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and one or more of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of one or more of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention methods provides a pharmaceutical composition for treating diabetes, especially Type II diabetes, which includes the step of administering a therapeutically effective amount of at least one compound according to Formula I alone or in combination with one or more additional anti-diabetic agents to a patient in need of such treatment, wherein the anti-diabetic agent is described herein.

In another embodiment, the present invention provides a pharmaceutical composition further comprising additional therapeutic agent(s). In a preferred embodiment, the present invention provides pharmaceutical composition, wherein the additional therapeutic agent is, for example, a dipeptidyl peptidase-IV (DPP4) inhibitor (for example, an agent selected from saxagliptin, sitagliptin, vildagliptin and alogliptin).

In another embodiment, the present invention provides a pharmaceutical composition further comprising additional therapeutic agent(s). In a preferred embodiment, the present invention provides pharmaceutical composition, wherein the additional therapeutic agent is, for example, a sodium glucose transport (SGLT) inhibitor (for example, dapagliflozin).

In another embodiment, the present invention provides a method for the treatment and/or prophylaxis of multiple diseases or disorders that have been associated to be treated through the modulation of the NPY Y4 receptor comprising administering to a patient in need of such treatment and/or prophylaxis a therapeutically effective amount of one or more of the compounds of the present invention, alone, or, optionally, in combination with another compound of the present invention and/or one or more other type of therapeutic agent.

Examples of diseases or disorders that have been associated to be treated through the modulation of the NPY Y4 receptor according to the present invention include, but are not limited to, gastric motility, obesity and being overweight and conditions in which obesity and being overweight are considered contributory factors. These include bulimia, bulimia nervosa, Syndrome X (Metabolic Syndrome), diabetes, type 2 diabetes mellitus or Non Insulin Dependent Diabetes Mellitus (NIDDM), hyperglycemia, impaired glucose tolerance, insulin resistance, cardiovascular disease, hypertension, atherosclerosis, coronary artery disease, myocardial infarction, peripheral vascular disease, stroke, thromboembolic diseases, hyperlipidemia, hypercholesterolemia, gall bladder disease, osteoarthritis, sleep apnea, reproductive disorders such as polycystic ovarian syndrome, or cancer of the breast, prostate or colon.

In another embodiment, the present invention provides a method for the treatment and/or prophylaxis of obesity, appetite control, food intake, energy expenditure, caloric intake, diabetes, hyperglycemia, gestational diabetes, dyslipidemia, hypertension and cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent. Preferably, the second therapeutic agent is an anti-obesity, or an anti-diabetic agent.

In another embodiment, the invention provides a method for decreasing motility of the upper GI tract, e.g., decreasing gastric emptying.

In another embodiment, the present invention provides a compound of the present invention for use in therapy.

In another embodiment, the present invention provides a compound of the present invention for use in therapy for the treatment and/or prophylaxis of multiple diseases or disorders that have been associated to be treated through the modulation of the NPY Y4 receptor.

In another embodiment, the present invention also provides the use of a compound of the present invention for the manufacture of a medicament for the treatment and/or prophylaxis of multiple diseases or disorders that have been associated to be treated through the modulation of the NPY Y4 receptor.

In another embodiment, the present invention provides a method for the treatment and/or prophylaxis of multiple diseases or disorders that have been associated to be treated through the modulation of the NPY Y4 receptor, comprising: administering to a patient in need thereof a therapeutically effective amount of a first and second therapeutic agent, wherein the first therapeutic agent is a compound of the present invention. Preferably, the second therapeutic agent is, for example, dipeptidyl peptidase-IV (DPP4) inhibitor (for example, an agent selected from saxagliptin, sitagliptin, vildagliptin and alogliptin).

In another embodiment, the present invention provides a method for the treatment and/or prophylaxis of multiple diseases or disorders that have been associated to be treated through the modulation of the NPY Y4 receptor, comprising: administering to a patient in need thereof a therapeutically effective amount of a first and second therapeutic agent, wherein the first therapeutic agent is a compound of the present invention. Preferably, the second therapeutic agent is, for example, a sodium glucose transport (SGLT) inhibitor (for example, dapagliflozin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders that have been associated to be treated through the modulation of the NPY Y4 receptor.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

DEFINITIONS

The following are definitions of terms that may be used in the present specification. The initial definition provided for a group or term herein applies to that group or term throughout the present specification individually or as part of another group, unless otherwise indicated.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of $C=C$ double bonds, $C=N$ double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" refers to straight or branched chain unsubstituted hydrocarbon groups of 1 to 20 carbon atoms, preferably 1 to 6 carbon atoms. The expression "lower alkyl" refers to unsubstituted alkyl groups of 1 to 4 carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g., $SO_2NH_2$, substituted sulfonamido, nitro, cyano, carboxy, carbamyl, e.g., $CONH_2$, substituted carbamyl e.g., CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and terahydronaphthyl. The fused aryls may be connected to another group either at a suitable position on the cycloalkyl ring or the aromatic ring. For example:

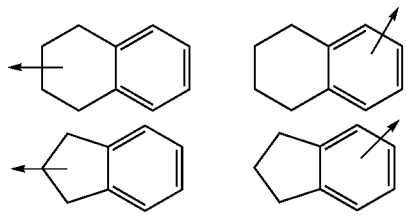

Arrowed lines drawn from the ring system indicate that the bond may be attached to any of the suitable ring atoms.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g., imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cyclooctyl, cyclodecyl, cyclododecyl, bicycloheptane, bicyclooctane and adamantyl. Exemplary substituents include one or more alkyl groups as described above, or one or more groups described above as alkyl substituents.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocyclo", "heterocyclyl" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl. Examples of heterocycles include, but are not limited to, azetidinyl, pyrrolinyl, piperidinyl, piperazinyl, tetrahydrofuranyl, morpholinyl, dihydropyrrazolyl, dihydro-isoxazolyl. Also included are fused ring and spiro compounds containing, for example, the above heterocycles.

As used herein, the term "heteroaryl", is intended to mean a stable, 5-, 6-, or 7-membered monocyclic or bicyclic or 7-, 8-, 9-, 10-, 11-, 12-, 13-, or 14-membered polycyclic heteroaryl ring that is fully unsaturated, and that contains carbon atoms and 1, 2, 3 or 4 heteroatoms independently selected from the group consisting of N, O and S; and including any polycyclic group in which any of the above-defined heteroaryl rings is fused to a benzene ring or a heterocyclyl ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heteroaryl ring may be attached to its pendant group at any heteroatom or carbon atom that results in a stable structure. The heteroaryl rings described herein may be substituted on carbon or on a nitrogen atom if the resulting compound is stable. A nitrogen in the heteroaryl may optionally be quaternized. Examples of heteroaryls include, but are not limited to, pyridinyl, pyrimidinyl, pyrazinyl, pyridazinyl, furanyl, thienyl, pyrrolyl, pyrazolyl, imidazolyl, indolyl, tetrazolyl, isoxazolyl, oxazolyl, oxadiazolyl, thiadiazolyl, thiazolyl, benzimidazolyl, 1H-indazolyl, benzofuranyl, benzothiofuranyl, benztetrazolyl, benzotriazolyl, benzisoxazolyl, benzoxazolyl, isoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzene ring, each fused to a second ring. The second ring is a 5- or 6-membered monocyclic ring which is saturated, partially unsaturated, or unsaturated, and comprises a 5-membered heterocycle; a 6-membered heterocycle or a carbocycle (provided the first ring is not benzene when the second ring is a carbocycle). The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of bicyclic heterocyclic groups are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "azabicycloalkyl" is intended to mean a stable bicyclic hydrocarbon that includes one nitrogen and optionally another heteroatom chosen from the group of N, O, S. The two fused rings are connected at non adjacent atoms.

Examples of azabicycloalkyl groups are, but not limited to, 2-azabicyclo[2.2.1]heptane, 2-azabicyclo[2.2.2]octane, 2-azabicyclo[3.1.1]heptane, 6-azabicyclo[3.1.1]heptane, 8-azabicyclo[3.2.1]octane, 6-azabicyclo[3.2.1]octane, 1,4-diazabicyclo[3.2.1]octane, 6-azabicyclo[3.2.2]nonane.

The term "heteroatoms" shall include oxygen, sulfur and nitrogen.

The term "alkylsulfone" refers to —$R^kS(=O)_2R^k$, wherein $R^k$ is an alkyl or substituted alkyl.

The term "oxo" refers to the divalent radical =O.

The term "carbamate" refers to the group —$OC(=O)NH_2$.

The term "amide" refers to the group —$C(=O)NH_2$.

The term "sulfonamide" refers to the group —$SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —$C(=O)NR'''R''$ wherein $R'''$ and $R''$ are independently selected from H, alkyl, substituted alkyl, alkenyl, substituted alkenyl, cycloalkyl, and substituted cycloalkyl, provided at least one of $R'''$ or $R''$ is a substituted moiety.

A substituted sulfonamide, for example, refers to the group —$SO_2NR^oR^p$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group —$OC(=O)NR^qR^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group —$NHC(=O)NH_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —$N(O)_2$.

The term "thio" refers to the group —SH.

The term "alkylthio" refers to the group —$SR^s$ where $R^s$ is an alkyl, substituted alkyl, cycloalkyl, or substituted cycloalkyl.

The term "thioalkyl" refers to the group —$R^tS$ where $R^t$ is an alkyl, substituted alkyl, cycloalkyl, or substituted cycloalkyl.

The term "alkylsulfonyl" refers to the group —$S(=O)_2R^u$ where $R^u$ is an alkyl, substituted alkyl, cycloalkyl, or substituted cycloalkyl.

The term "alkylsulfinyl" refers to the group —$S(=O)R^v$ where $R^v$ is an alkyl, substituted alkyl, cycloalkyl, or substituted cycloalkyl.

The term "carboxy" refers to the group —$C(=O)OH$.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —$C(=O)OR^w$ where $R^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —$OC(=O)R^x$, where $R^x$ is an alkyl or substituted alkyl, or an aryl or substituted aryl, respectively.

The term "carbamoyl" refers to the groups —$OC(=O)NH_2$, —$OC(=O)NHR^x$, and/or —$OC(=O)NR^yR^z$, wherein $R^y$ and $R^z$ are independently selected from alkyl and substituted alkyl.

The term "carbonyl" refers to a $C(=O)$.

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group $S(=O)_2$.

The term "sulfinyl" refers to an $S(=O)$.

The term "carboxyalkyl" refers to an alkyl or substituted alkyl bonded to a carboxy.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:
a) *Design of Prodrugs*, Bundgaard, H., ed., Elsevier (1985), and *Methods in Enzymology*, 112:309-396, Widder, K. et al., eds., Academic Press (1985);
b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

The term "modulator" refers to a compound that acts at the NPY Y4 receptor to alter its ability to regulate downstream signaling events. Examples of receptor modulators include agonists, antagonists, partial agonists, inverse agonists, allosteric antagonists and allosteric potentiators as defined in standard pharmacology textbooks (e.g., Ross, E. M. et al., *Goodman and Gilman's The Pharmacological Basis of Therapeutics*, 10th Edition, Chapter 2, pp. 31-43, McGraw Hill (2001)).

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition, Mack Publishing Company, Easton, Pa. (1985), which is incorporated herein by reference in its entirety.

Utility

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, impaired glucose hemostasis, insulin resistance, hypercholesterolemia, hypertriglyceridemia, choletithiasis, dislipidemic conditions, bulimia nervosa and compulsive eating disorders); gastrointestinal disorders and inflammatory diseases such as inflammatory bowel disease, colitis and/or Crohn's disease.

Dosage Forms

The compounds of the present invention can be administered in oral dosage form. The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

Pharmaceutical Combinations

The present invention includes within its scope pharmaceutical compositions comprising a therapeutically effective amount of at least one of the compounds of Formula I, together with a pharmaceutically acceptable carrier or diluent. Compounds of the present invention can be used alone or in pharmaceutical combinations comprising other suitable therapeutic agents useful in the treatment of the aforementioned disorders including anti-obesity agents, anti-diabetic agents, appetite suppressants, lipid-lowering agents, HDL-raising agents, cognition enhancing agents, agents used to treat neurodegeneration, agents used to treat bowel disorders, anti-inflammatory agents, anti-anxiety agents, and anti-depressants.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the NPY Y4 receptor agonist in accordance with the invention.

Examples of suitable anti-obesity agents for use in combination with the compounds of the present invention include melanocortin receptor (MC4R) agonists, cannabinoid receptor modulators, endocannabinoid synthesis modulators, GPR119 agonists, inhibitors of fat absorption, growth hormone secretagogue receptor (GHSR) antagonists, galanin receptor modulators, orexin antagonists, SGLT2 inhibitors, DPP4 inhibitors, triple monoamine reuptake inhibitors, CCK agonists, GLP-1 agonists, and other Pre-proglucagon-derived peptides; NPY1 or NPY5 antagonist, NPY2 modulators, MCHR1 antagonists, corticotropin releasing factor modulators, histamine receptor-3 (H3) modulators, aP2 inhibitors, PPAR gamma modulators, PPAR delta modulators, acetyl-CoA carboxylase (ACC) inhibitors, steroyl Co-A desaturase-1 (SCD-1) inhibitors, 11-β-HSD-1 inhibitors, adiponectin receptor modulators; beta 3 adrenergic agonists, thyroid receptor beta modulators, lipase inhibitors, serotonin receptor agonists, monoamine reuptake inhibitors or releasing agents, anorectic agents, CNTF (ciliary neurotrophic factor), BDNF (brain-derived neurotrophic factor), leptin and leptin receptor modulators, cannabinoid-1 receptor inverse agonists/neutral antagonists, DGAT inhibitors, opiate antagonists, and amylin receptor modulators.

Preferred antiobesity agents include SGLT2 inhibitors, such as those disclosed in U.S. Pat. No. 6,414,126. Most preferred anti-obesity agents include dapagliflozin and lipase inhibitors, such as orlistat, or monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

Examples of suitable anti-diabetic agents for use in combination with the compounds of the present invention include: oral antihyperglycemic agents, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glucokinase inhibitors, glycogen phosphorylase inhibitors, and/or meglitinides, as well as insulin, and/or glucagon-like peptide-1 (GLP-1), GLP-1 agonist, a PTP-1B inhibitor (protein tyrosine phosphatase-1B inhibitor), and/or a histone deacetylase modulator such as a SIRT1 activator.

The compounds of the present invention may be employed in combination with anti-hyperlipidemia agents, or agents used to treat arteriosclerosis. An example of an hypolipidemic agent would be a fibric acid derivatives, bile acid sequestrants, nicotinic acid, aspirin, poly(diallylmethylamine) derivatives, quaternary amine poly(diallyldimethylammonium chloride) and ionenes and other known serum cholesterol lowering agents. Hypolipidemic agents include ACAT inhibitors, an upregulator of LDL receptor activity, and cholesterol absorption inhibitors.

Lipid agent or lipid-modulating agents include cholesteryl transfer protein inhibitors (CETP) The hypolipidemic agent may be an ileal Na+/bile acid cotransporter inhibitor such as disclosed in Drugs of the Future, 24:425-430 (1999). The ATP citrate lyase inhibitor which may be employed in the combination of the invention may include, for example, those disclosed in U.S. Pat. No. 5,447,954.

The other lipid agent also includes a phytoestrogen compounds, a beta-lactam cholesterol absorption inhibitor, a PPAR α-agonist and/or an FXR agonist; an LDL catabolism promoter, a sodium-proton exchange inhibitor; an LDL-receptor inducer or a steroidal glycoside; an anti-oxidant, an antihomocysteine agent, a cholesterol absorption inhibitor, an HMG-CoA synthase inhibitor, or a lanosterol demethylase inhibitor, a sterol regulating element binding protein-I (SREBP-1).

Biological Data

NPY4 cAMP HTRF Agonist Assay

The functionality of the compound at Y4 receptor was analyzed using an inhibitory cAMP assay (CISBIO, HTRF cAMP kit #62AM4PEC) to measure the Gi activation by Y4 agonism.

The human Y4 stable CHO clonal cells were maintained in culture medium (F-12 containing 10% Fetal Bovine Serum, 50 mg/ml GENETICIN®, 100 mg/ml Zeocin). Before the experiment, 5 µL of 1 uM Forskolin (Sigma, # F6886) and 100 uM IBMX (Sigma, #15879) in PBS buffer were added into 384-well plates (PE, Proxi-plate) that were pre-dotted with 100 mL compounds. The cells were removed from the flasks by Cellstripper, counted and adjusted to $1.0 \times 10^6$ cells/mL in PBS buffer, and added 5 µL/well (5000 cells/well) into the above 384-well plates. The cells were then covered and incubated for 30 minutes at room temperature. After incubation, 5 µL/well of D2-conjugate in HTRF lysis buffer was first added, followed by adding 5 µL/well of anti-cAMP Cryptate in HTRF lysis buffer. The plates were incubated for another 1 hour at room temperature and read on the EnVision Multilabel Plate Reader.

Compounds described herein were tested in the above assay. The following results were obtained.

TABLE 1

| NPY4 cAMP HTRF Agonist Assay EC50 (nM) | |
|---|---|
| Compound | EC50 (nM) |
| Example 1 | 81 |
| Example 3 | 46 |
| Example 4 | 25 |
| Example 7 | 72 |
| Example 10 | 330 |
| Example 16 | 72 |
| Example 32 | 540 |
| Example 34 | 575 |
| Example 36 | 610 |
| Example 43 | 1400 |
| Example 45 | 1460 |
| Example 52 | 2890 |
| Example 56 | 3615 |
| Example 58 | 10 |
| Example 63 | 515 |
| Example 89 | 2340 |

III. Methods of Preparation

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

General Schemes:

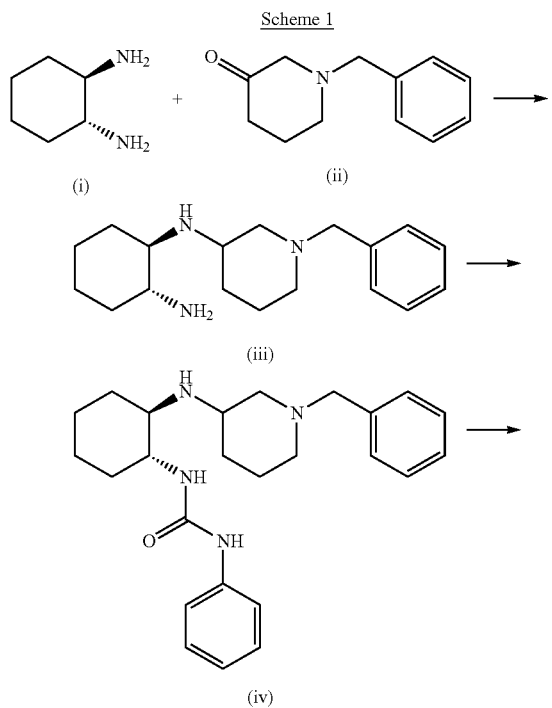

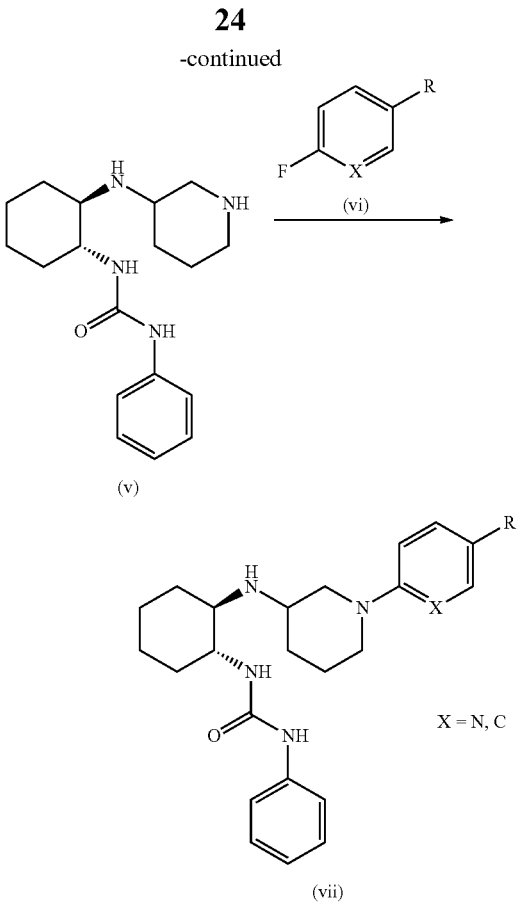

Compounds of formula I can be made according to the general procedure shown in Scheme 1 by starting the reductive condensation of a ketone, for example compound (II), with diaminocyclohexane under reductive amination conditions, for example employing sodium triacetoxyborohydride, sodium cyanoborohydride, or the like. The resulting compound (iii) is then reacted with an isocyanate in an inert solvent such as dichloromethane to give a urea. The resulting urea, compound (iv) is then debenzylated using hydrogenation conditions. The amine, compound (v) is the reacted with an aryl or heteroaryl fluoride to give compounds of general structure (vii) as a diastereomeric mixture. The resulting diastereomers of compound (vii) can be separated using chromatography (HPLC) techniques or by fractional crystallization.

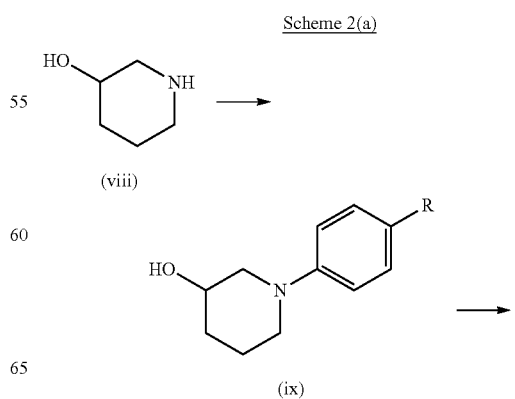

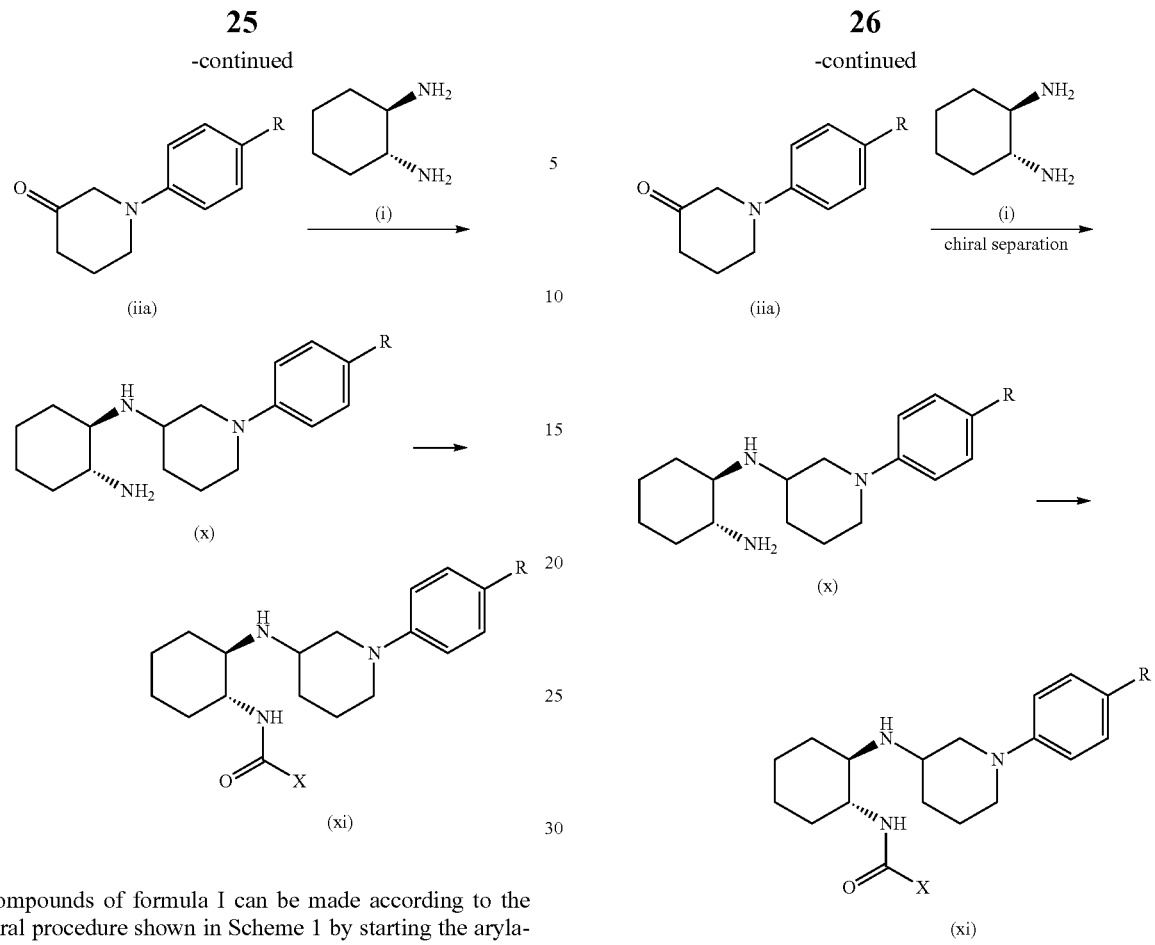

Compounds of formula I can be made according to the general procedure shown in Scheme 1 by starting the arylation of a cyclic amino alcohol such as compound (viii) using aryl borohydrides under palladium or copper mediated cross coupling conditions. The resulting alcohol, compound (ix), is then oxidized to the corresponding ketone by using oxidative conditions, such as the Swern oxidation, SO₃-pyridine complex mediated oxidation and the like. The resulting arylated amine, is then condensed with diaminocyclohexane employing reductive amination conditions to give compound (x). Compound (x) can then be reacted with isocyanates to give ureas, acid chlorides or carboxylic acids (using amide coupling conditions) or with chloro carbonates or carbonic anhydrides to give carbamates. The resulting product, compound (xi), can be separated using chromatography (HPLC) techniques or by fractional crystallization.

Compounds of formula I can be made according to the general procedure shown in Scheme 1 by starting with the arylation of a cyclic amino alcohol such as compound (viii) using aryl borohydrides under palladium or copper mediated cross coupling conditions. The resulting alcohol, compound (ix), is then oxidized to the corresponding ketone by using oxidative conditions, such as the Swern oxidation, SO₃-pyridine complex mediated oxidation and the like. The resulting arylated amine, is then condensed with diaminocyclohexane employing reductive amination, followed by chiral separation conditions to give compound (x) as a single enantiomer. Compound (x) can then be reacted with isocyanates to give ureas, acid chlorides or carboxylic acids (using amide coupling conditions) or with chloro carbonates or carbonic anhydrides to give carbamates.

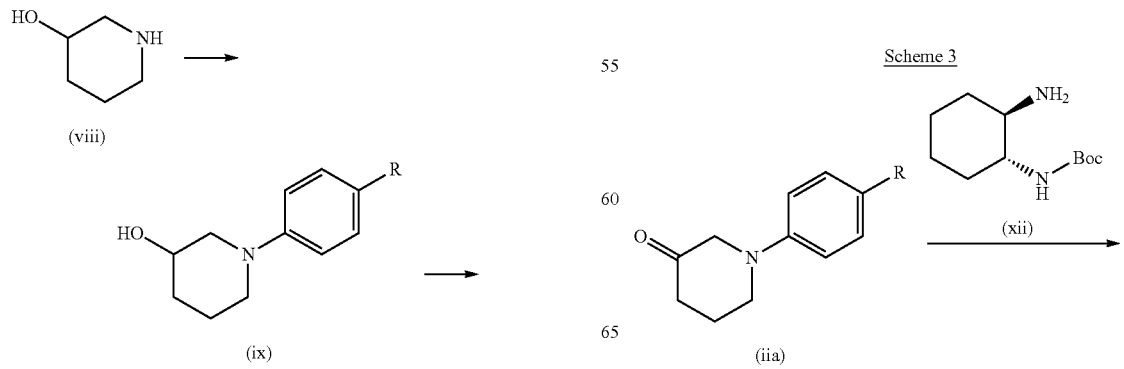

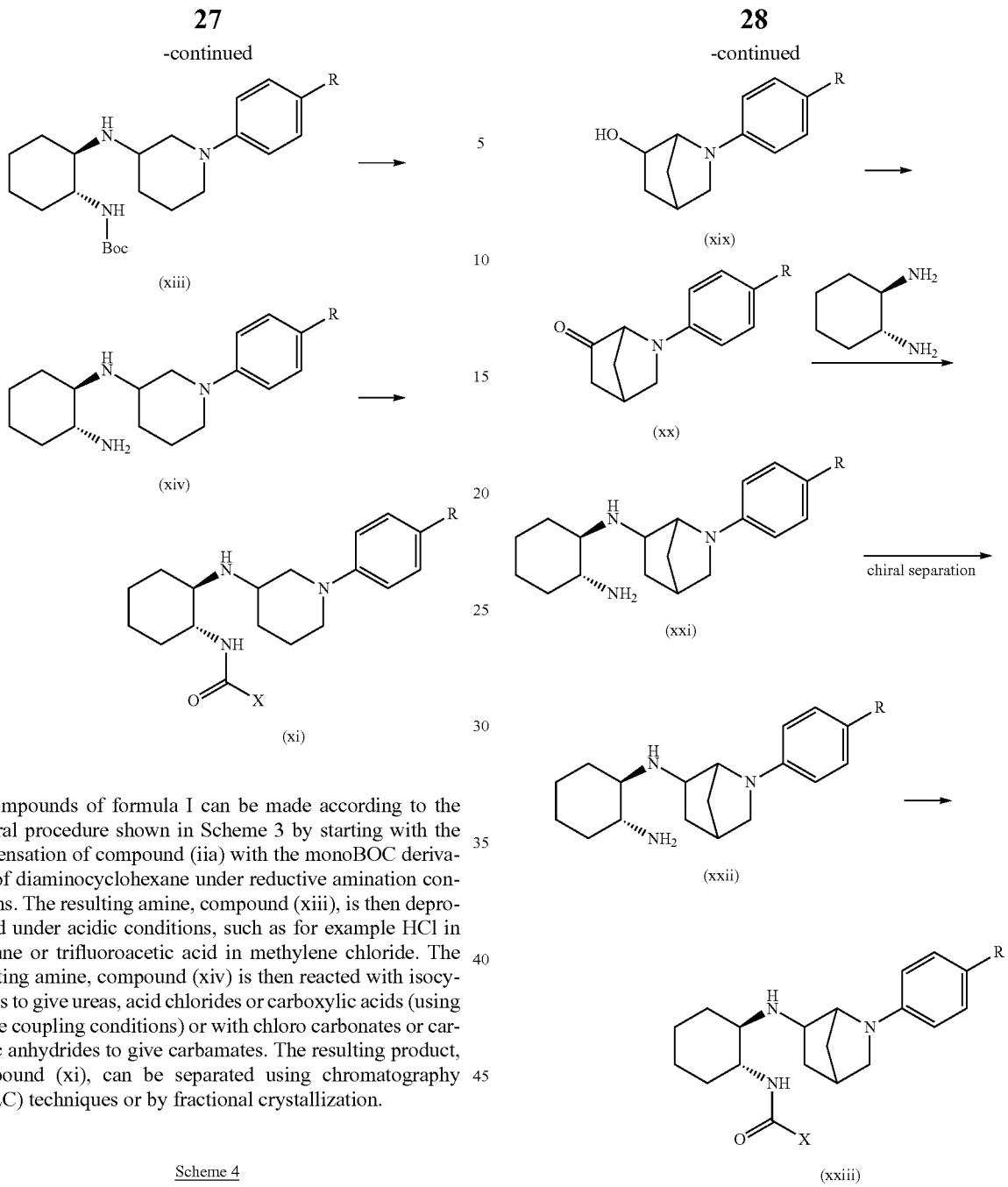

Compounds of formula I can be made according to the general procedure shown in Scheme 3 by starting with the condensation of compound (iia) with the monoBOC derivative of diaminocyclohexane under reductive amination conditions. The resulting amine, compound (xiii), is then deprotected under acidic conditions, such as for example HCl in dioxane or trifluoroacetic acid in methylene chloride. The resulting amine, compound (xiv) is then reacted with isocyanates to give ureas, acid chlorides or carboxylic acids (using amide coupling conditions) or with chloro carbonates or carbonic anhydrides to give carbamates. The resulting product, compound (xi), can be separated using chromatography (HPLC) techniques or by fractional crystallization.

Scheme 4

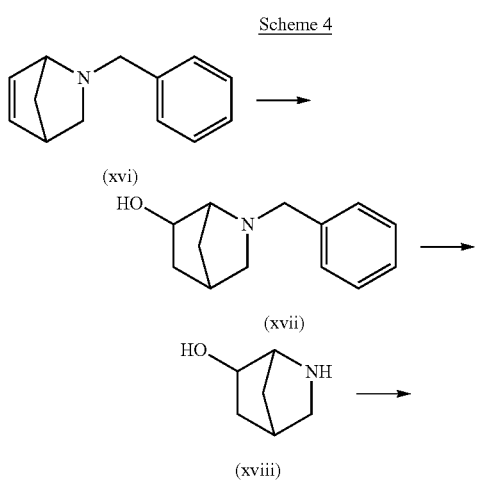

Compounds of formula I can be made according to the general procedure shown in Scheme 3 by starting with the hydroxylation of a double bond, compound (xvi). The resulting alcohol, compound (xvii) is then debenzylated. The resulting amine, compound (xviii) is then arylated to give compound (xix). The alcohol is oxidized to a ketone. The corresponding ketone, compound (xx) is then reacted with diaminocyclohexane under reductive amination conditions to give compound (xxi). Compound (xxi) can be separated into a chirally pure enantiomer using chromatography (HPLC) techniques or by fractional crystallization. The resulting free amine compound (xxii) is then reacted with isocyanates to give ureas, acid chlorides or carboxylic acids (using amide coupling conditions) or with chloro carbonates or carbonic anhydrides to give carbamates.

| Abbreviations | |
|---|---|
| $CH_2Cl_2$ | methylene chloride |
| DMF | dimethyl formamide |
| DMSO | dimethyl sulfoxide |
| EDC | 1-[3-(dimethylamino)propyl]-3-ethylcarbodiimide hydrochloride |
| eq | Equivalent |
| $Et_3N$ | triethyl amine |
| EtOAc | ethyl acetate |
| HCl | hydrogen chloride |
| Hex | Hexanes |
| HOAc | acetic acid |
| HOBT | 1-hydroxybenzotriazole hydrate |
| HPLC | High Performance Liquid Chromatography |
| $K_2CO_3$ | potassium carbonate |
| mesyl | Methanesulfonyl |
| MeOH | Methanol |
| $MgSO_4$ | magnesium sulfate |
| mmol | Millimole |
| min | Minute |
| $Na_2SO_4$ | sodium sulfate |
| NaCl | sodium chloride |
| $NaHCO_3$ | sodium bicarbonate |
| $NH_3$ | Ammonia |
| RP | reverse phase |
| rt | room temperature |
| TFA | trifluoro acetic acid |
| THF | Tetrahydrofuran |

Preparatory HPLC method A was performed on a Shimadzu SCL-10A liquid chromatograph with a linear gradient of 20-100% Solvent B over 10 or 30 minutes, with either a 2 or 5 minutes (respectively) hold at 100% Solvent B;

UV visualization at 220 nm;
Column. Axia Luna 5u C18 30×100 mm;
Flow rate: 20 mL/min;
Solvent A: 10% MeOH, 90% Water, 0.1% Trifluoroacetic Acid; and
Solvent B: 90% MeOH, 10% Water, 0.1% Trifluoroacetic Acid.

Chiral preparatory HPLC method A was performed on a Berger MGII SFC liquid chromatograph:

| | |
|---|---|
| Column: | CHIRALCEL ® OD-H 25 X 3 cm ID, 5 µm |
| Flow rate: | 60.0 mL/min |
| Mobile Phase: | 85/15 $CO_2$/MeOH-0.1 v/v % DEA |
| Detector Wavelength: | 237 nm |
| Injection Volume: | 200 µL |

Chiral preparatory HPLC method B was performed on a Berger MGII SFC liquid chromatograph:

| | |
|---|---|
| Column: | CHIRALPAK ® AD, 250 X 30 mm ID, 5 µm |
| Flow rate: | 115 mL/min, 100 Bar, 35 µC |
| Mobile Phase: | 25% Methanol/75% $CO_2$ |
| Detector Wavelength: | 230 nm |
| Injection Volume: | 1000 µL |

Chiral preparatory HPLC method C was performed on a Shimadzu liquid chromatograph:

| | |
|---|---|
| Column. | CHIRALPAK ® OJ, 250 X 20 mm ID, 5 µm |
| Flow rate: | 10 mL/min |
| Mobile Phase: | 5% Ethanol/95% Hex with 0.1% DEA |
| Detector Wavelength: | 254 nm |

Chiral preparatory HPLC method D was performed on an Agilent 1200 series liquid chromatograph:

| | |
|---|---|
| Column: | CHIRALPAK ® AD-H, 250 X 20 mm ID, 5 µm |
| Flow rate: | 10 mL/min |
| Mobile Phase: | 20% Ethanol/80% Hex with 0.2% DEA |
| Detector Wavelength: | 220 nm |

Chiral preparatory HPLC method E was performed on a Agilent 1200 series liquid chromatograph:

| | |
|---|---|
| Column: | CHIRALPAK ® OJ-H, 250 X 20 mm ID, 5 µm |
| Flow rate: | 10 mL/min |
| Mobile Phase: | 5% Isopropanol/95% Hex with 0.2% DEA |
| Detector Wavelength: | 254 nm |

GENERAL PROCEDURES

General Procedure A

N-Arylation of Piperidinol Using an Aryl-Fluoride

To a round bottom flask was added piperidin-3-ol (1 eq), aryl fluoride (1 eq), DMF and $K_2CO_3$ (1.2 eq). The reaction was stirred at 65° C. for 6 hrs. After this time, the reaction was diluted with EtOAc. The resulting solution was washed with water (4×) and saturated aqueous NaCl. The organic layer was separated, dried over $MgSO_4$, filtered and concentrated. The resulting residue was purified using silica gel chromatography (ISCO system) eluting with a gradient of 0-100% EtOAc/Hex to give the product N-arylpiperidin-3-ol.

General Procedure B

N-Arylation of Piperidinol Using CuI

Piperidin-3-ol (1 eq), aryl-bromide, $K_2CO_3$ (2 eq), L-proline (0.2 eq), copper(I) iodide (0.1 eq) and DMSO were added to a glass pressure tube. After addition, the tube was sealed and placed in a heating bath at 65° C. The reaction was stirred at 65° C. for 48 hrs. After this time the reaction was cooled to rt. The reaction mixture was diluted with EtOAc. The resulting solution was washed with water (2×) and saturated aqueous NaCl. The organic layer was separated, dried over $MgSO_4$, filtered and concentrated. The resulting residue was purified using silica gel chromatography (ISCO system) eluting with a gradient of 0-100% EtOAc/Hex) to give the product N-arylpiperidin-3-ol.

General Procedure C

Oxidation of N-Aryl-piperidinol Using Py.SO₃ Complex

To a round bottom flask was added N-arylpiperidinol (1 eq), $Et_3N$ (5 eq) and $CH_2Cl_2$. The resulting solution was cooled to 0° C. In a separate vial, pyridine sulfur trioxide (5 eq) and DMSO (20 eq) were mixed until the solution turned clear. The resulting solution was then added to the reaction at 0° C. The reaction mixture was slowly warmed to rt and stirred for an additional 2 hrs. After this time, the solution was diluted with $CH_2Cl_2$. The resulting solution was washed with water (2×) and saturated aqueous NaCl. The organic layer was separated, dried over $MgSO_4$, filtered and concentrated. The resulting residue was purified using silica gel chromatography (ISCO system) eluting with a gradient of 0-100% EtOAc/Hex to give the product N-arylpiperidinone.

General Procedure D

Oxidation of N-Aryl-piperidinol Using Swern Oxidation Conditions

To a round bottom flask was added CH$_2$Cl$_2$, 2M oxalyl chloride (1.4 eq). The resulting solution was cooled to −78° C. DMSO (2.8 eq) was then slowly added to the solution over 10 min. The reaction was then stirred at −78° C. for 15 min. The N-aryl-piperidinol (1 eq) pre-dissolved in CH$_2$Cl$_2$ was added to the reaction mixture over 10 min. The resulting solution was stirred at −78° C. for 2 hrs. After this time, Et$_3$N (4.4 eq) was added to the reaction mixture and the resulting solution was slowly warmed to 0° C. over 20 min. The reaction mixture was then diluted with CH$_2$Cl$_2$. The reaction mixture was washed with saturated aqueous NaHCO$_3$, water and saturated aqueous NaCl. The organic layer was separated, dried over MgSO$_4$, filtered and concentrated to give crude product. The resulting residue was purified using silica gel chromatography (ISCO system) eluting with a gradient of 0-100% EtOAc/Hex to give the product N-arylpiperidinone.

General Procedure E

Reductive Amination Using Cyclohexane Diamine and an N-Arylpiperidinone

To a round bottom flask under argon was added the N-arylpiperidinone (1 eq), (1R,2R)-cyclohexane-1,2-diamine (1 eq), CH$_2$Cl$_2$, solid anhydrous Na$_2$SO$_4$ and HOAc (1 eq). Argon was bubbled through the reaction mixture for 1 min and then the reaction was stirred under argon at rt for 1 hr. After this time, sodium triacetoxy borohydride (3 eq) was added to the reaction which was then stirred at rt for additional 4 hrs. At this time, HPLC analysis showed the starting was consumed. The reaction mixture was then diluted with CH$_2$Cl$_2$. The resulting solution was washed with water (2×) and saturated aqueous NaCl. The organic layer was separated, dried over MgSO$_4$, filtered and concentrated. The resulting residue was purified using RP prep-HPLC. The desired fractions containing the product were concentrated to give the product amine

General Procedure F

Reductive Amination Using tert-Butyl (1R,2R)-2-aminocyclohexylcarbamate and an N-Arylpiperidinone To a round bottom flask under argon was added the N-arylpiperidinone (1 eq), tert-butyl (1R,2R)-2-aminocyclohexylcarbamate (1 eq), CH$_2$Cl$_2$, solid anhydrous Na$_2$SO$_4$ and HOAc (1 eq). Argon was bubbled through the reaction mixture for 1 min and then the reaction was stirred under argon at rt for 1 hr. After this time, sodium triacetoxy borohydride (3 eq) was added to the reaction which was then stirred at rt for additional 4 hrs. At this time, HPLC analysis showed the starting was consumed. The reaction mixture was then diluted with CH$_2$Cl$_2$. The resulting solution was washed with water (2×) and saturated aqueous NaCl. The organic layer was separated, dried over MgSO$_4$, filtered and concentrated. The resulting residue was purified using silica gel chromatography (ISCO system) eluting with a gradient of 0-100% EtOAc/Hex. The desired fractions containing the product were concentrated to give the product.

General Procedure G

Derivatization to Form a Urea

To a round bottom flask was added N-substituted cyclohexane-1,2-diamine (1 eq), THF, and Et$_3$N (2 eq). To the resulting solution was added an isocyanate (0.95 eq). The reaction was stirred at rt for 30 min. After this time, the reaction mixture was concentrated. The resulting crude product was purified by RP prep-HPLC. The desired fractions containing the product were concentrated to give the product urea.

General Procedure H

Derivatization to Form a Carbamate

To a round bottom flask was added N-substituted cyclohexane-1,2-diamine (1 eq), CH$_2$Cl$_2$, Et$_3$N (5 eq) and ROC(O)Cl (1 eq) or R—OSU (1 eq). The reaction was stirred at rt for 2 hrs. After this time, the reaction mixture was concentrated. The resulting crude product was purified by RP prep-HPLC. The desired fractions containing the product were concentrated to give the product carbamate.

General Procedure I

Derivatization to Form an Amide

To a round bottom flask was added substituted N-cyclohexane-1,2-diamine (1 eq), carboxylic acid (1 eq), EDC (1.2 eq), HOBT (1.2 eq), Et$_3$N (3 eq), and CH$_2$Cl$_2$. The resulting reaction was stirred at rt for 4 hrs. After this time, the reaction mixture was concentrated. The resulting residue was dissolved in EtOAc and the organic solution was washed with water and saturated aqueous NaCl. The organic layer was dried over MgSO$_4$, filtered and concentrated. The resulting crude product was purified by RP prep-HPLC. The desired fractions containing the product were concentrated to give the product amide.

General Procedure J

Removal of Boc Group Using TFA and CH$_2$Cl$_2$

To a round bottom flask was added Boc protected amine, 1:1 mixture of CH$_2$Cl$_2$ and TFA. The reaction was stirred at rt for 1 hr. The solvent was removed to give the product amine as TFA salt.

Example 1

1-((1R,2R)-2-((S)-1-(4-Nitrophenyl)piperidin-3-ylamino)cyclohexyl)-3-phenyl urea

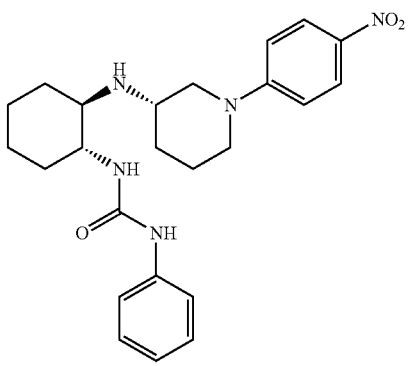 [SMILES: O=C(Nc1ccccc1)N[C@@H]1CCCC[C@H]1N[C@H]1CCCN(c2ccc([N+](=O)[O-])cc2)C1]

A: (1R,2R)—N1-(1-Benzylpiperidin-3-yl)cyclohexane-1,2-diamine

1-Benzyl-3-piperidone hydrochloride monohydrate (5.93 g, 26.3 mmol) was partitioned between a saturated aqueous NaHCO$_3$ solution (30 ml) and CH$_2$Cl$_2$ (50 mL). The organic layer was separated and dried over Na$_2$SO$_4$ and filtered. The filtrated was collected and (1R,2R)-cyclohexane-1,2-diamine (3 g, 26.3 mmol) was added followed by sodium triacetoxy borohydride (8.35 g, 39.4 mmol). The reaction was stirred at rt overnight. After this time, the reaction was quenched with water (2 ml). The resulting solution was washed with saturated aqueous NaHCO$_3$ (50 ml) and saturated NaCl (50 ml). The organic layer was dried over MgSO$_4$, filtered and concentrated. The resulting residue was purified by RP Prep-HPLC. The desired fractions containing the product were concentrated to give the product, (1R,2R)—N1-(1-benzylpiperidin-3-yl)cyclohexane-1,2-diamine (3.01 g, 10.47 mmol, 40% yield) as a trifluoroacetate salt and as a white solid. $^1$H NMR (500 MHz, MeOH-d$_3$) δ ppm 7.54-7.36 (m, 5H), 4.27-3.99 (m, 2H), 3.24-2.94 (m, 3H), 2.69 (d, J=9.90 Hz, 2H), 2.46-2.27 (m, 1H); 2.25-2.02 (m, 2H); 2.03-1.83 (m, 2H); 1.83-1.62 (m, 4H); 1.47-1.19 (m, 4H); 1.05 (d, J=11.55 Hz, 1H). $^{13}$C NMR (126 MHz, MeOH-d$_3$) δ ppm 132.27, 130.75, 130.25, 62.31, 58.81, 56.46, 53.57, 32.76, 31.33, 25.99, 25.73, 25.40

B: 1-((1R,2R)-2-(1-Benzylpiperidin-3-ylamino)cyclohexyl)-3-phenylurea

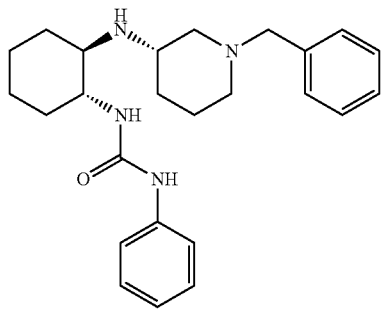 [SMILES: O=C(Nc1ccccc1)N[C@@H]1CCCC[C@H]1N[C@H]1CCCN(Cc2ccccc2)C1]

To a round bottom flask was added (1R,2R)—N1-(1-benzylpiperidin-3-yl)cyclohexane-1,2-diamine (3.23 g, 8.05 mmol), THF (30 mL), isocyanatobenzene (0.958 g, 8.05 mmol) and Et$_3$N (5.61 mL, 40.2 mmol). The reaction was stirred at rt for 2 hrs. After this time, the reaction mixture was concentrated. The residue was diluted with EtOAc (100 ml). The resulting solution was washed with water (50 ml) and saturated aqueous NaCl (50 ml). The organic layer was dried over MgSO$_4$, filtered and concentrated. The resulting residue was purified using silica gel chromatography (ISCO system) eluting with 5% MeOH/CH$_2$Cl$_2$ with NH$_3$) to give the product, 1-((1R,2R)-2-(1-benzylpiperidin-3-ylamino)cyclohexyl)-3-phenylurea (1.4 g, 3.44 mmol, 42.8% yield), as a white solid. Anal. Calcd. for C$_{25}$H$_{32}$N$_4$O m/z 407, found: 408.2 (M+H)$^+$; $^1$H NMR (500 MHz, CDCl$_3$) δ ppm 7.41-7.15 (m, 9H), 6.97 (q, J=7.15 Hz, 1H), 4.51-4.27 (m, 1H), 3.58-3.34 (m, 2H), 3.23-3.08 (m, 1H), 2.96-2.80 (m, 1H), 2.66 (br. s., 1H), 2.40 (br. s., 1H), 2.29-2.11 (m, 2H), 2.11-1.92 (m, 2H), 1.77-1.57 (m, 5H), 1.57-1.42 (m, 1H), 1.31 (d, J=3.85 Hz, 1H), 1.30-1.05 (m, 4H).

C: 1-Phenyl-3-((1R,2R)-2-(piperidin-3-ylamino)cyclohexyl)urea

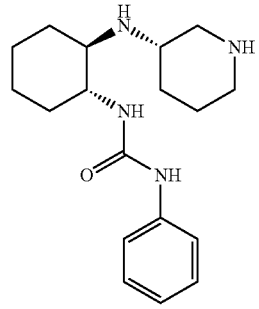 [SMILES: O=C(Nc1ccccc1)N[C@@H]1CCCC[C@H]1N[C@H]1CCCNC1]

To a PARR shaker was added 1-((1R,2R)-2-(1-benzylpiperidin-3-ylamino)cyclohexyl)-3-phenylurea (1.4 g, 3.44 mmol), Pd(OH)$_2$ (0.484 g, 3.44 mmol), MeOH (20 mL) and 3 drops of 1N HCl. The reaction vessel charged with hydrogen and the pressure was maintained at 30 psi with shaking overnight. After this time, the reaction was filtered through CELITE® and the filtrate was concentrated to give the product, 1-phenyl-3-((1R,2R)-2-(piperidin-3-ylamino)cyclohexyl)urea (1.05 g, 3.32 mmol, 96% yield), as an off white solid. It was used in the next step without further purification. Anal. Calcd. for C$_{18}$H$_{28}$N$_4$O m/z 316, found: 317.3 (M+H)$^+$; $^1$H NMR (500 MHz, methanol-d$_3$) δ ppm 7.35 (d, J=7.70 Hz, 2H), 7.24 (t, J=7.42 Hz, 2H), 6.97 (t, J=7.42 Hz, 1H), 3.49-3.37 (m, 1H), 3.16-3.03 (m, 1H), 2.94-2.83 (m, 1H), 2.70 (td, J=9.35, 4.95 Hz, 1H), 2.57-2.47 (m, 1H), 2.47-2.39 (m, 1H), 2.39-2.25 (m, 1H), 2.10-1.90 (m, 3H), 1.79-1.68 (m, 3H), 1.58-1.43 (m, 1H), 1.39-1.16 (m, 5H).

D: 1-((1R,2R)-2-((S)-1-(4-Nitrophenyl)piperidin-3-ylamino)cyclohexyl)-3-phenylurea

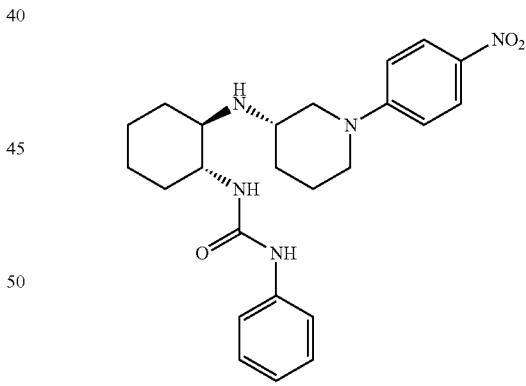

1-((1R,2R)-2-((S)-1-(4-Nitrophenyl)piperidin-3-ylamino)cyclohexyl)-3-phenylurea (15 mg) was synthesized in 13% yield using the procedures as described in General Procedure A using 1-fluoro-4-nitrobenzene (39.2 mg, 0.278 mmol) and 1-phenyl-3-((1R,2R)-2-(piperidin-3-ylamino)cyclohexyl)urea (80 mg, 0.253 mmol). Anal. Calcd. for C$_{24}$H$_{31}$N$_5$O$_3$ m/z 437.5, found: 438.4 (M+H)$^+$; $^1$H NMR (500 MHz, CDCl$_3$) δ ppm 9.12 (s, 1H), 7.66 (d, J=8.8 Hz, 2H), 7.37 (br. s., 1H), 7.31 (d, J=8.2 Hz, 2H), 7.15 (t, J=7.7 Hz, 2H), 6.98 (t, J=6.9 Hz, 1H), 6.59 (d, J=8.8 Hz, 2H), 3.68 (br. s., 3H), 3.43-3.34 (m, 1H), 3.26-3.17 (m, 2H), 2.95 (br. s., 1H), 2.32 (br. s., 1H), 2.20-2.11 (m, 1H), 2.05 (br. s., 2H), 1.96 (br. s., 2H), 1.82-

1.75 (m, 1H), 1.65 (d, J=15.9 Hz, 2H), 1.46 (br. s., 1H), 1.19 (d, J=9.9 Hz, 2H); $^{13}$C NMR (126 MHz, CDCl$_3$) δ ppm 158.96, 153.92, 138.94, 138.78, 128.79, 125.85, 122.92, 118.37, 113.48, 64.58, 53.54, 53.22, 49.48, 47.42, 45.94, 31.34, 29.50, 23.76, 21.69, 14.11, 8.63.

Example 2

1-((1R,2R)-2-((S)-1-(4-Nitrophenyl)piperidin-3-ylamino)cyclohexyl)-3-(4-(trifluoromethyl)phenyl) urea

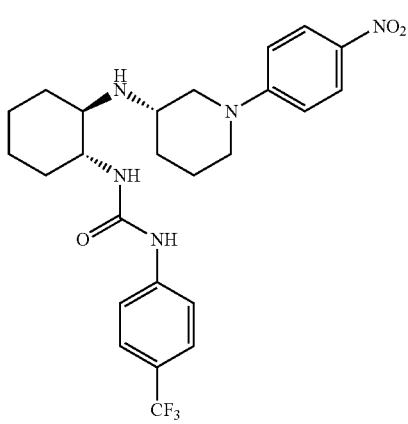 [SMILES: O=C(Nc1ccc(C(F)(F)F)cc1)N[C@@H]1CCCC[C@H]1N[C@H]1CCCN(c2ccc([N+](=O)[O-])cc2)C1]

A: 1-(4-Nitrophenyl)piperidin-3-ol

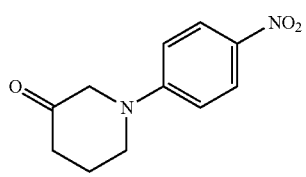 [SMILES: O=C1CCCN(c2ccc([N+](=O)[O-])cc2)C1]

1-(4-Nitrophenyl)piperidin-3-ol was synthesized as described in General Procedure A using 1-fluoro-4-nitrobenzene (4.41 g, 31.2 mmol) and piperidin-3-ol (4.3 g, 31.2 mmol) to give an orange solid (6.8 g, 30.6 mmol, 98% yield). Anal. Calcd. for C$_{11}$H$_{14}$N$_2$O$_3$ m/z 222.2, found: 223.3 (M+H)$^+$; $^1$H NMR (500 MHz, CDCl$_3$) δ ppm 8.14-7.98 (m, 2H), 6.83 (d, J=9.35 Hz, 2H), 3.89 (d, J=3.85 Hz, 1H), 3.72 (dd, J=12.92, 3.57 Hz, 1H), 3.53 (ddd, J=13.06, 5.91, 3.02 Hz, 1H), 3.33-3.16 (m, 2H), 2.10-1.97 (m, 2H), 1.96-1.84 (m, 1H), 1.75-1.50 (m, 2H).

B: 1-(4-Nitrophenyl)piperidin-3-one

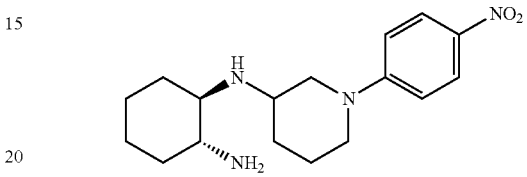

1-(4-Nitrophenyl)piperidin-3-one was synthesized as described in General Procedure C using 1-(4-nitrophenyl) piperidin-3-ol (5.0 g, 22.50 mmol) to give an orange solid (4.2 g, 85% yield). Anal. Calcd. for C$_{11}$H$_{12}$N$_2$O$_3$ m/z 220.2, found: 221.2 (M+H)$^+$; $^1$H NMR (500 MHz, CDCl$_3$) δ ppm 8.16 (d, J=9.35 Hz, 2H), 6.75 (d, J=9.35 Hz, 2H), 4.04 (s, 2H), 3.64 (t, J=6.05 Hz, 2H), 2.60 (t, J=6.60 Hz, 2H), 2.22 (t, J=6.05 Hz, 2H); $^{13}$C NMR (126 MHz, CDCl$_3$) δ ppm 204.84, 153.09, 138.61, 126.04, 111.52, 56.05, 45.70, 37.99, 21.49.

C: (1R,2R)—N1-(1-(4-Nitrophenyl)piperidin-3-yl) cyclohexane-1,2-diamine

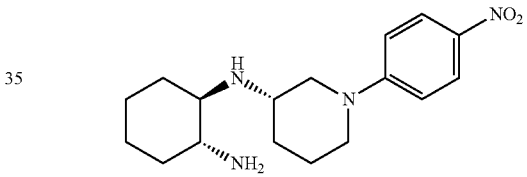

(1R,2R)—N1-(1-(4-Nitrophenyl)piperidin-3-yl)cyclohexane-1,2-diamine was synthesized as described in General Procedure E using 1-(4-nitrophenyl)piperidin-3-one (3.0 μm, 13.62 mmol) to give a yellow solid (3.5 g, 81% yield). Anal. Calcd. for C$_{17}$H$_{26}$N$_4$O$_2$ m/z 318.4, found: 319.3 (M+H)$^+$.

D: (1R,2R)—N1-((S)-1-(4-Nitrophenyl)piperidin-3-yl)cyclohexane-1,2-diamine (1R,2R)—N1-((S)-1-(4-Nitrophenyl)piperidin-3-yl)cyclohexane-1,2-diamine was separated from (1R,2R)—N1-((R)-1-(4-Nitrophenyl)piperidin-3-yl)cyclohexane-1,2-diamine using chiral separation method C.

E: 1-((1R,2R)-2-((S)-1-(4-Nitrophenyl)piperidin-3-ylamino)cyclohexyl)-3-(4-(trifluoromethyl)phenyl) urea

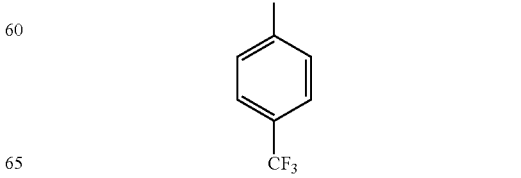

1-((1R,2R)-2-((S)-1-(4-Nitrophenyl)piperidin-3-ylamino) cyclohexyl)-3-(4-(trifluoromethyl)phenyl)urea was synthesized as described in General Procedure F using 4-trifluoromethyl-phenyl isocyanate (13 mg, 0.069 mmol) and (1R,2R)—N1-(1-(4-nitrophenyl)piperidin-3-yl)cyclohexane-1,2-diamine (30 mg, 0.069 mmol) to give 1-((1R,2R)-2-((S)-1-(4-nitrophenyl)piperidin-3-ylamino)cyclohexyl)-3-(4-(trifluoromethyl)phenyl)urea as a yellow solid (2.0 mg, 54% yield). Anal. Calcd. for $C_{25}H_{30}F_3N_5O_3$ m/z 505.5, found: 506.3 (M+H)$^+$; $^1$H NMR (500 MHz, CDCl$_3$) δ ppm 9.61-8.86 (m, 1H), 8.76 (br. s., 1H), 7.72 (d, J=8.80 Hz, 2H), 7.42-7.33 (m, 2H), 7.30 (d, J=8.25 Hz, 2H), 7.06 (br. s., 1H), 6.66 (d, J=8.80 Hz, 2H), 3.75-3.56 (m, 2H), 3.48 (d, J=12.65 Hz, 1H), 3.44-3.29 (m, 2H), 3.25 (d, J=7.70 Hz, 1H), 3.11 (br. s., 1H), 2.24-2.00 (m, 4H), 1.86 (d, J=13.20 Hz, 3H), 1.84-1.75 (m, 1H), 1.71 (d, J=11.00 Hz, 1H), 1.49 (br. s., 1H) 1.37-1.17 (m, 2H); $^{13}$C NMR (126 MHz, CDCl$_3$) δ ppm 154.35, 144.05, 125.87, 125.55, 123.02, 120.76, 117.83, 114.19, 66.81, 63.17, 52.86, 52.53, 48.20, 31.08, 28.87, 26.95, 23.72, 22.69, 21.03.

Example 3

1-((1R,2R)-2-((S)-1-(4-Nitrophenyl)piperidin-3-ylamino)cyclohexyl)-3-(4-(trifluoromethoxy)phenyl)urea

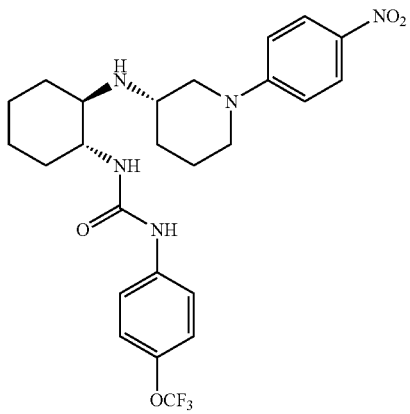 [SMILES: O=C(Nc1ccc(OC(F)(F)F)cc1)N[C@@H]1CCCC[C@H]1N[C@H]1CCCN(c2ccc([N+](=O)[O-])cc2)C1]

1-((1R,2R)-2-((S)-1-(4-Nitrophenyl)piperidin-3-ylamino) cyclohexyl)-3-(4-(trifluoromethoxy)phenyl)urea was synthesized as described in General Procedure G, using 1-isocyanato-4-(trifluoromethoxy)benzene (15.31 mg, 0.075 mmol) and (1R,2R)—N1-(1-(4-nitrophenyl)piperidin-3-yl)cyclohexane-1,2-diamine (24 mg, 0.075 mmol) to give 15 mg (30% yield) of the title compound as a yellow solid. Anal. Calcd. for $C_{25}H_{30}F_3N_5O_4$ m/z 521.5, found: 522.3 (M+H)$^+$; $^1$H NMR (500 MHz, CDCl$_3$) δ ppm 7.77 (d, J=8.80 Hz, 2H), 7.22 (d, J=8.80 Hz, 2H), 6.99 (d, J=8.25 Hz, 2H), 6.67 (d, J=8.80 Hz, 2H), 3.67 (br. s., 1H), 3.63-3.56 (m, 1H), 3.56-3.49 (m, 1H), 3.29 (br. s., 3H), 3.07-2.96 (m, 1H), 2.11-2.20 (m, 2H), 1.99-1.58 (m, 7H), 1.43 (d, J=12.65 Hz, 1H), 1.30-1.12 (m, 2H).

Example 4

1-((1R,2R)-2-((1R,4R,6S)-2-(4-Nitrophenyl)-2-azabicyclo[2.2.1]heptan-6-ylamino)cyclohexyl)-3-(4-(trifluoromethoxy)phenyl)urea

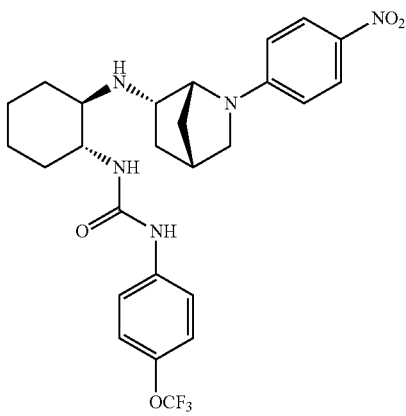 [SMILES: O=C(Nc1ccc(OC(F)(F)F)cc1)N[C@@H]1CCCC[C@H]1N[C@H]1C[C@@H]2C[C@H]1N(c1ccc([N+](=O)[O-])cc1)C2]

A: 2-Benzyl-2-azabicyclo[2.2.1]heptan-6-ol

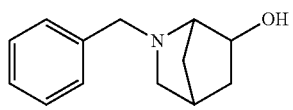 [SMILES: OC1CC2CC1N(Cc1ccccc1)C2]

To a round bottom flask was added 2-benzyl-2-azabicyclo[2.2.1]hept-5-ene (1 g, 5.40 mmol) and THF (7 mL). The reaction was cooled to 0° C. and 1N BH$_3$.THF (10.80 mL, 10.80 mmol) was slowly added to the reaction. The reaction was stirred at 0° C. for 1 hr and then water (0.5 ml) was added to the reaction dropwise to quench the excess BH$_3$. 1N NaOH (5.94 mL, 5.94 mmol) and 30% H$_2$O$_2$ (0.182 mL, 5.94 mmol) were added to the reaction and the reaction was stirred at 40° C. for 1 hr. The reaction was cooled to rt and K$_2$CO$_3$ (1 g) was added. The reaction was diluted with CH$_2$Cl$_2$ (50 ml) and washed with water (2×20 ml) and saturated aqueous NaCl (30 ml). The organic layer was dried over MgSO$_4$, filtered and concentrated. The residue was purified by RP prep-HPLC. The major peak was collected and fractions were concentrated to give 2-benzyl-2-azabicyclo[2.2.1]heptan-6-ol (850 mg, 4.18 mmol, 77% yield). Anal. Calcd. for $C_{13}H_{17}NO$ m/z 203.3, found: 204.1 (M+H)$^+$; $^1$H NMR (500 MHz, CDCl$_3$) δ ppm 7.48-7.32 (m, 5H), 4.47 (d, J=6.60 Hz, 1H), 4.29 (br. s., 1H), 4.23-4.05 (m, 2H), 3.78 (s, 1H), 3.29 (dd, J=11.00, 4.40 Hz, 1H), 2.81-2.72 (m, 1H), 2.68 (br. s., 1H), 2.09 (d, J=11.55 Hz, 1H), 2.04-1.95 (m, 1H), 1.77 (d, J=12.10 Hz, 1H), 1.60-1.50 (m, 1H); $^{13}$C NMR (126 MHz, CDCl$_3$) δ ppm 130.61, 130.04, 129.42, 68.31, 67.72, 59.17, 58.03, 37.98, 35.49, 31.24.

B: 2-Azabicyclo[2.2.1]heptan-6-ol

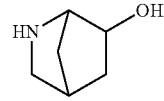

To a hydrogenation bottle was added 2-benzyl-2-azabicyclo[2.2.1]heptan-6-ol (400 mg, 1.968 mmol), MeOH (15 mL), Pd(OH)$_2$ (69.1 mg, 0.492 mmol) and 3 drops of conc. HCl. The reaction was stirred under an atmosphere of hydrogen at 35 psi for 24 hrs. The reaction mixture was filtered through CELITE® and the filtrate was concentrated to give the product, 2-azabicyclo[2.2.1]heptan-6-ol (200 mg, 1.767 mmol, 90% yield) as a clear oil. The product was used in the next step without further purification. Anal. $^1$H NMR (500 MHz, CDCl$_3$) δ ppm 4.35 (br. s., 1H), 3.95 (br. s., 1H), 3.10 (br. s., 1H), 2.88 (br. s., 1H), 2.68 (br. s., 1H), 2.02 (d, J=9.90 Hz, 2H), 1.74 (d, J=10.45 Hz, 1H), 1.58 (d, J=11.55 Hz, 1H).

C: 2-(4-Nitrophenyl)-2-azabicyclo[2.2.1]heptan-6-ol

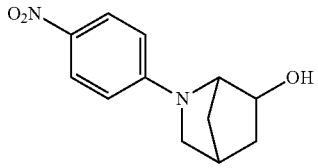 [SMILES: O=[N+]([O-])c1ccc(N2CC3CC(O)C2C3)cc1]

To a round bottom flask was added 2-azabicyclo[2.2.1]heptan-6-ol (150 mg, 1.326 mmol), 1-fluoro-4-nitrobenzene (187 mg, 1.326 mmol), K$_2$CO$_3$ (366 mg, 2.65 mmol) and DMF (5 mL). The reaction was stirred at 65° C. for 4 hrs. The reaction was then diluted with EtOAc (35 ml). The organic solution was washed with water (3×20 ml) and saturated aqueous NaCl (20 ml). The organic layer was dried over MgSO$_4$, filtered and concentrated. The resulting residue was purified using silica gel chromatography (ISCO system) eluting with a gradient of 0-100% EtOAc/Hex to give the product, 2-(4-nitrophenyl)-2-azabicyclo[2.2.1]heptan-6-ol (150 mg, 0.640 mmol, 49% yield), as a yellow solid. Anal. Calcd. for C$_{12}$H$_{14}$N$_2$O$_3$ m/z 234.2, found: 235.2 (M+H)$^+$; $^1$H NMR (500 MHz, CDCl$_3$) δ ppm 8.10 (d, J=9.90 Hz, 2H), 6.49 (d, J=8.25 Hz, 2H), 4.10 (s, 1H), 3.99 (br. s., 1H), 3.39 (dt, J=8.80, 2.75 Hz, 1H), 2.78 (d, J=8.80 Hz, 1H), 2.74 (br. s., 1H), 1.97 (d, J=9.90 Hz, 1H), 1.92 (ddd, J=13.61, 7.01, 2.47 Hz, 1H), 1.78-1.71 (m, 2H), 1.59-1.53 (m, 1H); $^{13}$C NMR (126 MHz, CDCl$_3$) δ ppm 151.32, 136.88, 126.54, 110.27, 71.10, 61.88, 54.11, 40.73, 35.91, 34.23.

D: 2-(4-Nitrophenyl)-2-azabicyclo[2.2.1]heptan-6-one

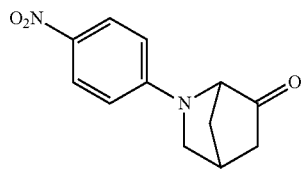 [SMILES: O=C1CC2CC1N(c1ccc([N+](=O)[O-])cc1)C2]

To a round bottom flask was added 2-(4-nitrophenyl)-2-azabicyclo[2.2.1]heptan-6-ol (150 mg, 0.640 mmol), Et$_3$N (0.446 mL, 3.20 mmol) and CH$_2$Cl$_2$ (3 mL). The reaction was cooled to 0° C. Pyridine sulfur trioxide (510 mg, 3.20 mmol) and DMSO (0.909 mL, 12.81 mmol) were mixed in a vial until the solution turned clear and then this clear solution was added to the reaction mixture at 0° C. The reaction was slowly warmed to rt and stirred at rt for 2 hrs. The reaction was diluted with CH$_2$Cl$_2$ (25 ml). The organic solution was washed with water (2×20 ml) and saturated aqueous NaCl (20 ml). The organic layer was dried with MgSO$_4$, filtered and concentrated. The resulting residue was purified using silica gel chromatography (ISCO system) eluting with a gradient of 0-100% EtOAc/Hex to give the product, 2-(4-nitrophenyl)-2-azabicyclo[2.2.1]heptan-6-one, (80 mg, 0.344 mmol, 54% yield) as a yellow solid. Anal. Calcd. for C$_{12}$H$_{12}$N$_2$O$_3$ m/z 232.2, found: 233.2 (M+H)$^+$.

E: (1R,2R)—N1-((6S)-2-(4-Nitrophenyl)-2-azabicyclo[2.2.1]heptan-6-yl)cyclohexane-1,2-diamine

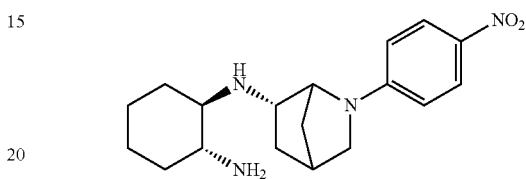

To a round bottom flask was added 2-(4-nitrophenyl)-2-azabicyclo[2.2.1]heptan-6-one (120 mg, 0.517 mmol), CH$_2$Cl$_2$ (3 mL) and Na$_2$SO$_4$ (5 gms). The reaction was purged with argon. Then (1R,2R)-cyclohexane-1,2-diamine (118 mg, 1.033 mmol) and acetic acid (0.592 mL, 10.33 mmol) were added to the reaction. The reaction was stirred at rt for 1 hr. Then sodium triacetoxyborohydride (548 mg, 2.58 mmol) was added to the reaction and the reaction was stirred at rt overnight. The reaction was diluted with CH$_2$Cl$_2$ (50 ml) and filtered. The filtrate was washed with NaOH (0.5N, 30 ml), water (30 ml) and saturated aqueous NaCl (30 ml). The organic layer was dried with MgSO$_4$, filtered and concentrated. The residue was purified by RP prep-HPLC. Two isomers were separated from RP prep-HPLC. The fractions with desired product, which eluted later than the undesired isomer, were concentrated to give (1R,2R)—N1-((6S)-2-(4-nitrophenyl)-2-azabicyclo[2.2.1]heptan-6-yl)cyclohexane-1,2-diamine (80 mg, 0.242 mmol, 46% yield) as a yellow solid. Anal. Calcd. for C$_{18}$H$_{26}$N$_4$O$_2$ m/z 330.4, found: 331.3 (M+H)$^+$.

F: 1-((1R,2R)-2-((1R,4R,6S)-2-(4-Nitrophenyl)-2-azabicyclo[2.2.1]heptan-6-ylamino)cyclohexyl)-3-(4-(trifluoromethoxy)phenyl)urea

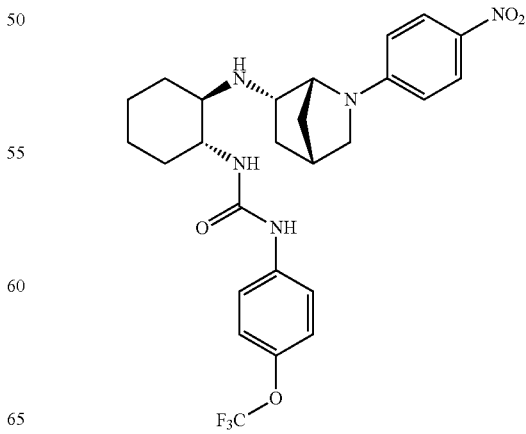

To a round bottom flask was added (1R,2R)—N1-((6S)-2-(4-nitrophenyl)-2-azabicyclo[2.2.1]heptan-6-yl)cyclohexane-1,2-diamine (15 mg, 0.045 mmol), THF (1 mL), Et$_3$N (0.032 mL, 0.227 mmol) and 1-isocyanato-4-(trifluoromethoxy)benzene (4.61 mg, 0.023 mmol). The reaction was stirred at rt for 30 min. After this time, the solvent was removed. The residue was purified by RP prep-HPLC. The product containing fractions were concentrated to give the product, 11-((1R,2R)-2-((1R,4R,6S)-2-(4-nitrophenyl)-2-azabicyclo[2.2.1]heptan-6-ylamino)cyclohexyl)-3-(4-(trifluoromethoxy)phenyl)urea (18 mg, 0.032 mmol, 70.6% yield), as a yellow solid. Anal. Calcd. for C$_{26}$H$_{30}$P$_3$N$_5$O$_4$ m/z 533.5, found: 534.3 (M+H)$^+$; $^1$H NMR (500 MHz, CDCl$_3$) δ ppm 8.61 (br. s., 1H), 7.80 (d, J=9.35 Hz, 2H), 7.26-7.20 (m, 2H), 7.07 (d, J=8.25 Hz, 2H), 6.50 (d, J=8.80 Hz, 3H), 4.63 (br. s., 1H), 3.77 (br. s., 1H), 3.60 (br. s., 1H), 3.30 (s, 2H), 2.91 (br. s., 1H), 2.84 (br. s., 1H), 2.34 (br. s., 1H), 2.08 (br. s., 1H), 1.85-1.61 (m, 5H), 1.59-1.48 (m, 2H), 1.21-1.30 (m, 2H), 1.07 (br. s., 1H). $^{13}$C NMR (126 MHz, CDCl$_3$) δ ppm 158.01, 152.51, 144.32, 137.48, 126.20, 121.57, 119.46, 110.69, 64.18, 59.23, 59.04, 55.57, 52.84, 37.31, 36.92, 32.92, 31.58, 27.96, 23.70, 23.58.

Example 5

Benzyl (1R,2R)-2-((S)-1-(4-nitrophenyl)piperidin-3-ylamino)cyclohexylcarbamate

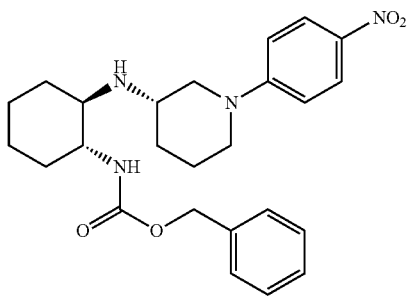 [SMILES: O=C(N[C@@H]1CCCC[C@H]1N[C@H]1CCCN(c2ccc([N+](=O)[O-])cc2)C1)OCc1ccccc1]

Benzyl (1R,2R)-2-((S)-1-(4-nitrophenyl)piperidin-3-ylamino)cyclohexylcarbamate was synthesized using (1R,2R)—N1-(1-(4-nitrophenyl)piperidin-3-yl)cyclohexane-1,2-diamine (from intermediate C, Example 2) (30 mg, 0.094 mmol) and benzyl carbonochloridate (16.07 mg, 0.094 mmol) according to General Procedure G to give 5 mg (12% yield) of the product as a yellow solid. Anal. Calcd. for C$_{25}$H$_{32}$N$_4$O$_4$ m/z 452.5, found: 453.3 (M+H)$^+$; $^1$H NMR (500 MHz, CDCl$_3$) δ ppm 8.08 (d, J=9.3 Hz, 2H), 7.36-7.29 (m, 5H), 6.77 (d, J=9.3 Hz, 2H), 5.05 (br. s., 2H), 4.91 (br. s., 1H), 3.75 (d, J=10.4 Hz, 1H), 3.66 (d, J=12.6 Hz, 1H), 3.31 (d, J=7.7 Hz, 1H), 3.04 (t, J=10.7 Hz, 1H), 2.83 (br. s., 2H), 2.54 (br. s., 1H), 2.15-2.03 (m, 2H), 1.99-1.91 (m, 1H), 1.83 (dd, J=9.1, 4.7 Hz, 2H), 1.79-1.69 (m, 3H), 1.32 (d, J=8.8 Hz, 2H), 1.48 (br. s., 1H), 1.62 (ddd, J=13.9, 10.4, 10.3 Hz, 2H); $^{13}$C NMR (126 MHz, CDCl$_3$) δ ppm 156.63, 154.71, 136.37, 128.52, 128.14, 126.12, 112.77, 66.77, 59.06, 50.93, 47.94, 32.19, 29.68, 24.53, 23.07.

Example 6

Phenyl (1R,2R)-2-((S)-1-(4-nitrophenyl)piperidin-3-ylamino)cyclohexylcarbamate

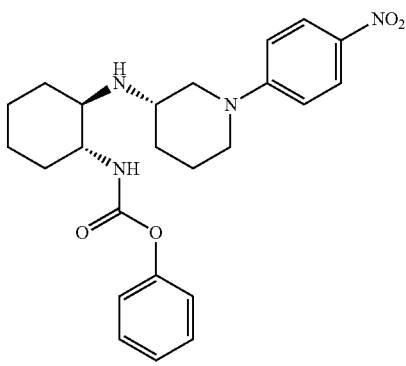 [SMILES: O=C(N[C@@H]1CCCC[C@H]1N[C@H]1CCCN(c2ccc([N+](=O)[O-])cc2)C1)Oc1ccccc1]

Phenyl (1R,2R)-2-((S)-1-(4-nitrophenyl)piperidin-3-ylamino)cyclohexylcarbamate was synthesized using (1R,2R)—N1-(1-(4-nitrophenyl)piperidin-3-yl)cyclohexane-1,2-diamine (from intermediate C, Example 2) (30 mg, 0.094 mmol) and phenyl carbonochloridate (14.75 mg, 0.094 mmol) according to General Procedure G to give 5 mg (10% yield) of the product as a yellow solid. Anal. Calcd. for C$_{24}$H$_{30}$N$_4$O$_4$ m/z 438.5, found: 439.4 (M+H)$^+$; $^1$H NMR (500 MHz, MeOH-d$_3$) δ ppm 8.09 (d, J=9.3 Hz, 2H), 7.26 (t, J=8.0 Hz, 2H), 7.17 (d, J=7.7 Hz, 1H), 7.11-7.05 (m, 2H), 6.90 (d, J=7.7 Hz, 1H), 3.86 (d, J=13.2 Hz, 1H), 3.68-3.55 (m, 3H), 3.47-3.36 (m, 2H), 3.26-3.19 (m, 1H), 2.29 (br. s., 1H), 2.21-2.15 (m, 1H), 2.10 (br. s., 1H), 1.99-1.74 (m, 5H), 1.62-1.36 (m, 4H); $^{13}$C NMR (126 MHz, MeOH-d$_3$) δ ppm 156.21, 140.60, 129.95, 126.33, 126.25, 122.30, 121.96, 115.57, 115.10, 61.27, 54.06, 52.88, 50.25, 49.28, 32.42, 29.24, 28.01, 24.92, 24.37, 22.67.

Example 7

Benzyl (1R,2R)-2-((S)-1-(4-(5-methyl-1,3,4-oxadiazol-2-yl)phenyl)piperidin-3-ylamino)cyclohexylcarbamate

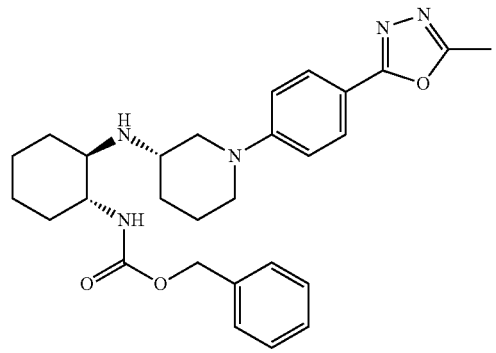 [SMILES: Cc1nnc(-c2ccc(N3CCC[C@H](N[C@@H]4CCCC[C@H]4NC(=O)OCc4ccccc4)C3)cc2)o1]

A: 1-(4-(5-Methyl-1,3,4-oxadiazol-2-yl)phenyl)piperidin-3-ol

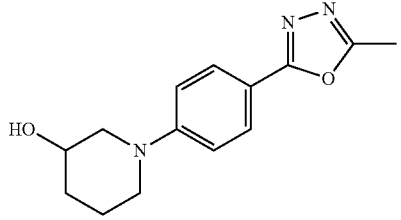 [SMILES: Cc1nnc(-c2ccc(N3CCCC(O)C3)cc2)o1]

1-(4-(5-Methyl-1,3,4-oxadiazol-2-yl)phenyl)piperidin-3-ol (120 mg, 0.463 mmol, 37% yield) was synthesized as described in General Procedure B using 2-(4-bromophenyl)-5-methyl-1,3,4-oxadiazole (300 mg, 1.255 mmol) and piperidin-3-ol (254 mg, 2.51 mmol). Anal. Calcd. for $C_{14}H_{17}N_3O_2$ m/z 259.3, found: 260.0 (M+H)$^+$.

B: tert-Butyl (1R,2R)-2-(1-(4-(5-methyl-1,3,4-oxadiazol-2-yl)phenyl)piperidin-3-ylamino)cyclohexylcarbamate

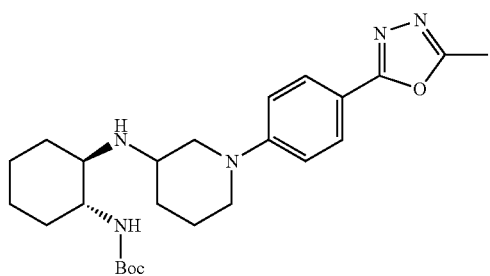 [SMILES: Cc1nnc(-c2ccc(N3CCCC(N[C@@H]4CCCC[C@H]4NC(=O)OC(C)(C)C)C3)cc2)o1]

1-(4-(5-Methyl-1,3,4-oxadiazol-2-yl)phenyl)piperidin-3-ol was converted to the corresponding ketone using the procedure described in General Procedure D. Then the corresponding ketone was reacted according to the procedure described in General Procedure F to give the desired product, tert-butyl (1R,2R)-2-(1-(4-(5-methyl-1,3,4-oxadiazol-2-yl)phenyl)piperidin-3-ylamino)cyclohexylcarbamate (300 mg, 0.658 mmol). Anal. Calcd. for $C_{25}H_{37}N_5O_3$ m/z 455.6, found: 456.3 (M+H)$^+$.

C: (1R,2R)—N1-(1-(4-(5-Methyl-1,3,4-oxadiazol-2-yl)phenyl)piperidin-3-yl)cyclohexane-1,2-diamine

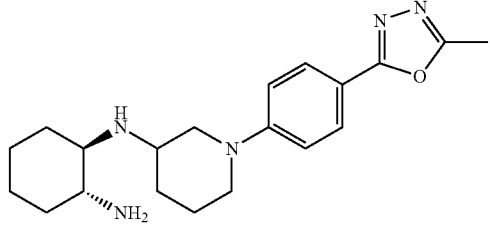 [SMILES: Cc1nnc(-c2ccc(N3CCCC(N[C@@H]4CCCC[C@H]4N)C3)cc2)o1]

(1R,2R)—N1-(1-(4-(5-Methyl-1,3,4-oxadiazol-2-yl)phenyl)piperidin-3-yl)cyclohexane-1,2-diamine bis-trifluoroacetate (400 mg, 0.685 mmol) was synthesized in 100% yield using General Procedure J using tert-butyl (1R,2R)-2-(1-(4-(5-methyl-1,3,4-oxadiazol-2-yl)phenyl)piperidin-3-ylamino)cyclohexylcarbamate (300 mg, 0.685 mmol).

D: Benzyl (1R,2R)-2-((S)-1-(4-(5-methyl-1,3,4-oxadiazol-2-yl)phenyl)piperidin-3-ylamino)cyclohexylcarbamate

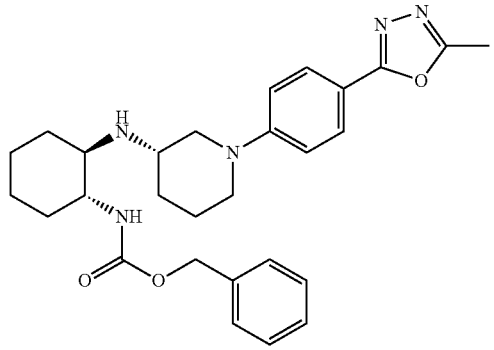 [SMILES: Cc1nnc(-c2ccc(N3CCC[C@H](N[C@@H]4CCCC[C@H]4NC(=O)OCc4ccccc4)C3)cc2)o1]

To a solution of (1R,2R)—N1-(1-(4-(5-methyl-1,3,4-oxadiazol-2-yl)phenyl)piperidin-3-yl)cyclohexane-1,2-diamine bis-trifluoroacetate (35 mg, 0.060 mmol) in MeOH (1 mL) at rt was added benzyl 2,5-dioxopyrrolidin-1-yl carbonate (17.94 mg, 0.072 mmol), followed by diisopropyl ethyl amine (0.037 mL, 0.210 mmol). The reaction was stirred at rt for 5 min. After this time, HPLC/LC/MS showed the desired product formed. The reaction was concentrate and then diluted with EtOAc (20 ml). The organic solution was washed with water (20 ml). The organic layers were concentrated under reduced pressure. The resulting residue was purified by RP prep-HPLC to give the desired product benzyl (1R,2R)-2-((S)-1-(4-(5-methyl-1,3,4-oxadiazol-2-yl)phenyl)piperidin-3-ylamino)cyclohexylcarbamate trifluoroacetate (8 mg, 0.013 mmol, 30% yield) as an off-white solid. Anal. Calcd. for $C_{28}H_{35}N_5O_3$ m/z 489.6, found: 490.4 (M+H)$^+$; $^1$H NMR (400 MHz, CDCl$_3$) δ ppm 7.85 (d, J=8.79 Hz, 2H), 7.22 (br. s., 3H), 7.16 (d, J=2.75 Hz, 2H), 6.96 (d, J=8.79 Hz, 2H), 5.91 (d, J=5.50 Hz, 1H), 4.78 (br. s., 2H), 3.62-3.39 (m, 4H), 3.36-3.16 (m, 3H), 2.59 (s, 3H), 2.29-2.17 (m, 1H), 2.04-1.83 (m, 5H), 1.83-1.61 (m, 3H), 1.43-1.16 (m, 2H).

Example 8

Benzyl (1R,2R)-2-((S)-1-(4-(1H-pyrazol-1-yl)phenyl)piperidin-3-ylamino)cyclohexylcarbamate

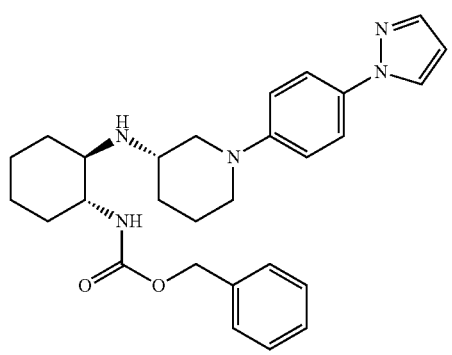 [SMILES: O=C(N[C@@H]1CCCC[C@H]1N[C@H]1CCCN(c2ccc(-n3cccn3)cc2)C1)OCc1ccccc1]

A: 1-(4-(1H-Pyrazol-1-yl)phenyl)piperidin-3-one

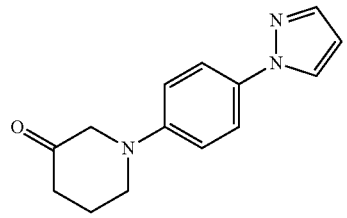 [SMILES: O=C1CCCN(c2ccc(-n3cccn3)cc2)C1]

1-(4-Bromophenyl)-1H-pyrazole was reacted with piperidin-3-ol to give corresponding alcohol using the procedure described in General Procedure B. The corresponding alcohol was oxidized to ketone according to the procedure described in General Procedure D to give desired product, 1-(4-(1H-pyrazol-1-yl)phenyl)piperidin-3-one (300 mg, 1.243 mmol).

B: tert-Butyl (1R,2R)-2-((S)-1-(4-(1H-pyrazol-1-yl)phenyl)piperidin-3-ylamino)cyclohexylcarbamate

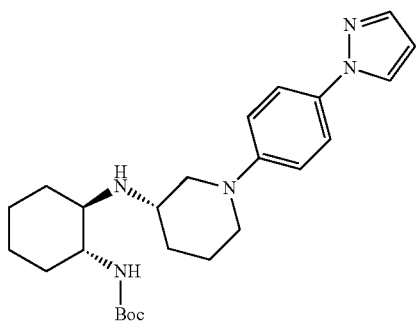 [SMILES: CC(C)(C)OC(=O)N[C@@H]1CCCC[C@H]1N[C@H]1CCCN(c2ccc(-n3cccn3)cc2)C1]

tert-Butyl (1R,2R)-2-((S)-1-(4-(1H-pyrazol-1-yl)phenyl)piperidin-3-ylamino)cyclohexylcarbamate (172 mg, 0.391 mmol) was synthesized according to the General Procedure F. During the ISCO purification, two diastereomers were separated and the desired product was collected.

C: (1R,2R)—N1-((S)-1-(4-(1H-Pyrazol-1-yl)phenyl)piperidin-3-yl)cyclohexane-1,2-diamine

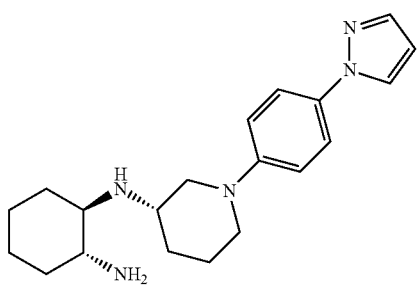 [SMILES: N[C@@H]1CCCC[C@H]1N[C@H]1CCCN(c2ccc(-n3cccn3)cc2)C1]

(1R,2R)—N1-((S)-1-(4-(1H-Pyrazol-1-yl)phenyl)piperidin-3-yl)cyclohexane-1,2-diamine bis-trifluoroacetate (220 mg, 0.388 mmol, 100% yield) was synthesized according to the General Procedure J using tert-butyl (1R,2R)-2-((S)-1-(4-(1H-pyrazol-1-yl)phenyl)piperidin-3-ylamino)cyclohexyl-carbamate (170 mg, 0.388 mmol). Anal. Calcd. for $C_{20}H_{29}N_5$ m/z 339.4, found: 340.3 $(M+H)^+$.

D: Benzyl (1R,2R)-2-((S)-1-(4-(1H-pyrazol-1-yl)phenyl)piperidin-3-ylamino)cyclohexylcarbamate

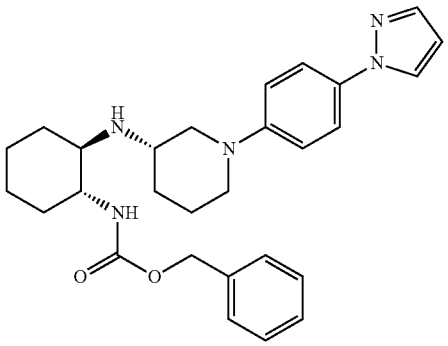 [SMILES: O=C(N[C@@H]1CCCC[C@H]1N[C@H]1CCCN(c2ccc(-n3cccn3)cc2)C1)OCc1ccccc1]

To a solution of (1R,2R)—N1-((S)-1-(4-(1H-pyrazol-1-yl)phenyl)piperidin-3-yl)cyclohexane-1,2-diamine bis-trifluoroacetate (32 mg, 0.056 mmol) in MeOH (1 mL) at rt was added benzyl 2,5-dioxopyrrolidin-1-yl carbonate (16.86 mg, 0.068 mmol), followed by diisopropyl ethyl amine (0.034 mL, 0.197 mmol). The reaction was stirred at rt for 5 min. After this time, HPLC and LC/MS showed the desired product had formed. The reaction was concentrated and diluted with EtOAc (20 ml). The EtOAc solution was washed with water (20 ml). The organic extracts were concentrated under reduced pressure. The resulting residue was purified by RP prep-HPLC to give the desired product benzyl (1R,2R)-2-((S)-1-(4-(1H-pyrazol-1-yl)phenyl)piperidin-3-ylamino)cyclohexylcarbamate trifluoroacetate (12 mg, 0.020 mmol, 36% yield) as a beige oil. Anal. Calcd. for $C_{28}H_{35}N_5O_2$ m/z 473.5, found: 474.5 $(M+H)^+$; $^1H$ NMR (400 MHz, $CDCl_3$) δ ppm 7.72 (s, 2H), 7.53 (d, J=8.79 Hz, 2H), 7.23 (d, J=2.75 Hz, 3H), 7.15 (br. s., 2H), 7.06 (d, J=8.79 Hz, 2H), 6.45 (s, 1H), 5.76 (br. s., 1H), 4.87-4.48 (m, 2H), 3.70-3.34 (m, 4H), 3.32-3.15 (m, 2H), 3.02 (d, J=8.79 Hz, 1H), 2.21 (d, J=10.99 Hz, 1H), 2.16-2.04 (m, 1H), 2.01-1.61 (m, 7H), 1.45-1.12 (m, 2H).

Example 9

Benzyl (1R,2R)-2-((S)-1-(4-cyanophenyl)piperidin-3-ylamino)cyclohexylcarbamate

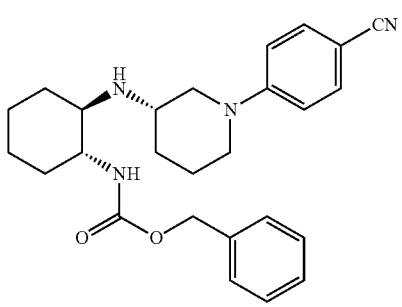 [SMILES: N#Cc1ccc(N2CCC[C@H](N[C@@H]3CCCC[C@H]3NC(=O)OCc3ccccc3)C2)cc1]

Benzyl (1R,2R)-2-((S)-1-(4-cyanophenyl)piperidin-3-ylamino)cyclohexyl-carbamate (6 mg, 0.013 mmol) was synthesized as described in Example 5 using 4-((S)-3-((1R,2R)-2-aminocyclohexylamino)piperidin-1-yl)benzonitrile (from intermediate D, Example 10). Anal. Calcd. for $C_{26}H_{32}N_4O_2$ m/z 432.5, found: 433.4 (M+H)$^+$; $^1$H NMR (500 MHz, MeOH-d$_3$) δ ppm 7.55-7.48 (m, 2H), 7.32-7.25 (m, 3H), 7.20-7.13 (m, 2H), 7.10-7.04 (m, 2H), 5.01-4.93 (m, 1H), 4.72-4.65 (m, 1H), 3.64-3.58 (m, 1H), 3.56-3.49 (m, 2H), 3.47-3.39 (m, 1H), 3.27-3.20 (m, 2H), 2.30-2.23 (m, 1H), 2.09-1.98 (m, 2H), 1.94-1.78 (m, 5H), 1.56-1.30 (m, 5H); $^{13}$C NMR (126 MHz, MeOH-d$_3$) δ ppm 134.31, 129.16, 128.98, 128.71, 117.25, 68.11, 62.59, 54.88, 53.83, 52.60, 50.19, 32.03, 27.85, 24.92, 24.33, 21.82.

Example 10

N-((1R,2R)-2-((S)-1-(4-Cyanophenyl)piperidin-3-ylamino)cyclohexyl)-2-(1-methyl-1H-indol-3-yl)acetamide

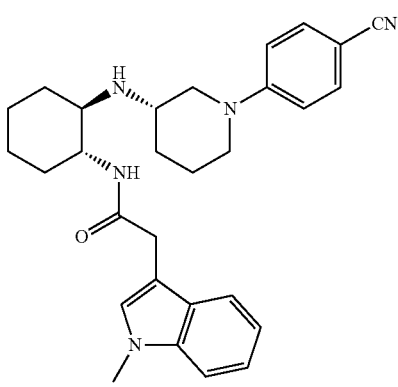 [SMILES: Cn1cc(CC(=O)N[C@@H]2CCCC[C@H]2N[C@H]2CCCN(c3ccc(C#N)cc3)C2)c2ccccc21]

A: 4-(3-Hydroxypiperidin-1-yl)benzonitrile

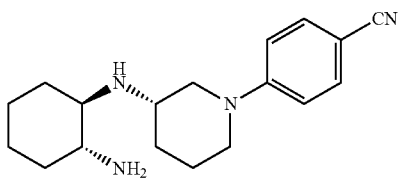

4-(3-Hydroxypiperidin-1-yl)benzonitrile (7.27 gm, 35.9 mmol) was synthesized in 75% yield using the procedures described in General Procedure A using 4-fluorobenzonitrile (5.82 gm, 48.0 mmol). Anal. Calcd. for $C_{12}H_{14}N_2O$ m/z 202.2, found: 203.2 (M+H)$^+$; $^1$H NMR (500 MHz, CDCl$_3$) δ ppm 7.48 (d, J=9.35 Hz, 2H), 6.88 (d, J=8.80 Hz, 2H), 3.89 (br. s., 1H), 3.60 (dd, J=12.65, 3.30 Hz, 1H), 3.40 (ddd, J=12.78, 6.46, 3.30 Hz, 1H), 3.24-3.02 (m, 2H), 2.01-1.84 (m, 3H), 1.73-1.56 (m, 2H); $^{13}$C NMR (126 MHz, CDCl$_3$) δ ppm 153.68, 133.50, 120.01, 114.69, 100.03, 66.12, 54.84, 47.74, 32.51, 21.88.

B: 4-(3-Oxopiperidin-1-yl)benzonitrile

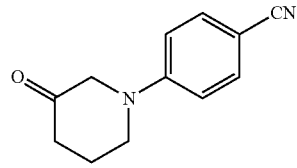 [SMILES: N#Cc1ccc(N2CCCC(=O)C2)cc1]

4-(3-Oxopiperidin-1-yl)benzonitrile (3.3 gm, 16.48 mmol) was synthesized in 95% yield as described in General Procedure D using 4-(3-hydroxypiperidin-1-yl)benzonitrile (3.5 gm, 17.31 mmol). Anal. Calcd. for $C_{12}H_{12}N_2O$ m/z 200.2, found: 201.2 (M+H)$^+$; $^1$H NMR (500 MHz, CDCl$_3$) δ ppm 7.53 (d, J=8.80 Hz, 2H), 6.79 (d, J=8.80 Hz, 2H), 3.96 (s, 2H), 3.58 (t, J=6.05 Hz, 2H), 2.58 (t, J=6.87 Hz, 2H), 2.18 (t, J=6.32 Hz, 2H); $^{13}$C NMR (126 MHz, CDCl$_3$) δ ppm 205.32, 151.52, 133.66, 119.89, 112.91, 100.25, 56.25, 45.66, 38.13, 21.78.

C: 4-(3-((1R,2R)-2-Aminocyclohexylamino)piperidin-1-yl)benzonitrile

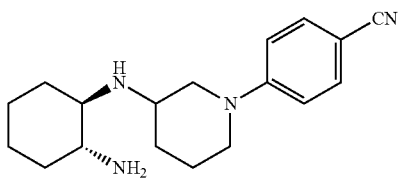 [SMILES: N#Cc1ccc(N2CCCC(N[C@@H]3CCCC[C@H]3N)C2)cc1]

4-(3-((1R,2R)-2-Aminocyclohexylamino)piperidin-1-yl)benzonitrile (360 mg, 1.21 mmol) was synthesized in 38% yield using the procedures as described in General Procedure E using 4-(3-oxopiperidin-1-yl)benzonitrile (640 mg, 3.20 mmol). Anal. Calcd. for $C_{18}H_{26}N_4$ m/z 298.4, found: 299.3 (M+H)$^+$; $^1$H NMR (500 MHz, MeOH-d$_3$) δ ppm 7.61-7.44 (m, 2H), 7.03 (d, J=9.35 Hz, 2H), 4.02-3.86 (m, 1H), 3.85-3.74 (m, 1H), 3.05-2.83 (m, 3H), 2.82-2.62 (m, 1H), 2.27 (d, J=14.30 Hz, 1H), 2.13 (d, J=12.10 Hz, 1H), 2.02 (s, 1H), 1.92-1.78 (m, 3H), 1.76-1.62 (m, 1H), 1.34-1.56 (m, 4H), 1.21-1.34 (m, 2H).

D: 4-((S)-3-((1R,2R)-2-Aminocyclohexylamino)piperidin-1-yl)benzonitrile 4-((S)-3-((1R,2R)-2-Aminocyclohexylamino)piperidin-1-yl)benzonitrile was separated from 4-((R)-3-((1R,2R)-2-Aminocyclohexylamino)piperidin-1-yl)benzonitrile using chiral separation method D.

E: N-((1R,2R)-2-((S)-1-(4-Cyanophenyl)piperidin-3-ylamino)cyclohexyl)-2-(1-methyl-1H-indol-3-yl)acetamide

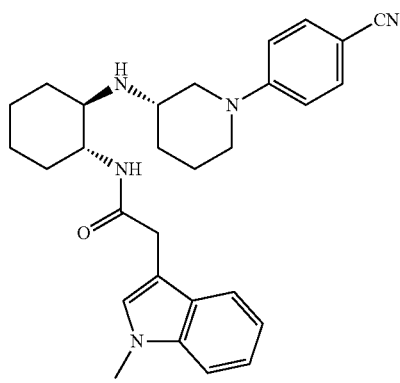 [SMILES: Cn1cc(CC(=O)N[C@@H]2CCCC[C@H]2N[C@H]2CCCN(c3ccc(C#N)cc3)C2)c2ccccc21]

N-((1R,2R)-2-((S)-1-(4-Cyanophenyl)piperidin-3-ylamino)cyclohexyl)-2-(1-methyl-1H-indol-3-yl)acetamide (15 mg, 0.031 mmol) was synthesized in 32% yield using the procedures described in General Procedure I using 4-(3-((1R, 2R)-2-aminocyclohexylamino)piperidin-1-yl)benzonitrile (30 mg, 0.10 mmol) and 2-(1-methyl-1H-indol-3-yl)acetic acid (19.02 mg, 0.10 mmol). Anal. Calcd. for $C_{29}H_{35}N_5O$ m/z 469.6, found: 470.3 $(M+H)^+$; $^1H$ NMR (500 MHz, MeOH-$d_3$) δ ppm 7.61-7.47 (m, 3H), 7.23 (d, J=8.25 Hz, 1H), 7.14 (t, J=7.70 Hz, 1H), 7.07-6.97 (m, 2H), 6.89 (d, J=8.80 Hz, 2H), 3.80 (dd, J=11.00, 6.60 Hz, 1H), 3.58 (s, 3H), 3.48 (s, 2H), 3.28-3.11 (m, 4H), 3.00-2.91 (m, 1H), 2.87 (dd, J=13.20, 7.15 Hz, 1H), 2.19 (d, J=13.75 Hz, 1H), 2.05-1.92 (m, 2H), 1.90-1.71 (m, 3H), 1.67-1.49 (m, 4H), 1.44-1.34 (m, 2H).

Example 11

1-((1R,2R)-2-((S)-1-(4-Cyanophenyl)piperidin-3-ylamino)cyclohexyl)-3-phenylurea

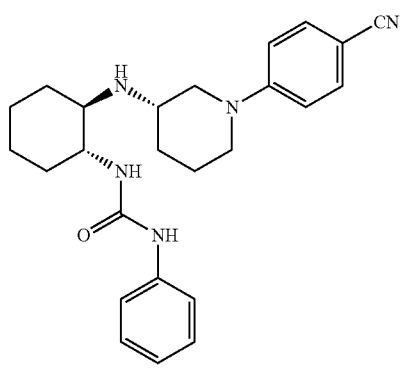 [SMILES: N#Cc1ccc(N2CCC[C@H](N[C@@H]3CCCC[C@H]3NC(=O)Nc3ccccc3)C2)cc1]

1-((1R,2R)-2-((S)-1-(4-Cyanophenyl)piperidin-3-ylamino)cyclohexyl)-3-phenylurea (8 mg, 0.016 mmol), was synthesized in 17% yield using the procedures described in Example 1 using 4-fluorobenzonitrile (12.63 mg, 0.104 mmol) in step D. Anal. Calcd. for $C_{25}H_{31}N_5O$ m/z 417.5, found: 418.3 $(M+H)^+$; $^1H$ NMR (500 MHz, MeOH-$d_3$) δ ppm 7.23-7.15 (m, 6H), 6.99 (t, J=6.9 Hz, 1H), 6.86 (d, J=8.8 Hz, 2H), 3.85 (dd, J=13.7, 4.9 Hz, 1H), 3.63-3.46 (m, 3H), 3.26-3.14 (m, 2H), 3.00 (ddd, J=12.5, 9.5, 3.3 Hz, 1H), 2.27 (d, J=14.3 Hz, 1H), 2.12-1.79 (m, 7H), 1.62-1.44 (m, 2H), 1.40 (t, J=10.2 Hz, 2H); $^{13}C$ NMR (126 MHz, MeOH-$d_3$) δ ppm 159.27, 154.60, 133.91, 129.46, 123.50, 121.88, 120.14, 119.05, 116.56, 102.10, 64.17, 53.33, 52.92, 32.03, 29.30, 27.69, 25.00, 24.31, 21.16.

Example 12

Benzyl (1R,2R)-2-((S)-1-(4-(trifluoromethyl)phenyl)piperidin-3-ylamino)cyclohexylcarbamate

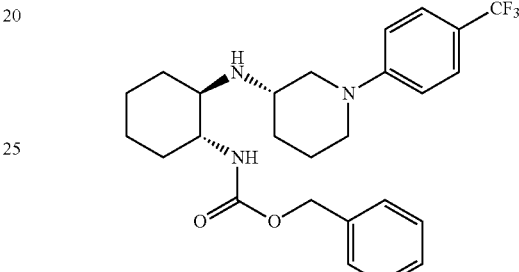

A: 1-(4-(Trifluoromethyl)phenyl)piperidin-3-ol

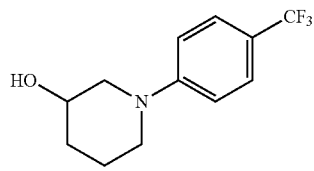 [SMILES: OC1CCCN(c2ccc(C(F)(F)F)cc2)C1]

1-(4-(Trifluoromethyl)phenyl)piperidin-3-ol (760 mg, 3.10 mmol) was synthesized in, 70% yield using the procedures described in General Procedure B using 1-bromo-4-(trifluoromethyl)benzene (1 gm, 4.44 mmol).

B: 1-(4-(Trifluoromethyl)phenyl)piperidin-3-one

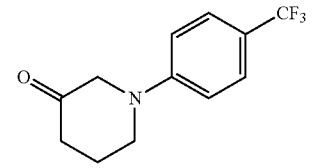 [SMILES: O=C1CCCN(c2ccc(C(F)(F)F)cc2)C1]

1-(4-(Trifluoromethyl)phenyl)piperidin-3-one (240 mg, 0.987 mmol) was synthesized in, 60% yield using the procedures described in General Procedure D. Anal. Calcd. for $C_{12}H_{12}F_3NO$ m/z 243.3, found: 244.1 $(M+H)^+$.

C: tert-Butyl (1R,2R)-2-((S)-1-(4-(trifluoromethyl)phenyl)piperidin-3-ylamino)cyclohexylcarbamate

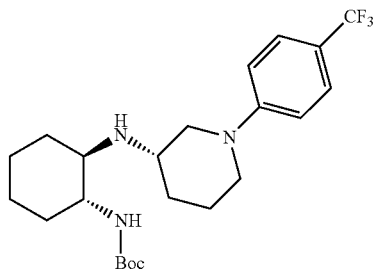 [SMILES: CC(C)(C)OC(=O)N[C@@H]1CCCC[C@H]1N[C@H]1CCCN(c2ccc(C(F)(F)F)cc2)C1]

tert-Butyl (1R,2R)-2-((S)-1-(4-(trifluoromethyl)phenyl)piperidin-3-ylamino)cyclohexylcarbamate (31 mg, 0.070 mmol, 17% yield) was synthesized as described in General Procedure F using 1-(4-(trifluoromethyl)phenyl)piperidin-3-one (100 mg, 0.441 mmol). During the ISCO purification, two diastereomers were separated and the desired product was collected. $^1$H NMR (400 MHz, CDCl$_3$) δ ppm 7.46 (d, J=8.8 Hz, 2H), 6.92 (d, J=8.7 Hz, 2H), 4.49 (d, J=6.7 Hz, 1H), 3.65 (d, J=11.4 Hz, 1H), 3.58-3.48 (m, 1H), 3.27-3.14 (m, 1H), 2.94-2.84 (m, 1H), 2.84-2.73 (m, 1H), 2.70-2.60 (m, 1H), 2.39-2.29 (m, 1H), 2.14-1.96 (m, 2H), 1.94-1.86 (m, 1H), 1.85-1.76 (m, 1H), 1.74-1.63 (m, 2H), 1.61-1.52 (m, 1H), 1.42 (s, 9H), 1.36-1.07 (m, 4H).

D: (1R,2R)—N1-((S)-1-(4-(Trifluoromethyl)phenyl)piperidin-3-yl)cyclohexane-1,2-diamine bis-trifluoroacetate

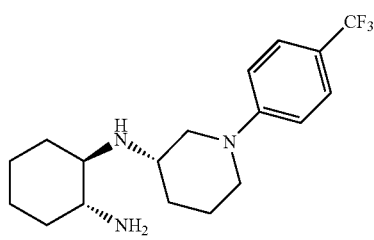 [SMILES: N[C@@H]1CCCC[C@H]1N[C@H]1CCCN(c2ccc(C(F)(F)F)cc2)C1]

(1R,2R)—N1-((S)-1-(4-(Trifluoromethyl)phenyl)piperidin-3-yl)cyclohexane-1,2-diamine bis-trifluoroacetate (39 mg, 0.068 mmol) was synthesized in, 100% yield using the procedures described in General Procedure J from tert-Butyl (1R,2R)-2-((S)-1-(4-(trifluoromethyl)phenyl)piperidin-3-ylamino)cyclohexylcarbamate (30 mg, 0.068 mmol).

E: Benzyl (1R,2R)-2-((S)-1-(4-(trifluoromethyl)phenyl)piperidin-3-ylamino)cyclohexylcarbamate

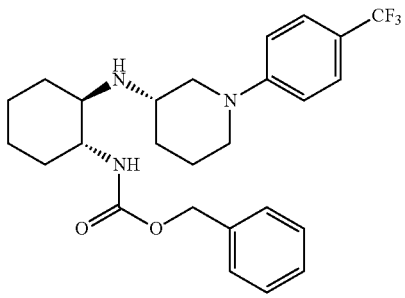

To a solution of (1R,2R)—N1-((S)-1-(4-(trifluoromethyl)phenyl)piperidin-3-yl)cyclohexane-1,2-diamine bis-trifluoroacetate (19.36 mg, 0.034 mmol) in MeOH (1 mL) at rt was added benzyl 2,5-dioxopyrrolidin-1-yl carbonate (10.17 mg, 0.041 mmol) followed by diisopropyl ethyl amine (0.034 mL, 0.193 mmol). The reaction was stirred at rt for 5 min. After this time, HPLC and LC/MS showed the desired product formed. The reaction was concentrated and the residue was diluted with EtOAc (20 ml). The organic layer was washed with water (20 ml). The organic extracts were concentrated under vacuum. The resulting residue was purified by RP prep-HPLC to give the desired product benzyl (1R,2R)-2-((S)-1-(4-(trifluoromethyl)phenyl)piperidin-3-ylamino)cyclohexylcarbamate trifluoroacetate (8 mg, 0.013 mmol, 39.5% yield) as a beige oil. Anal. Calcd. for C$_{26}$H$_{32}$F$_3$N$_3$O$_2$ m/z 475.5, found: 476.2 (M+H)$^+$; $^1$H NMR (400 MHz, CDCl$_3$) δ ppm 7.49 (d, J=8.5 Hz, 2H), 7.34-7.21 (m, 3H), 7.20-7.11 (m, 2H), 6.96 (d, J=8.4 Hz, 2H), 5.68 (s, 1H), 4.72 (dd, J=38.5, 12.3 Hz, 2H), 3.65-3.37 (m, 3H), 3.36-3.28 (m, 2H), 3.26-3.07 (m, 2H), 2.20 (d, J=11.2 Hz, 1H), 2.14-1.99 (m, 1H), 1.99-1.84 (m, 4H), 1.83-1.57 (m, 4H), 1.44-1.18 (m, 2H).

Example 13

N-((1R,2R)-2-((S)-1-(4-Cyanophenyl)piperidin-3-ylamino)cyclohexyl)-3-o-tolylpropanamide

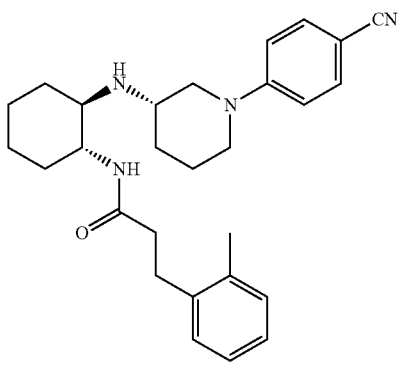 [SMILES: Cc1ccccc1CCC(=O)N[C@@H]1CCCC[C@H]1N[C@H]1CCCN(c2ccc(C#N)cc2)C1]

N-((1R,2R)-2-((S)-1-(4-Cyanophenyl)piperidin-3-ylamino)cyclohexyl)-3-O—tolylpropanamide (18 mg, 0.038 mmol) was synthesized in 38% yield using the procedures as described in Example 10 using 3-o-tolylpropanoic acid (16.51 mg, 0.101 mmol) in step D. Anal. Calcd. for C$_{28}$H$_{36}$N$_4$O m/z 444.5, found: 445.3 (M+H)$^+$; $^1$H NMR (400 MHz, MeOH-d$_3$) δ ppm 7.51 (d, J=8.79 Hz, 2H), 7.15-6.95 (m, 5H), 6.91-6.87 (m, 1H), 3.74-3.39 (m, 4H), 3.19 (td, J=10.99, 3.95 Hz, 1H), 3.14-3.04 (m, 1H), 2.77-2.64 (m, 1H), 2.56 (ddd, J=14.50, 9.01, 5.93 Hz, 1H), 2.31-2.18 (m, 2H), 2.19-2.12 (m, 3H), 2.07-1.70 (m, 8H), 1.58-1.16 (m, 5H).

Example 14

1-((1R,2R)-2-((S)-1-(5-Nitropyrimidin-2-yl)piperidin-3-ylamino)cyclohexyl)-3-phenylurea

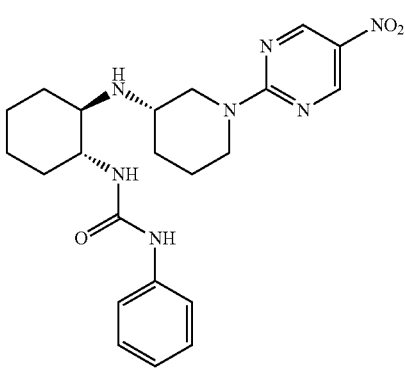 [SMILES: O=C(Nc1ccccc1)N[C@@H]1CCCC[C@H]1N[C@H]1CCCN(c2ncc([N+](=O)[O-])cn2)C1]

A: 1-(5-Nitropyrimidin-2-yl)piperidin-3-ol

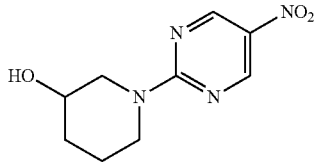 [SMILES: O=[N+]([O-])c1cnc(N2CCCC(O)C2)nc1]

To a stirring solution of piperidin-3-ol (0.333 g, 3.29 mmol) and 2-chloro-5-nitropyrimidine (0.500 g, 3.13 mmol) in DMF (8 mL) was added $K_2CO_3$ (1.04 g, 7.52 mmol). The resulting yellowish suspension was stirred at 70° C. for 1.5 h. After this time, LC/MC showed the reaction was complete. The reaction mixture was allowed to cool to rt, then partitioned between water and EtOAc. The separated aqueous phase was extracted with EtOAc (2×). The combined EtOAc extracts were washed with water (1×), saturated aqueous NaCl (2×). The organic layer was dried over $Na_2SO_4$, filtered and concentrated. The residue was dried in vacuum for 30 min to afford the desired product 1-(5-nitropyrimidin-2-yl)piperidin-3-ol (536 mg, 2.391 mmol, 76% yield) as a yellow solid. Anal. Calcd. for $C_9H_{12}N_4O_3$ m/z 224.2, found: 225.1 $(M+H)^+$; $^1H$ NMR (400 MHz, $CDCl_3$) δ ppm 9.17-8.91 (m, 2H), 4.20 (dd, J=13.14, 3.03 Hz, 1H), 4.03 (ddd, J=13.07, 7.14, 3.79 Hz, 1H), 3.96-3.74 (m, 2H), 2.95 (s, 1H), 2.11-1.87 (m, 2H), 1.81-1.50 (m, 3H).

B: 1-(5-Nitropyrimidin-2-yl)piperidin-3-one

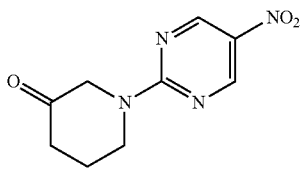 [SMILES: O=C1CCCN(c2ncc([N+](=O)[O-])cn2)C1]

1-(5-Nitropyrimidin-2-yl)piperidin-3-one (260 mg, 1.179 mmol, 50.5% yield) was synthesized as described in General Procedure D. Anal. Calcd. for $C_9H_{10}N_4O_3$ m/z 222.2, found: 223.0 $(M+H)^+$; $^1H$ NMR (400 MHz, $CDCl_3$) δ ppm 9.11 (d, J=4.95 Hz, 2H), 4.56 (s, 2H), 4.17-4.02 (m, 2H), 2.60 (t, J=6.60 Hz, 2H), 2.26-2.06 (m, 2H).

C: tert-Butyl (1R,2R)-2-((S)-1-(5-nitropyrimidin-2-yl)piperidin-3-ylamino)cyclohexylcarbamate

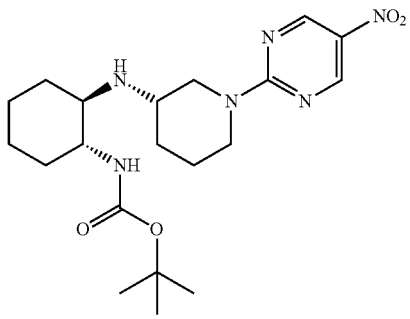

tert-Butyl (1R,2R)-2-((S)-1-(5-nitropyrimidin-2-yl)piperidin-3-ylamino)cyclohexylcarbamate (95 mg, 0.226 mmol) was synthesized according to General Procedure F. During the ISCO purification, two diastereomers were separated and the desired product was collected. Anal. Calcd. for $C_{20}H_2N_6O_4$ m/z 420.5, found: 421.3 $(M+H)^+$; $^1H$ NMR (400 MHz, $CDCl_3$) δ ppm 9.05 (s, 2H), 5.24-5.17 (m, 1H), 4.92-4.75 (m, 1H), 4.58-4.44 (m, 1H), 3.88-3.74 (m, 1H), 3.66-3.53 (m, 1H), 3.48-3.40 (m, 1H), 3.33-3.16 (m, 2H), 2.26-2.11 (m, 2H), 2.06-1.86 (m, 3H), 1.85-1.77 (m, 1H), 1.72-1.48 (m, 2H), 1.41 (s, 9H), 1.36-1.21 (m, 2H).

D: (1R,2R)—N1-((S)-1-(5-Nitropyrimidin-2-yl)piperidin-3-yl)cyclohexane-1,2-diamine

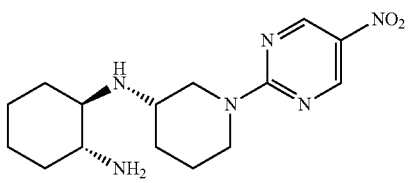

(1R,2R)—N1-((S)-1-(5-Nitropyrimidin-2-yl)piperidin-3-yl)cyclohexane-1,2-diamine bis-trifluoroacetate (220 mg, 0.388 mmol, 100% yield) was synthesized according to the General Procedure J using tert-butyl (1R,2R)-2-((S)-1-(4-(1H-pyrazol-1-yl)phenyl)piperidin-3-ylamino)cyclohexylcarbamate (149 mg, 0.272 mmol). Anal. Calcd. for $C_{15}H_{24}N_6O_2$ m/z 320.3, found: 321.1 $(M+H)^+$.

E: 1-((1R,2R)-2-((S)-1-(5-Nitropyrimidin-2-yl)piperidin-3-ylamino)cyclohexyl)-3-phenylurea

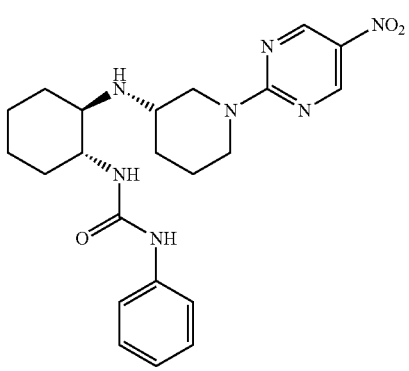

1-((1R,2R)-2-((S)-1-(5-Nitropyrimidin-2-yl)piperidin-3-ylamino)cyclohexyl)-3-phenylurea (17.5 mg, 0.031 mmol, 51.5% yield) was synthesized as described in General Procedure F using phenyl isocyanate (7.15 mg, 0.060 mmol) and (1R,2R)—N1-((S)-1-(5-nitropyrimidin-2-yl)piperidin-3-yl)cyclohexane-1,2-diamine (32.9 mg, 0.060 mmol). Anal. Calcd. for $C_{22}H_{29}N_7O_3$ m/z 439.5, found: 440.4 $(M+H)^+$; $^1H$ NMR (400 MHz, $CDCl_3$) δ ppm 10.25 (br. s., 1H), 8.90 (d, J=6.60 Hz, 1H), 8.78-8.59 (m, 2H), 7.23-7.123 (m, 4H), 6.98 (t, J=6.87 Hz, 1H), 6.56 (br. s., 1H), 4.27 (d, J=12.09 Hz, 1H), 4.12-3.92 (m, 2H), 3.88-3.73 (m, 1H), 3.64 (br. s., 1H), 3.21 (br. s., 1H), 3.02-2.77 (m, 3H), 2.20-2.00 (m, 2H), 1.92 (ddd, J=7.01, 3.44, 3.30 Hz, 1H), 1.80 (d, J=10.99 Hz, 2H), 1.63 (d, J=14.29 Hz, 3H), 1.35-1.11 (m, 2H).

Example 15

1-((1R,2R)-2-(1-(4-(Oxazol-2-yl)phenyl)piperidin-3-ylamino)cyclohexyl)-3-(4-(trifluoromethoxy)phenyl)urea

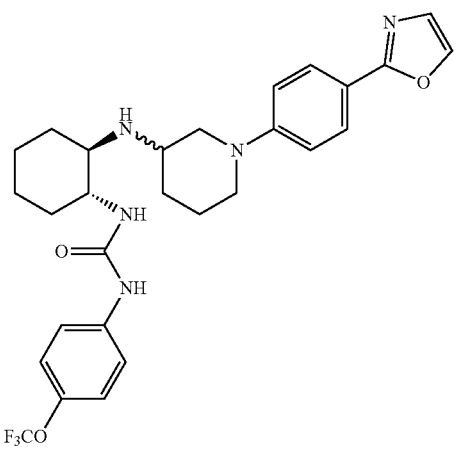 [SMILES: O=C(Nc1ccc(OC(F)(F)F)cc1)N[C@@H]1CCCC[C@H]1NC1CCCN(c2ccc(-c3ncco3)cc2)C1]

A: 1-(4-(Oxazol-2-yl)phenyl)piperidin-3-ol

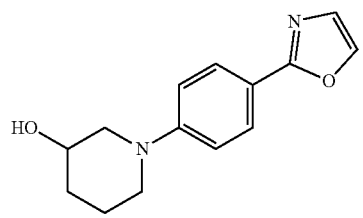 [SMILES: OC1CCCN(c2ccc(-c3ncco3)cc2)C1]

1-(4-(Oxazol-2-yl)phenyl)piperidin-3-ol (245 mg, 1.00 mmol) was synthesized, in 45% yield, as described in General Procedure B using 2-(4-bromophenyl)oxazole (500 mg, 2.232 mmol) and piperidin-3-ol (451 mg, 4.46 mmol). Anal. Calcd. for $C_{14}H_{16}N_2O_2$ m/z 244.2, found: 245.0 (M+H)$^+$.

B: 1-(4-(Oxazol-2-yl)phenyl)piperidin-3-yl methanesulfonate

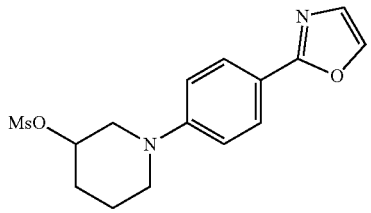 [SMILES: CS(=O)(=O)OC1CCCN(c2ccc(-c3ncco3)cc2)C1]

To a solution of 1-(4-(oxazol-2-yl)phenyl)piperidin-3-ol (85 mg, 0.348 mmol) in $CH_2Cl_2$ (2 mL) at 0° C. was added dropwise mesyl chloride (0.033 mL, 0.418 mmol), followed by $Et_3N$ (0.058 mL, 0.418 mmol). The reaction was stirred at 0° C. for 5 min, and then at rt for 30 min. After this time, HPLC and LC/MS showed that the desired product formed and no there was no starting material remaining. The reaction was concentrated. The residue was dissolved in EtOAc, washed with water, saturated aqueous $NaHCO_3$ and saturated aqueous NaCl. The organic layer was dried over $Na_2SO_4$, filtered and concentrated to give the desired product 1-(4-(oxazol-2-yl)phenyl)piperidin-3-yl methanesulfonate (110 mg, 0.341 mmol, 98% yield) as an off-white foam. Anal. Calcd. for $C_{15}H_{18}N_2O_4S$ m/z 322.3, found: 323.1 (M+H)$^+$.

C: tert-Butyl (1R,2R)-2-(1-(4-(oxazol-2-yl)phenyl)piperidin-3-ylamino)cyclohexylcarbamate

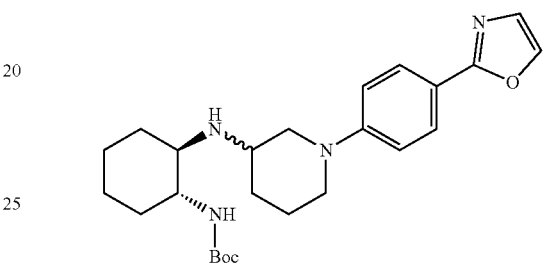

To a solution of 1-(4-(oxazol-2-yl)phenyl)piperidin-3-yl methanesulfonate (110 mg, 0.341 mmol) in acetonitrile (4 mL) was added tert-butyl (1R,2R)-2-aminocyclohexylcarbamate (110 mg, 0.512 mmol). The reaction was stirred in a microwave at 120° C. for 30 min. After this time, LC/MS showed two pairs of products formed. The reaction was concentrated. The residue was diluted with EtOAc and washed with water. EtOAc extracts were concentrated. The resulting residue was purified using silica gel chromatography (ISCO system) eluting with a gradient of 50-100% EtOAc/Hex to give desired product tert-butyl (1R,2R)-2-((1-(4-(oxazol-2-yl)phenyl)pyrrolidin-2-yl)methylamino)cyclohexylcarbamate and the unwanted diastereomer, tert-butyl (1R,2S)-2-((1-(4-(oxazol-2-yl)phenyl)pyrrolidin-2-yl)methylamino)cyclohexylcarbamate (156 mg total) as a white foam.

D: (1R,2R)—N1-(1-(4-(Oxazol-2-yl)phenyl)piperidin-3-yl)cyclohexane-1,2-diamine

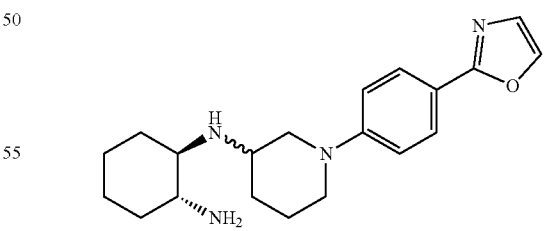

To a solution of tert-butyl (1R,2R)-2-(1-(4-(oxazol-2-yl)phenyl)piperidin-3-ylamino)cyclohexylcarbamate (32 mg, 0.073 mmol) and tert-butyl (1R,2R)-2-((1-(4-(oxazol-2-yl)phenyl)pyrrolidin-2-yl)methylamino)cyclohexylcarbamate (134.0 mg, 0.304 mmol) in $CH_2Cl_2$ (1.5 mL) was added trifluoroacetic acid (1.5 mL, 19.47 mmol). The reaction was stirred at rt for 1 h. After this time, LC/MS showed no starting material remained and the desired product formed. The reaction was concentrated, and the resulting residue was reconcentrated from CH₂Cl₂ (2×5 mL). The residue was dried under high vacuum for 1 h to afford the desired product (1R,2R)—N1-(1-(4-(oxazol-2-yl)phenyl)piperidin-3-yl)cyclohexane-1,2-diamine bis-trifluoroacetate (41 mg, 0.072 mmol, 99% yield) and (1R,2S)—N1-((1-(4-(oxazol-2-yl)phenyl)pyrrolidin-2-yl)methyl)cyclohexane-1,2-diamine bis-trifluoroacetate (35 mg, 0.073 mmol, 100% yield) as an oil.

E: 1-((1R,2R)-2-(1-(4-(Oxazol-2-yl)phenyl)piperidin-3-ylamino)cyclohexyl)-3-(4-(trifluoromethoxy)phenyl)urea

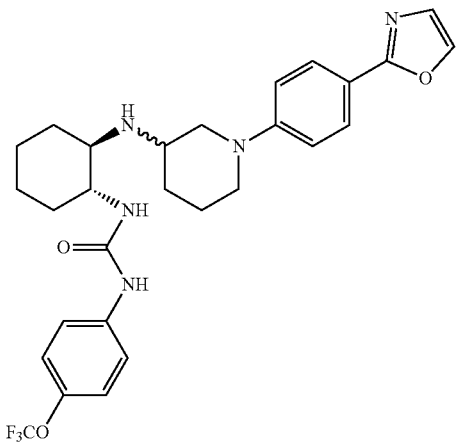 [SMILES: O=C(Nc1ccc(OC(F)(F)F)cc1)N[C@@H]1CCCC[C@H]1NC1CCCN(c2ccc(-c3ncco3)cc2)C1]

To a solution of (1R,2R)—N1-(1-(4-(oxazol-2-yl)phenyl)piperidin-3-yl)cyclohexane-1,2-diamine (11.58 mg, 0.034 mmol) and (1R,2R)—N1-((1-(4-(oxazol-2-yl)phenyl)pyrrolidin-2-yl)methyl)cyclohexane-1,2-diamine (47.7 mg, 0.14 mmol) in MeOH (1 mL) at rt was added benzyl 2,5-dioxopyrrolidin-1-yl carbonate (43.3 mg, 0.174 mmol), followed by diisopropyl ethyl amine (0.12 mL, 0.70 mmol). The reaction was stirred at rt for 10 min. After this time, LC/MS showed the desired product formed. The reaction was concentrated. The resulting residue was diluted with EtOAc and washed with water. The EtOAc layer was then concentrated. The resulting residue was purified by RP prep-HPLC. The product containing fractions were then lyophilized with CH₃CN to give the desired product benzyl (1R,2R)-2-((S)-1-(4-(oxazol-2-yl)phenyl)piperidin-3-ylamino)cyclohexylcarbamate trifluoroacetate (5 mg, 8.41 mmol, 6.01% yield) as a pink powder. Anal. Calcd. for C₂₈H₃₂F₃N₅O₃ m/z 543.5, found: 544.3 (M+H)⁺; ¹H NMR (400 MHz, CDCl₃) δ ppm 7.86 (d, J=8.84 Hz, 1H), 7.66 (s, 1H), 7.65-7.58 (m, 1H), 7.30-7.20 (m, 2H), 7.15 (d, J=8.84 Hz, 1H), 7.00-6.83 (m, 3H), 6.77 (d, J=8.59 Hz, 1H), 3.76-3.67 (m, 1H), 3.66-3.52 (m, 2H), 3.49 (s, 1H), 3.36 (br. s., 1H), 3.21 (br. s., 1H), 3.13-3.05 (m, 1H), 2.98 (br. s., 1H), 2.07 (br. s., 1H), 1.91 (br. s., 2H), 1.75 (br. s., 3H), 1.65-1.51 (m, 1H), 1.39-1.21 (m, 2H), 1.14 (br. s., 1H).

Example 16

4-(Trifluoromethoxy)benzyl (1R,2R)-2-((S)-1-(4-cyanophenyl)piperidin-3-ylamino)cyclohexylcarbamate

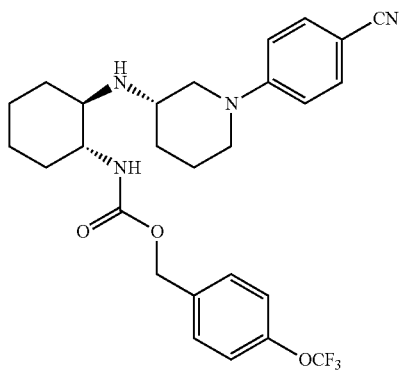 [SMILES: N#Cc1ccc(N2CCC[C@H](N[C@@H]3CCCC[C@H]3NC(=O)OCc3ccc(OC(F)(F)F)cc3)C2)cc1]

4-(Trifluoromethoxy)benzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (50 mg, 0.17 mmol) and 4-(trifluoromethoxy)benzyl carbonochloridate (65.8 mg, 0.18 mmol) according to General Procedure H to give 30 mg (34.7%) of light brown solid. Anal. Calcd. for C₂₇H₃₁F₃N₄O₃ m/z 516.2, found: 517.2 (M+H)⁺; ¹H NMR (400 MHz, DMSO-d₆) δ ppm 7.54 (d, J=8.8 Hz, 2H), 7.46 (d, J=8.4 Hz, 2H), 7.32 (d, J=8.0 Hz, 1H), 7.17 (d, J=8.04 Hz, 2H), 6.98 (d, J=8.8 Hz, 2H), 5.05 (t, J=8.1 Hz, 2H), 3.89 (m, 1H), 3.8 (m, 1H), 3.10 (m, 1H), 2.77 (m, 1H), 2.39 (m, 2H), 1.92 (m, 1H), 1.81 (m, 2H), 1.66 (m, 3H), 1.47 (m, 1H), 1.18 (m, 7H), 1.04 (m, 1H).

Example 17

1-(3-Hydroxyphenyl)-3-((1R,2R)-2-((S)-1-(4-nitrophenyl)piperidin-3-ylamino)cyclohexyl)urea

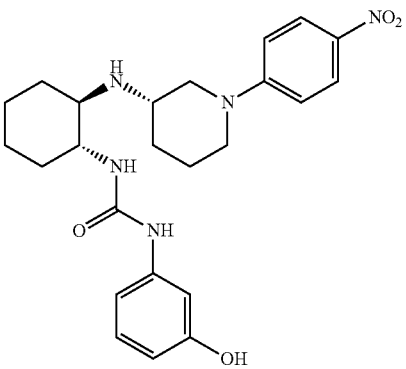 [SMILES: O=C(Nc1cccc(O)c1)N[C@@H]1CCCC[C@H]1N[C@H]1CCCN(c2ccc([N+](=O)[O-])cc2)C1]

1-(3-Hydroxyphenyl)-3-((1R,2R)-2-((S)-1-(4-nitrophenyl)piperidin-3-ylamino)cyclohexyl)urea was synthesized using (1R,2R)—N1-((S)-1-(4-nitrophenyl)piperidin-3-yl)cyclohexane-1,2-diamine (from intermediate D, Example 2)

(30 mg, 0.09 mmol) and 3-isocyanatophenol (25.8 mg, 0.09 mmol) according to General Procedure G to give 35 mg (81.9%) of yellow solid. Anal. Calcd. for $C_{24}H_{31}N_5O_4$ m/z 453.2, found: 454.2 (M+H)$^+$; $^1$H NMR (400 MHz, DMSO-$d_6$) δ ppm 9.28 (m, 1H), 8.71 (m, 1H), 8.51 (m, 2H), 7.96 (s, 1H), 7.87 (d, J=9.3 Hz, 2H), 6.96 (m, 3H), 6.89 (s, 1H), 6.60 (d, J=8.3 Hz, 1H), 6.3 (m, 2H), 2.80-2.70 (m, 2H), 2.18 (m, 2H), 1.93-1.63 (m, 6H), 1.48-1.31 (m, 12H).

Example 18

4-Methylbenzyl (1R,2R)-2-((S)-1-(4-cyanophenyl)piperidin-3-ylamino)cyclohexylcarbamate

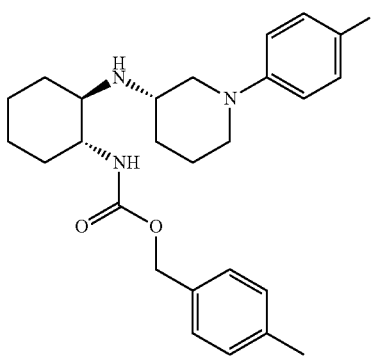

4-Methylbenzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (60 mg, 0.2 mmol) and 4-methylbenzyl carbonochloridate (63.5 mg, 0.22 mmol) according to General Procedure H to give 20 mg (22.3%) of white solid. Anal. Calcd. for $C_{27}H_{34}N_4O_2$ m/z 446.3, found: 447.2 (M+H)$^+$; $^1$H NMR (400 MHz, CD$_3$OD) δ ppm 7.45 (d, J=8.7 Hz, 2H), 7.19 (d, J=7.6 Hz, 2H), 7.11 (d, J=7.6 Hz, 2H), 6.96 (d, J=3 Hz, 2H), 4.98 (m, 2H), 3.68 (dm, 1H), 3.28 (m, 1H), 2.97 (m, 1H), 2.70 (m, 1H), 2.50 (m, 1H), 2.31 (s, 3H), 2.04 (m, 1H), 1.92 (m, 2H), 1.78 (m, 3H), 1.62 (m, 1H), 1.30 (m, 6H).

Example 19

4-Ethoxybenzyl (1R,2R)-2-((S)-1-(4-cyanophenyl)piperidin-3-ylamino)cyclohexylcarbamate

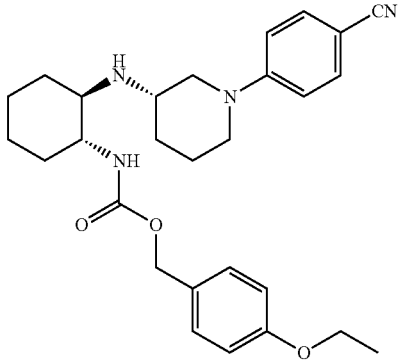 [SMILES: CCOc1ccc(COC(=O)N[C@@H]2CCCC[C@H]2N[C@H]2CCCN(c3ccc(C#N)cc3)C2)cc1]

4-Ethoxybenzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (50 mg, 0.17 mmol) and 4-ethoxybenzyl carbonochloridate (58.5 mg, 0.18 mmol) according to General Procedure H to give 65 mg (81%) of pale yellow solid. Anal. Calcd. for $C_{28}H_{36}N_4O_3$ m/z 476.3, found: 477.2 (M+H)$^+$; $^1$H NMR (400 MHz, DMSO-$d_6$) δ ppm 7.52 (d, J=8.9 Hz, 2H), 7.24 (d, J=8.4 Hz, 2H), 1H), 7.04 (d, J=8.6 Hz, 1H), 6.95 (d, J=9 Hz, 2H), 6.84 (d, J=8.4 Hz, 2H), 4.92 (m, 2H), 3.98 (m, 2H), 3.86 (d, J=6.9 Hz, 1H), 3.75 (d, J=12.5 Hz, 1H), 3.07 (m, 1H), 2.76 (m, 1H), 2.35 (m, 2H), 1.89 (m, 1H), 1.78 (m, 2H), 1.64 (m, 3H), 1.44 (m, 1H), 1.30 (t. J=7 Hz, 3H), 1.17 (m, 4H), 1.02 (m, 1H).

Example 20

2-Chlorobenzyl (1R,2R)-2-((S)-1-(4-cyanophenyl)piperidin-3-ylamino)cyclohexylcarbamate

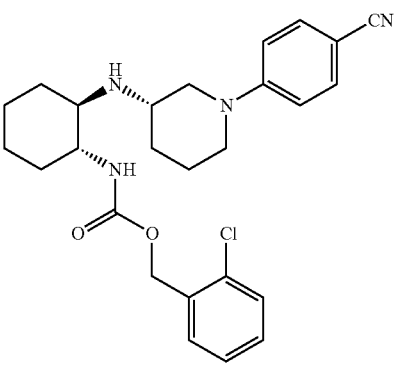 [SMILES: N#Cc1ccc(N2CCC[C@H](N[C@@H]3CCCC[C@H]3NC(=O)OCc3ccccc3Cl)C2)cc1]

2-Chlorobenzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (60 mg, 0.2 mmol) and 2-chlorobenzyl carbonochloridate (68 mg, 0.22 mmol) according to General Procedure H to give 20 mg (21.3%) of pale yellow solid. Anal. Calcd. for $C_{26}H_{31}ClN_4O_2$ m/z 466.2, found: 467.2 (M+H)$^+$; $^1$H NMR (400 MHz, CD$_3$OD) δ ppm 7.44 (d, J=8.7 Hz, 2H), 7.38 (m, 2H), 7.29 (m, 2H), 6.98 (d, J=9 Hz, 2H), 5.1 (s, 2H), 3.69 (m, 1H), 3.56 (m, 1H), 3.29 (m, 1H), 3.02 (m, 1H), 2.79 (d, J=8.4 Hz, 2H), 2.54 (m, 1H), 2.05 (m, 1H), 1.92 (m, 2H), 1.79 (m, 3H), 1.64 (m, 1H), 1.34 (m, 5H), 1.22 (m, 1H).

Example 21

Methyl 4-((S)-3-((1R,2R)-2-(benzyloxycarbonylamino)cyclohexylamino)piperidin-1-yl)benzoate

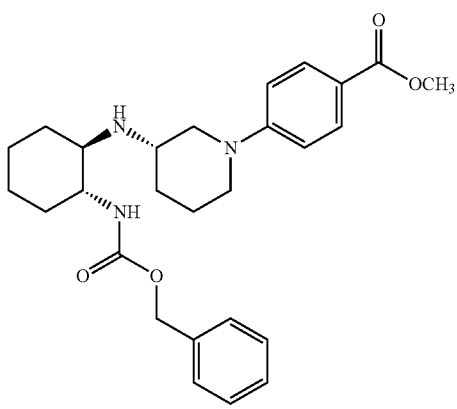 [SMILES: COC(=O)c1ccc(N2CCC[C@H](N[C@@H]3CCCC[C@H]3NC(=O)OCc3ccccc3)C2)cc1]

A: Methyl 4-((S)-3-((1R,2R)-2-aminocyclohexylamino)piperidin-1-yl)benzoate

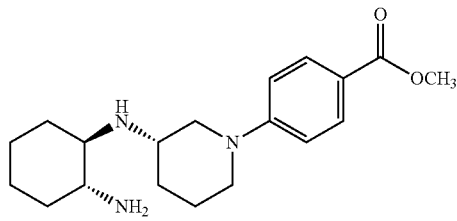 [SMILES: COC(=O)c1ccc(N2CCC[C@H](N[C@@H]3CCCC[C@H]3N)C2)cc1]

To a solution of 4-((S)-3-((1R,2R)-2-aminocyclohexylamino)piperidin-1-yl)benzonitrile (70 mg, 0.235 mmol) in MeOH (1 mL) at was added BF$_3$.OEt$_2$ (0.2 mL, 1.578 mmol) at rt. The reaction was stirred at reflux for 16 h. LC/MS showed only ~22% of the desired products formed. More BF$_3$.OEt$_2$ (100 µL, 0.789 mmol) was added. The reaction was stirred at reflux for another 6 days. The reaction mixture was concentrated. The residue was diluted with EtOAc, washed with saturated aq NaHCO$_3$, saturated aq NaCl solution. The organic extracts were concentrated under vacuum to give the crude product methyl 4-((S)-3-((1R,2R)-2-aminocyclohexylamino)piperidin-1-yl)benzoate (78 mg, 0.235 mmol, 100% yield). The product was used without further purification.

B: Methyl 4-((S)-3-((1R,2R)-2-(benzyloxycarbonylamino)cyclohexylamino)piperidin-1-yl)benzoate

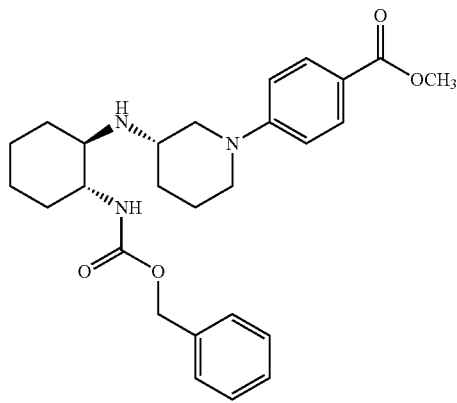 [SMILES: COC(=O)c1ccc(N2CCC[C@H](N[C@@H]3CCCC[C@H]3NC(=O)OCc3ccccc3)C2)cc1]

Methyl 4-((S)-3-((1R,2R)-2-(benzyloxycarbonylamino)cyclohexylamino) piperidin-1-yl)benzoate was synthesized using methyl 4-((S)-3-((1R,2R)-2-aminocyclohexylamino) piperidin-1-yl)benzoate (98 mg, 0.296 mmol) and benzyl 2,5-dioxopyrrolidin-1-yl carbonate (73.7 mg, 0.296 mmol) according to General Procedure H to give 38 mg (20% yield) of yellow solid. Anal. Calcd. for C$_{27}$H$_{35}$N$_3$O$_4$ m/z 465.5, found: 466.1 (M+H)$^+$; $^1$H NMR (400 MHz, CD$_3$OD) δ ppm 7.88 (d, J=9.0 Hz, 2H), 7.30-7.18 (m, 3H), 7.16-7.09 (m, 2H), 7.05 (d, J=8.9 Hz, 2H), 4.93 (s, 2H), 3.84 (s, 3H), 3.72-3.47 (m, 3H), 3.47-3.11 (m, 4H), 2.29 (d, J=13.4 Hz, 1H), 2.12-1.99 (m, 2H), 1.96-1.77 (m, 5H), 1.61-1.29 (m, 4H).

Example 22

1-((1R,2R)-2-((S)-1-(4-Cyanophenyl)piperidin-3-ylamino)cyclohexyl)-3-(4-(trifluoromethoxy)phenyl)urea

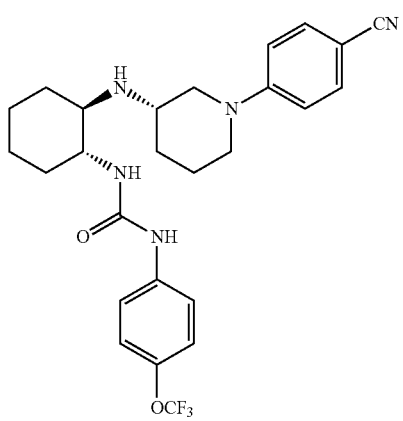 [SMILES: N#Cc1ccc(N2CCC[C@H](N[C@@H]3CCCC[C@H]3NC(=O)Nc3ccc(OC(F)(F)F)cc3)C2)cc1]

1-((1R,2R)-2-((S)-1-(4-Cyanophenyl)piperidin-3-ylamino)cyclohexyl)-3-(4-(trifluoromethoxy)phenyl)urea was synthesized using 4-((S)-3-((1R,2R)-2-aminocyclohexylamino)piperidin-1-yl)benzonitrile (from intermediate D, Example 10) (40 mg, 0.13 mmol) and 1-isocyanato-4-(trifluoromethoxy)benzene (27.2 mg, 0.13 mmol) according to General Procedure G to give 25 mg (37.2%) of white solid. Anal. Calcd. for C$_{26}$H$_{30}$F$_3$N$_5$O$_2$ m/z 501.2, found: 502.0 (M+H)$^+$; $^1$H NMR (400 MHz, DMSO-d$_6$) δ ppm 8.7 (s, 1H), 7.49 (d, J=9 Hz, 2H), 7.40 (d, J=8.9 Hz, 2H), 7.23 (d, J=8.9 Hz, 2H), 6.92 (d, J=8.9 Hz, 2H), 6.13 (d, J=7.4 Hz, 1H), 3.87 (d, J=11.8 Hz, 1H), 3.76 (d, J=12.9 Hz, 1H), 3.28 (m, 1H), 2.79 (m, 1H), 2.60 (m, 2H), 2.44 (m, 2H), 1.91 (m, 1H), 1.65 (m, 3H), 1.48 (m, 1H), 1.24 (m, 6H), 1.11 (m, 1H).

Example 23

1-(4-Hydroxyphenyl)-3-((1R,2R)-2-((S)-1-(4-nitrophenyl)piperidin-3-ylamino)cyclohexyl)urea

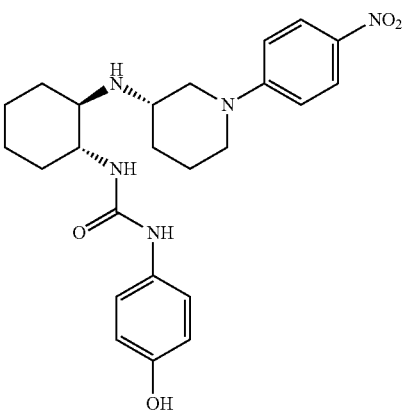 [SMILES: O=C(Nc1ccc(O)cc1)N[C@@H]1CCCC[C@H]1N[C@H]1CCCN(c2ccc([N+](=O)[O-])cc2)C1]

1-(4-Hydroxyphenyl)-3-((1R,2R)-2-((S)-1-(4-nitrophenyl)piperidin-3-ylamino)cyclohexyl)urea was synthesized using (1R,2R)—N1-((S)-1-(4-nitrophenyl)piperidin-3-yl)cyclohexane-1,2-diamine (from intermediate D, Example 2) (40 mg, 0.12 mmol) and 4-isocyanatophenol (37.9 mg, 0.138 mmol) according to General Procedure G to give 40 mg (70.2%) of yellow solid. Anal. Calcd. for $C_{24}H_{31}N_5O_4$ m/z 453.2, found: 454.2 (M+H)$^+$; $^1$H NMR (400 MHz, DMSO-$d_6$) δ ppm 9.05 (s, 1H), 8.64 (m, 2H), 8.28 (s, 1H), 7.88 (d, J=9.32 Hz, 2H), 7.03 (d, J=8.7 Hz, 2H), 6.98 (d, J=9.4 Hz, 2H), 6.61 (d, J=8.7 Hz, 2H), 6.20 (d, J=6.5 Hz, 1H), 3.83 (m, 1H), 3.61-3.17 (m, 7H), 2.12-1.73 (m, 6H), 1.63 (m, 1H), 1.46 (m, 1H), 1.30 (m, 6H).

Example 24

2-Chloro-4-methylbenzyl (1R,2R)-2-((S)-1-(4-cyanophenyl)piperidin-3-ylamino)cyclohexylcarbamate

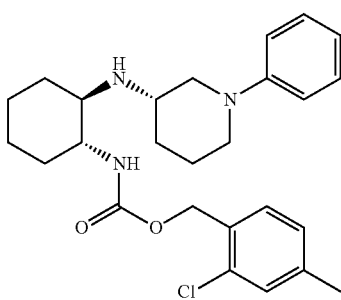

2-Chloro-4-methylbenzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (50 mg, 0.17 mmol) and 2-chloro-4-methylbenzyl carbonochloridate (59.3 mg, 0.18 mmol) according to General Procedure H to give 20 mg (24.8%) of white solid. Anal. Calcd. for $C_{27}H_{33}ClN_4O_2$ m/z 480.2, found: 481.2 (M+H)$^+$; $^1$H NMR (400 MHz, CD$_3$OD) δ ppm 7.43 (d, J=8.8 Hz, 2H), 7.27 (d, J=7.72 Hz, 2H), 7.19 (bs, 1H), 7.06 (m, 1H), 6.97 (m, 2H), 5.06 (m, 2H), 3.67 (m, 1H), 3.56 (m, 1H), 3.00 (m, 1H), 2.78 (m, 2H), 2.52 (m, 1H), 2.31 (s, 3H), 2.04 (m, 1H), 1.93 (m, 2H), 1.79 (m, 3H), 1.64 (m, 1H), 1.34 (m, 8H).

Example 25

4-(Trifluoromethyl)benzyl (1R,2R)-2-((S)-1-(4-cyanophenyl)piperidin-3-ylamino)cyclohexylcarbamate

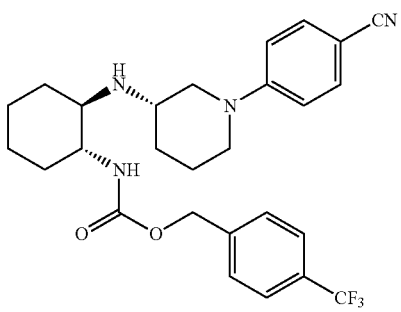 [SMILES: N#Cc1ccc(N2CCC[C@H](N[C@@H]3CCCC[C@H]3NC(=O)OCc3ccc(C(F)(F)F)cc3)C2)cc1]

4-(Trifluoromethyl)benzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (52 mg, 0.17 mmol) and 4-(trifluoromethyl)benzyl carbonochloridate (71.3 mg, 0.21 mmol) according to General Procedure H to give 27.4 mg (32.2%) of white solid. Anal. Calcd. for $C_{22}H_{31}F_3N_4O_2$ m/z 500.2, found: 501.2 (M+H)$^+$; $^1$H NMR (400 MHz, CD$_3$OD) δ ppm 7.60 (d, J=8.1 Hz, 2H), 7.48 (m, 4H), 6.98 (d, J=9 Hz, 2H), 5.08 (s, 2H), 3.66 (m, 4H), 3.58 (m, 1H), 3.0 (m, 1H), 2.75 (m, 2H), 2.5 (m, 1H), 2.1 (d, 1H), 2.04 (s, 1H), 1.93 (s, 2H), 1.8 (m, 3H), 1.76 (s, 3H), 1.6 (m, 1H), 1.34 (m, 5H).

Example 26

1-(4-Methoxyphenyl)-3-((1R,2R)-2-((S)-1-(4-nitrophenyl)piperidin-3-ylamino)cyclohexyl)urea

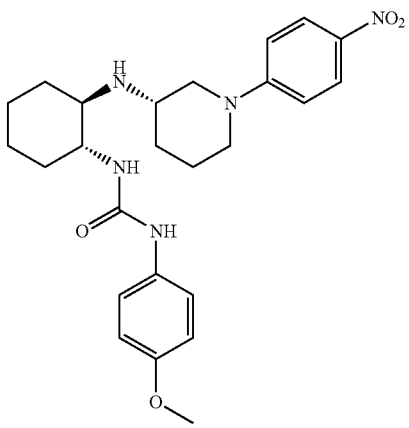 [SMILES: COc1ccc(NC(=O)N[C@@H]2CCCC[C@H]2N[C@H]2CCCN(c3ccc([N+](=O)[O-])cc3)C2)cc1]

1-(4-Methoxyphenyl)-3-((1R,2R)-2-((S)-1-(4-nitrophenyl)piperidin-3-ylamino)cyclohexyl)urea was synthesized using (1R,2R)—N1-((S)-1-(4-nitrophenyl)piperidin-3-yl)cyclohexane-1,2-diamine (from intermediate D, Example 2) (84 mg, 0.38 mmol) and 1-isocyanato-4-methoxybenzene (100 mg, 0.38 mmol) according to General Procedure G to give 15 mg (8.4%) of yellow solid. Anal. Calcd. for $C_{25}H_{33}N_5O_4$ m/z 467.2, found: 468.0 (M+H)$^+$; $^1$H NMR (400 MHz, DMSO-$d_6$) δ ppm 8.66 (m, 1H), 8.61 (m, 1H), 8.57 (m, 1H), 8.41 (s, 1H), 7.84 (d, J=9.4 Hz, 2H), 7.16 (d, J=9 Hz, 2H), 6.96 (d, J=9.5 Hz, 2H), 6.78 (d, J=9 Hz, 2H), 6.26 (d, J=7.12 Hz, 1H), 3.83 (d, J=11.2 Hz, 1H), 3.7 (s, 3H), 3.55 (m, 6H), 3.19 (m, 1H), 2.11 (m, 2H), 1.77 (m, 5H), 1.36 (m, 6H).

Example 27

4-Chlorobenzyl (1R,2R)-2-((S)-1-(4-cyanophenyl)piperidin-3-ylamino)cyclohexylcarbamate

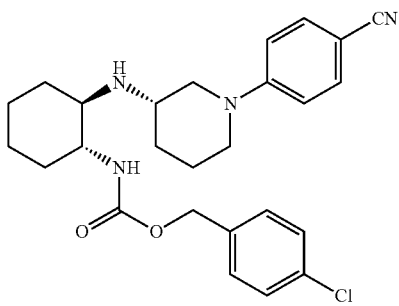 [SMILES: N#Cc1ccc(N2CCC[C@H](N[C@@H]3CCCC[C@H]3NC(=O)OCc3ccc(Cl)cc3)C2)cc1]

4-Chlorobenzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (60 mg, 0.20 mmol) and 4-chlorobenzyl carbonochloridate (68 mg, 0.22 mmol) according to General Procedure H to give 25 mg (26.6%) of white solid. Anal. Calcd. for $C_{26}H_{31}ClN_4O_2$ m/z 466.2, found: 467.2 (M+H)$^+$; $^1$H NMR (400 MHz, CD$_3$OD) δ ppm 7.48 (d, J=8.9 Hz, 2H), 7.30 (s, 4H), 6.98 (d, J=9 Hz, 2H), 4.99 (m, 2H), 3.70 (m, 1H), 3.57 (m, 1H), 3.29 (m, 1H), 2.98 (m, 1H), 2.75 (m, 1H), 2.68 (m, 1H), 2.50 (m, 1H), 2.04 (m, 1H), 1.91 (m, 2H), 1.77 (m, 3H), 1.64 (m, 1H), 1.32 (m, 5H), 1.21 (m, 1H).

Example 28

1-(4-(Trifluoromethoxy)phenyl)-3-((1R,2R)-2-((S)-1-(4-(trifluoromethyl)phenyl)piperidin-3-ylamino)cyclohexyl)urea

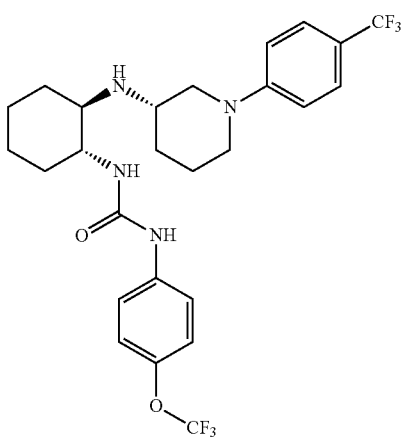 [SMILES: O=C(Nc1ccc(OC(F)(F)F)cc1)N[C@@H]1CCCC[C@H]1N[C@H]1CCCN(c2ccc(C(F)(F)F)cc2)C1]

1-(4-(Trifluoromethoxy)phenyl)-3-((1R,2R)-2-((S)-1-(4-(trifluoromethyl)phenyl)piperidin-3-ylamino)cyclohexyl)urea was synthesized using (1R,2R)—N1-((S)-1-(4-(trifluoromethyl)phenyl)piperidin-3-yl)cyclohexane-1,2-diamine (from intermediate D, Example 12) (50 mg, 0.15 mmol) and 1-isocyanato-4-(trifluoromethoxy)benzene (31 mg, 0.15 mmol) according to General Procedure G to give 26.3 mg (33%) of light yellow solid. Anal. Calcd. for $C_{26}H_{30}F_6N_4O_2$ m/z 544.2, found: 545.4 (M+H)$^+$; $^1$H NMR (400 MHz, CD$_3$OD) δ ppm 7.25 (m, 4H), 7.10 (d, J=8.8 Hz, 2H), 6.92 (d, J=8.7 Hz, 2H), 3.57 (m, 1H), 3.19 (m, 2H), 3.08 (m, 1H), 2.99 (m, 1H), 2.22 (m, 1H), 2.06-1.87 (m, 7H), 1.44 (m, 4H).

Example 29

3-Methylbenzyl (1R,2R)-2-((S)-1-(4-cyanophenyl)piperidin-3-ylamino)cyclohexylcarbamate

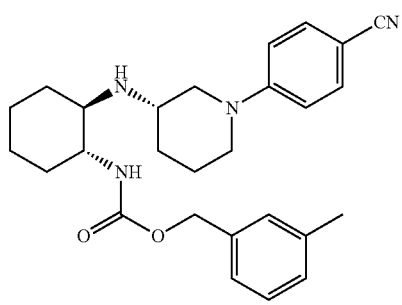

3-Methylbenzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (60 mg, 0.20 mmol) and 3-methylbenzyl carbonochloridate (63.5 mg, 0.22 mmol) according to General Procedure H to give 30 mg (33.4%) of white solid. Anal. Calcd. for $C_{27}H_{34}N_4O_2$ m/z 446.3, found: 447.2 (M+H)$^+$; $^1$H NMR (400 MHz, CD$_3$OD) δ ppm 7.45 (d, J=8.8 Hz, 2H), 7.19 (m, 1H), 7.12 (m, 2H), 6.97 (dd, J=8.8 Hz, J=2.8 Hz, 2H), 4.98 (m, 2H), 3.71 (m, 1H), 3.59 (m, 1H), 3.28 (m, 1H), 2.97 (m, 1H), 2.74 (m, 1H), 2.66 (m, 1H), 2.50 (m, 1H), 2.31 (s, 3H), 2.04 (m, 1H), 1.92 (m, 2H), 1.78 (m, 3H), 1.62 (m, 1H), 1.28 (m, 5H).

Example 30

3-Chlorobenzyl (1R,2R)-2-((S)-1-(4-cyanophenyl)piperidin-3-ylamino)cyclohexylcarbamate

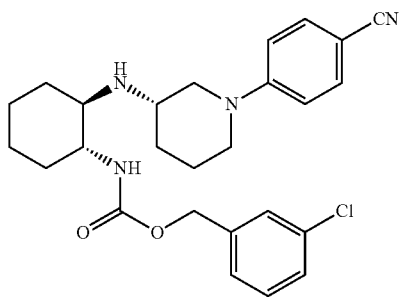 [SMILES: N#Cc1ccc(N2CCC[C@H](N[C@@H]3CCCC[C@H]3NC(=O)OCc3cccc(Cl)c3)C2)cc1]

3-Chlorobenzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (60 mg, 0.20 mmol) and 3-chlorobenzyl carbonochloridate (68 mg, 0.22 mmol) according to General Procedure H to give 20 mg (21.3%) of white solid. Anal. Calcd. for $C_{26}H_{31}ClN_4O_2$ m/z 466.2, found: 467.2 (M+H)$^+$; $^1$H NMR (400 MHz, CD$_3$OD) δ ppm 7.46 (d, J=8.8 Hz, 2H), 7.35 (m, 1H), 7.30 (m, 4H), 7.28 (m, 2H), 7.23 (m, 1H), 6.96 (d, J=3 Hz, 2H), 5.0 (m, 2H), 3.71 (m, 1H), 3.58 (m, 1H), 3.29 (m, 1H), 2.98 (m, 1H), 2.72 (m, 2H), 2.52 (m, 1H), 2.04 (m, 1H), 1.92 (m, 2H), 1.78 (m, 3H), 1.62 (m, 1H), 1.34 (m, 4H), 1.20 (m, 1H).

Example 31

Benzyl (1R,2R)-2-((S)-1-(4-(oxazol-2-yl)phenyl)piperidin-3-ylamino)cyclohexylcarbamate

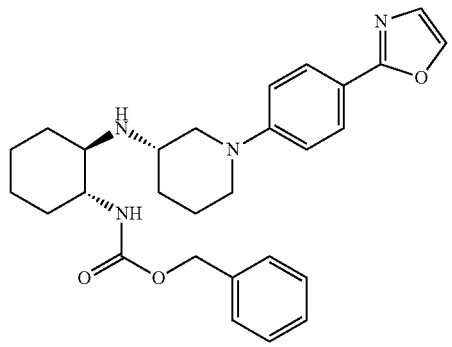 [SMILES: O=C(N[C@@H]1CCCC[C@H]1N[C@H]1CCCN(c2ccc(-c3ncco3)cc2)C1)OCc1ccccc1]

Benzyl (1R,2R)-2-((S)-1-(4-(oxazol-2-yl)phenyl)piperidin-3-ylamino)cyclohexylcarbamate was synthesized using (1R,2R)—N1-(1-(4-(oxazol-2-yl)phenyl)piperidin-3-yl)cyclohexane-1,2-diamine (from Example 15, step D) (11.58 mg, 0.034 mmol) and benzyl 2,5-dioxopyrrolidin-1-yl carbonate (8.5 mg, 0.034 mmol) according to General Procedure H to give 5 mg (20% yield) of the title compound as a pink solid. Anal. Calcd. for $C_{28}H_{34}N_4O_3$ m/z 474.5, found: 475.3 (M+H)$^+$; $^1$H NMR (400 MHz, CDCl$_3$) δ ppm 7.90 (d, J=8.8 Hz, 2H), 7.71 (s, 1H), 7.39 (s, 1H), 7.24-7.08 (m, 5H), 6.98 (d, J=8.7 Hz, 2H), 4.79 (s, 2H), 3.67-3.53 (m, 1H), 3.53-3.42 (m, 2H), 3.42-3.30 (m, 2H), 3.29-3.19 (m, 2H), 2.22 (d, J=10.4 Hz, 1H), 2.14-1.85 (m, 5H), 1.84-1.54 (m, 4H), 1.44-1.19 (m, 2H).

Example 32

Ethyl 4-((S)-3-((1R,2R)-2-(benzyloxycarbonylamino)cyclohexylamino)pyrrolidin-1-yl)benzoate

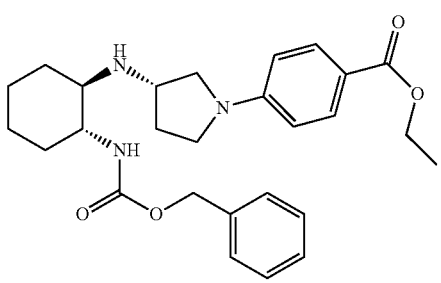 [SMILES: CCOC(=O)c1ccc(N2CC[C@H](N[C@@H]3CCCC[C@H]3NC(=O)OCc3ccccc3)C2)cc1]

A: Ethyl 4-(3-hydroxypyrrolidin-1-yl)benzoate

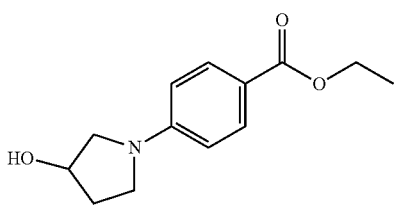 [SMILES: CCOC(=O)c1ccc(N2CCC(O)C2)cc1]

To a seal tube was added pyrrolidin-3-ol (1 gm, 11.48 mmol), ethyl 4-fluorobenzoate (2.90 gm, 17.22 mmol) and DMSO (20 ml). The reaction was stirred at 110° C. for 20 hrs. After this time, the reaction was diluted with water (50 ml). The resulting solution was extracted with EtOAc (2×50 ml). The combined organics were washed with saturated NaHCO$_3$ (50 ml), water (50 ml) and saturated aqueous NaCl (50 ml). The organic layer was separated, dried over MgSO$_4$, filtered and concentrated. The resulting residue was purified using silica gel chromatography (ISCO system) eluting with a gradient of 50-100% EtOAc/Hex) to give the product ethyl 4-(3-hydroxypyrrolidin-1-yl)benzoate (1.52 g, 6.46 mmol, 56.3% yield) as white solid. Anal. Calcd. for $C_{13}H_{12}NO_3$ m/z 235.3, found: 236.4 (M+H)$^+$; $^1$H NMR (400 MHz, CDCl$_3$) δ ppm 7.97-7.87 (m, 2H), 6.61-6.44 (m, 2H), 4.77-4.57 (m, 1H), 4.32 (q, J=7.1 Hz, 2H), 3.63-3.51 (m, 2H), 3.49-3.40 (m, 1H), 3.34 (d, J=10.8 Hz, 1H), 2.27-2.03 (m, 2H), 1.73 (d, J=4.4 Hz, 1H), 1.37 (t, J=7.1 Hz, 3H).

B: Ethyl 4-(3-oxopyrrolidin-1-yl)benzoate

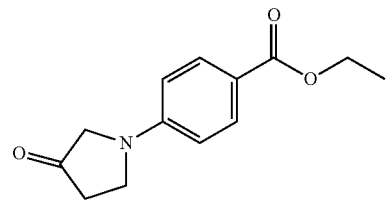 [SMILES: CCOC(=O)c1ccc(N2CCC(=O)C2)cc1]

To a round bottom flask was added CH$_2$Cl$_2$ (30 ml), 2M oxalyl chloride (4.31 mL, 8.63 mmol). The resulting solution was cooled to −78° C. DMSO (1.225 mL, 17.26 mmol) was then slowly added to the solution over 10 min. The reaction was then stirred at −78° C. for 15 min. The ethyl 4-(3-hydroxypyrrolidin-1-yl)benzoate (1.45 g, 6.16 mmol) pre-dissolved in CH$_2$Cl$_2$ (15 ml) was added to the reaction mixture over 10 min. The resulting solution was stirred at −78° C. for 2 hrs. After this time, Et$_3$N (3.78 mL, 27.1 mmol) was added to the reaction mixture and the resulting solution was slowly warmed to 0° C. over 20 min. The reaction mixture was then diluted with CH$_2$Cl$_2$ (100 ml). The reaction mixture was wash with saturated aqueous NaHCO$_3$ (100 ml), water (100 ml) and saturated aqueous NaCl (100 ml). The organic layer was separated, dried over MgSO$_4$, filtered and concentrated to give crude product. The resulting residue was purified using silica gel chromatography (ISCO system) eluting with a gradient of 0-30% EtOAc/Hex) to give the product ethyl 4-(3-oxopyrrolidin-1-yl)benzoate (1.31 g, 5.62 mmol, 91% yield) as yellow solid. Anal. Calcd. for $C_{13}H_{15}NO_3$ m/z 233.2, found: 234.0 (M+H)$^+$.

C: Ethyl 4-(3-((1R,2R)-2-aminocyclohexylamino)pyrrolidin-1-yl)benzoate

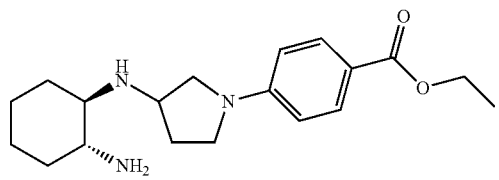 [SMILES: CCOC(=O)c1ccc(N2CCC(N[C@@H]3CCCC[C@H]3N)C2)cc1]

To a round bottom flask under argon was added the ethyl 4-(3-oxopyrrolidin-1-yl)benzoate (1.23 g, 5.27 mmol), (1R,2R)-cyclohexane-1,2-diamine (0.602 g, 5.27 mmol), CH$_2$Cl$_2$ (30 ml), solid anhydrous Na$_2$SO$_4$ (2.5 gm) and HOAc (1 ml). Argon was bubbled through the reaction mixture for 1 min and then the reaction was stirred under argon at rt for 1 hr. After this time, sodium triacetoxy borohydride (2.012 g, 9.49 mmol) was added to the reaction which was then stirred at rt overnight. The reaction was filtered and water (10 ml) was added to the reaction. The reaction mixture was then diluted with CH$_2$Cl$_2$ (100 ml). The resulting solution was washed with saturated aqueous NaHCO$_3$ (100 ml), water (50 ml) and saturated aqueous NaCl (50 ml). The organic layer was separated, dried over MgSO$_4$, filtered and concentrated to give the product ethyl 4-(3-((1R,2R)-2-aminocyclohexylamino)pyrrolidin-1-yl)benzoate (1 g, 3.02 mmol, 57.2% yield) as brown solid. Anal. Calcd. for $C_{19}H_{29}N_3O_2$ m/z 331.4, found: 332.1 (M+H)$^+$.

D: Ethyl 4-((S)-3-((1R,2R)-2-(benzyloxycarbonylamino)cyclohexylamino)pyrrolidin-1-yl)benzoate trifluoroacetate

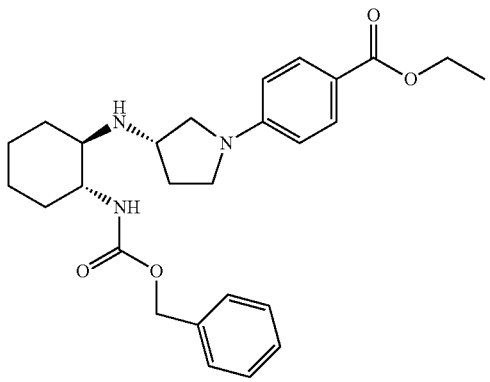 [SMILES: CCOC(=O)c1ccc(N2CC[C@H](N[C@@H]3CCCC[C@H]3NC(=O)OCc3ccccc3)C2)cc1]

To a solution of ethyl 4-((S)-3-((1R,2R)-2-aminocyclohexylamino)pyrrolidin-1-yl)benzoate (500 mg, 0.754 mmol) in MeOH (2 mL) at rt was added benzyl 2,5-dioxopyrrolidin-1-yl carbonate (188 mg, 0.754 mmol), followed by diisopropyl ethyl amine (0.263 mL, 1.509 mmol). The reaction was stirred at rt for 5 min. The reaction was concentrated and then diluted with EtOAc. The solution was washed with water. The organic layer was separated and concentrated. The resulting residue was purified by RP prep-HPLC and the fraction containing the desired diastereomer was concentrated to give the desired product ethyl 4-((S)-3-((1R,2R)-2-(benzyloxycarbonylamino) cyclohexylamino)pyrrolidin-1-yl)benzoate as trifluoroacetate (50 mg, 0.085 mmol, 11.21% yield) as a brownish oil. Anal. Calcd. for $C_{27}H_{35}N_3O_4$ m/z 465.5, found: 466.2 (M+H)$^+$; $^1$H NMR (400 MHz, CD$_3$OD) δ ppm 7.88 (d, J=8.8 Hz, 2H), 7.30-7.12 (m, 5H), 6.65 (d, J=8.9 Hz, 2H), 4.94 (s, 2H), 4.60 (d, J=12.2 Hz, 1H), 4.28 (q, J=7.1 Hz, 2H), 4.22-4.13 (m, 1H), 3.72-3.50 (m, 3H), 3.49-3.37 (m, 1H), 3.25-3.13 (m, 1H), 2.63-2.41 (m, 1H), 2.40-2.20 (m, 2H), 2.00 (d, J=12.8 Hz, 1H), 1.92-1.75 (m, 2H), 1.60-1.24 (m, 7H).

Example 33

Methyl 4-((S)-3-((1R,2R)-2-(benzyloxycarbonylamino)cyclohexylamino)pyrrolidin-1-yl)benzoate trifluoroacetate

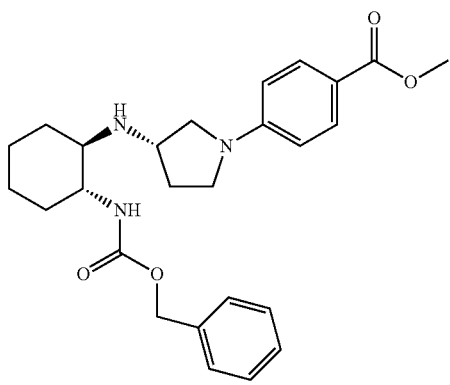 [SMILES: COC(=O)c1ccc(N2CC[C@H](N[C@@H]3CCCC[C@H]3NC(=O)OCc3ccccc3)C2)cc1]

To a round bottom flask was added ethyl 4-((S)-3-((1R,2R)-2-(benzyloxycarbonylamino)cyclohexylamino)pyrrolidin-1-yl)benzoate trifluoroacetate (30 mg, 0.052 mmol), LiOH monohydrate (37 mg, 1.56 mmol) in water (1 ml) and MeOH (1 ml). The reaction was stirred at rt for 16 hrs. The reaction was concentrated and the residue was purified by RP prep-HPLC to afford methyl 4-((S)-3-((1R,2R)-2-(benzyloxycarbonylamino)cyclohexylamino)pyrrolidin-1-yl)benzoate trifluoroacetate (8 mg, 0.014 mmol, 26.8% yield) as a beige solid. Anal. Calcd. for $C_{26}H_{33}N_3O_4$ m/z 451.5, found: 452.3 (M+H)$^+$; $^1$H NMR (400 MHz, CD$_3$OD) δ ppm 7.90 (d, J=8.8 Hz, 2H), 7.45-7.31 (m, 1H), 7.29-7.15 (m, 4H), 6.67 (d, J=8.8 Hz, 2H), 4.93 (s, 2H), 4.63 (d, J=12.2 Hz, 1H), 4.25-4.11 (m, 1H), 3.72-3.39 (m, 4H), 3.23-3.12 (m, 1H), 2.61-2.42 (m, 1H), 2.40-2.19 (m, 2H), 2.09-1.95 (m, 1H), 1.94-1.77 (m, 2H), 1.63-1.23 (m, 4H).

Example 34

4-Methoxybenzyl (1R,2R)-2-((S)-1-(4-cyanophenyl)piperidin-3-ylamino)cyclohexylcarbamate

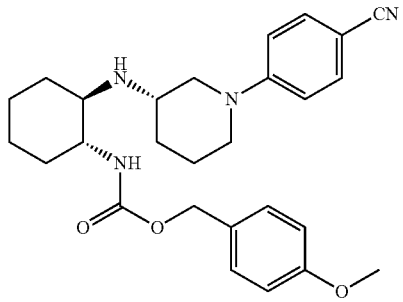 [SMILES: COc1ccc(COC(=O)N[C@@H]2CCCC[C@H]2N[C@H]2CCCN(c3ccc(C#N)cc3)C2)cc1]

4-Methoxybenzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (41 mg, 0.14 mmol) and 4-methoxybenzyl carbonochloridate (45.8 mg, 0.15 mmol) according to General Procedure H to give 28 mg (44%) of light brown solid. Anal. Calcd. for $C_{27}H_{34}N_4O_3$ m/z 462.3, found: 463.2 (M+H)$^+$; $^1$H NMR (400 MHz, DMSO-d$_6$) δ ppm 7.52 (d, J=8.7 Hz, 2H), 7.26 (d, J=8.2 Hz, 2H), 7.04 (d, J=8.77 Hz, 1H), 6.96 (d, J=8.9 Hz, 2H), 6.87 (d, J=8.2 Hz, 2H), 4.94 (m, 2H), 3.86 (m, 1H), 3.73 (s, 4H), 3.08 (m, 1H), 2.76 (m, 1H), 2.36 (m, 2H), 1.90 (m, 1H), 1.80 (m, 2H), 1.65 (m, 1H), 1.45 (m, 1H), 1.18 (m, 5H), 1.02 (m, 1H).

Example 35

4-Ethoxyphenyl (1R,2R)-2-((S)-1-(4-cyanophenyl)piperidin-3-ylamino)cyclohexylcarbamate

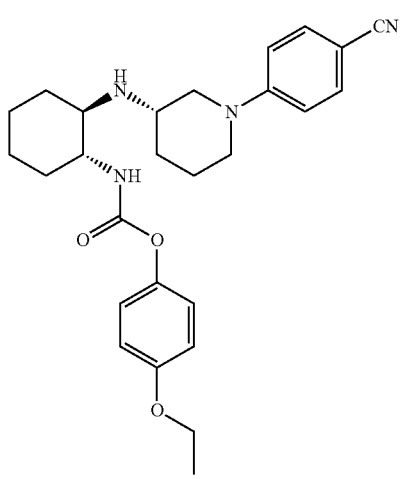 [SMILES: CCOc1ccc(OC(=O)N[C@@H]2CCCC[C@H]2N[C@H]2CCCN(c3ccc(C#N)cc3)C2)cc1]

4-Ethoxyphenyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (41 mg, 0.14 mmol) and 4-ethoxyphenyl carbonochloridate (22.6 mg, 0.14 mmol) according to General Procedure H to give 50 mg (78.3%) of white solid. Anal. Calcd. for $C_{27}H_{35}N_5O_2$ m/z 461.3, found: 462.4 (M+H)$^+$; $^1$H NMR (400 MHz, DMSO-$d_6$) δ ppm 8.28 (s, 1H), 7.41 (d, J=9 Hz, 2H), 7.28 (q, J=3.0 Hz, 2H), 6.92 (d, J=9 Hz, 2H), 6.8 (d, J=9 Hz, 2H), 5.97 (d, J=7.8 Hz, 1H), 3.95 (q, J=7.0 Hz, 2H), 3.88 (d, J=11.4 Hz, 1H), 3.77 (d, J=13 Hz, 1H), 3.25 (m, 1H), 2.78 (m, 1H), 2.58 (m, 1H), 2.39 (m, 2H), 1.88 (m, 3H), 1.68 (m, 1H), 1.61 (m, 3H), 1.47 (m, 1H), 1.30 (t, J=7.0 Hz, 3H), 1.2 (m, 4H), 1.11 (m, 1H).

Example 36

1-((1R,2R)-2-((S)-1-(4-Cyanophenyl)piperidin-3-ylamino)cyclohexyl)-3-(3-hydroxyphenyl)urea

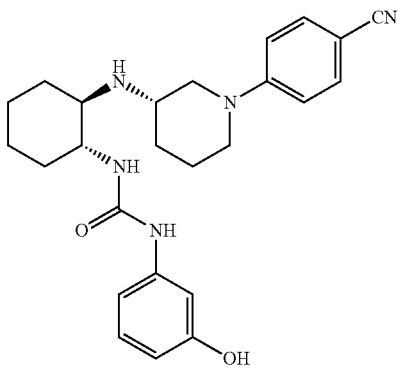 [SMILES: N#Cc1ccc(N2CCC[C@H](N[C@@H]3CCCC[C@H]3NC(=O)Nc3cccc(O)c3)C2)cc1]

1-((1R,2R)-2-((S)-1-(4-Cyanophenyl)piperidin-3-ylamino)cyclohexyl)-3-(3-hydroxyphenyl)urea was synthesized using 4-((S)-3-((1R,2R)-2-aminocyclohexylamino)piperidin-1-yl)benzonitrile (from intermediate D, Example 10) (40 mg, 0.13 mmol) and 3-isocyanatophenol (40.4 mg, 0.15 mmol) according to General Procedure G to give 20 mg (34.4%) of white solid. Anal. Calcd. for $C_{25}H_{31}N_5O_2$ m/z 433.2, found: 434.2 (M+H)$^+$; $^1$H NMR (400 MHz, DMSO-$d_6$) δ ppm 9.31 (s, 1H), 8.66 (m, 1H), 8.52 (s, 1H), 8.41 (m, 1H), 7.41 (d, J=8.9 Hz, 2H), 6.97 (m, 4H), 6.66 (d, J=9.3 Hz, 2H), 6.34 (m, 2H), 3.79 (m, 1H), 3.56 (m, 3H), 3.26 (m, 2H), 3.00 (m, 1H), 2.11 (m, 2H), 1.92 (m, 1H), 1.78 (m, 1H), 1.62 (m, 1H), 1.49 (m, 1H), 1.32 (m, 6H).

Example 37

2-Methylbenzyl (1R,2R)-2-((S)-1-(4-cyanophenyl)piperidin-3-ylamino)cyclohexylcarbamate

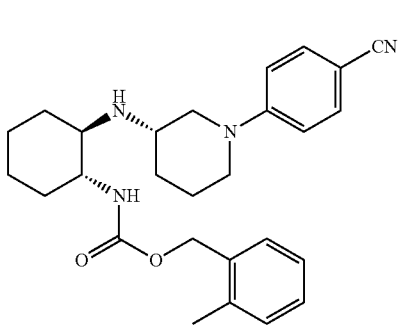 [SMILES: Cc1ccccc1COC(=O)N[C@@H]1CCCC[C@H]1N[C@H]1CCCN(c2ccc(C#N)cc2)C1]

2-Methylbenzyl (1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (60 mg, 0.20 mmol) and 2-methylbenzyl carbonochloridate (63.5 mg, 0.22 mmol) according to General Procedure H to give 25 mg (27.8%) of white solid. Anal. Calcd. for $C_{27}H_{34}N_4O_2$ m/z 446.3, found: 447.2 (M+H)$^+$; $^1$H NMR (400 MHz, CD$_3$OD) δ ppm 7.45 (d, J=8.7 Hz, 2H), 7.26 (d, J=7.3 Hz, 1H), 7.19 (m, 1H), 7.14 (m, 2H), 6.98 (m, 2H), 5.05 (m, 2H), 3.7 (m, 1H), 3.55 (m, 1H), 3.28 (m, 1H), 2.97 (m, 1H), 2.74 (m, 1H), 2.68 (m, 1H), 2.50 (m, 1H), 2.31 (s, 3H), 2.04 (m, 1H), 1.91 (m, 2H), 1.78 (m, 3H), 1.61 (m, 1H), 1.33 (m, 5H), 1.21 (m, 1H).

Example 38

1-(4-Chlorophenyl)-3-((1R,2R)-2-((S)-1-(4-cyanophenyl)piperidin-3-ylamino)cyclohexyl)urea

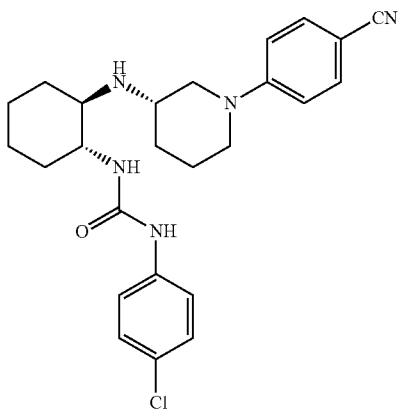 [SMILES: N#Cc1ccc(N2CCC[C@H](N[C@@H]3CCCC[C@H]3NC(=O)Nc3ccc(Cl)cc3)C2)cc1]

1-(4-Chlorophenyl)-3-((1R,2R)-2-((S)-1-(4-cyanophenyl)piperidin-3-ylamino)cyclohexyl)urea was synthesized using 4-((S)-3-((1R,2R)-2-aminocyclohexylamino)piperidin-1-yl)benzonitrile (from intermediate D, Example 10) (60 mg, 0.2 mmol) and 1-chloro-4-isocyanatobenzene (30.9 mg, 0.2 mmol) according to General Procedure G to give 25 mg (27.5%) of white solid. Anal. Calcd. for $C_{25}H_{30}ClN_5O$ m/z 451.2, found: 452.2 (M+H)$^+$; $^1$H NMR (400 MHz, DMSO-$d_6$) δ ppm 8.66 (bs, 1H), 7.43 (d, J=8.8 Hz, 4H), 7.26 (d, J=8.8 Hz, 2H), 6.95 (m, 2H), 6.13 (s, 1H), 3.80 (m, 2H), 3.3 (m, 1H), 2.79 (bs, 1H), 2.4 (m, 1H), 1.91 (m, 3H), 1.64 (m, 4H), 1.48 (m, 1H), 1.23 (m, 4H).

Example 39

1-((1R,2R)-2-((S)-1-(4-Chlorophenyl)piperidin-3-ylamino)cyclohexyl)-3-phenylurea

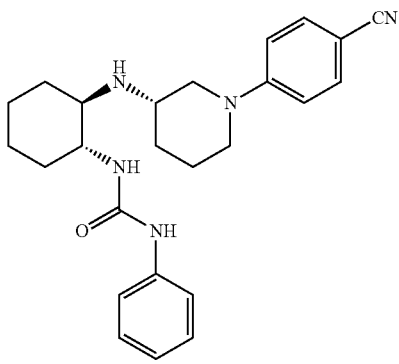 [SMILES: N#Cc1ccc(N2CCC[C@H](N[C@@H]3CCCC[C@H]3NC(=O)Nc3ccccc3)C2)cc1]

1-((1R,2R)-2-((S)-1-(4-Chlorophenyl)piperidin-3-ylamino)cyclohexyl)-3-phenylurea was synthesized according to the method of Example 15 to give 8 mg of the title compound as a yellow solid. Anal. Calcd. for $C_{24}H_{31}ClN_4O$ m/z 426.5, found: 427.3 (M+H)+; 1H NMR (500 MHz, CDCl3) δ ppm 7.23-7.11 (m, 4H), 7.05-6.95 (m, 4H), 6.73 (d, J=8.80 Hz, 2H), 3.63 (br. s., 1H), 3.37-3.25 (m, 2H), 3.21 (d, J=11.00 Hz, 1H), 3.08-2.90 (m, 4H), 2.08 (d, J=10.45 Hz, 1H), 1.99-1.81 (m, 4H), 1.78 (d, J=11.55 Hz, 1H), 1.75-1.58 (m, 3H), 1.42 (d, J=12.10 Hz, 1H), 1.21-1.10 (m, 1H); 13C NMR (126 MHz, CDCl3) δ ppm 158.19, 148.93, 138.56, 129.11, 128.83, 126.89, 123.19, 119.35, 119.24, 62.75, 52.88, 52.68, 51.97, 50.82, 31.20, 28.69, 26.67, 23.96, 23.78, 21.47.

Example 40

1-((1R,2R)-2-((S)-1-(6-Methyl-5-nitropyridin-2-yl)piperidin-3-ylamino)cyclohexyl)-3-phenylurea

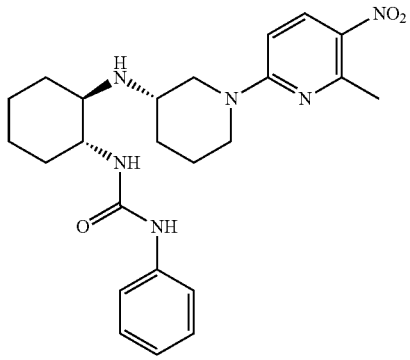 [SMILES: Cc1nc(N2CCC[C@H](N[C@@H]3CCCC[C@H]3NC(=O)Nc3ccccc3)C2)ccc1[N+](=O)[O-]]

1-((1R,2R)-2-((S)-1-(6-Methyl-5-nitropyridin-2-yl)piperidin-3-ylamino)cyclohexyl)-3-phenylurea was synthesized using 1-phenyl-3-((1R,2R)-2-(piperidin-3-ylamino)cyclohexyl)urea (from intermediate C, Example 1) (100 mg, 0.32 mmol) and 6-fluoro-2-methyl-3-nitropyridine (54.3 mg, 0.35 mmol) according to General Procedure A to give 20 mg (14%) of yellow solid. Anal. Calcd. for $C_{24}H_{32}N_6O_3$ m/z 452.2, found: 453.2 (M+H)+; 1H NMR (400 MHz, CD3OD) δ ppm 7.82 (d, J=9.4 Hz, 1H), 7.17 (m, 4H), 6.98 (m, 1H), 6.59 (d, J=9.4 Hz, 1H), 6.02 (d, J=4.6 Hz, 1H), 4.74 (m, 1H), 4.16 (m, 1H), 3.68 (m, 1H), 3.54 (m, 2H), 3.26 (m, 2H), 2.57 (s, 3H), 2.39 (m, 1H), 2.12 (m, 3H), 1.92 (m, 4H), 1.47 (m, 4H).

Example 41

1-((1R,2R)-2-((S)-1-(5-Nitropyridin-2-yl)piperidin-3-ylamino)cyclohexyl)-3-phenylurea

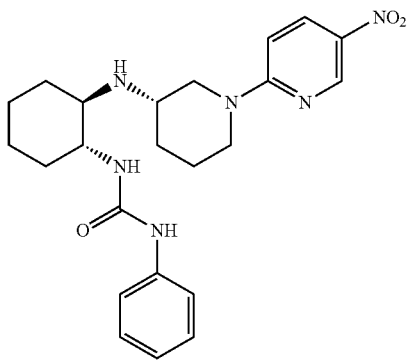 [SMILES: O=C(Nc1ccccc1)N[C@@H]1CCCC[C@H]1N[C@H]1CCCN(c2ccc([N+](=O)[O-])cn2)C1]

1-((1R,2R)-2-((S)-1-(5-Nitropyridin-2-yl)piperidin-3-ylamino)cyclohexyl)-3-phenylurea (40 mg, 0.097 mmol) was synthesized as described in Example 1 using 2-fluoro-5-nitropyridine in step D. Anal. Calcd. for $C_{23}H_{30}N_6O_3$ m/z 438.5, found: 439.3 (M+H)+; 1H NMR (500 MHz, CDCl3) δ ppm 9.91 (br. s., 1H), 8.95 (br. s., 1H), 8.76 (d, J=2.75 Hz, 1H), 7.78 (d, J=9.35 Hz, 1H), 7.23 (d, J=7.70 Hz, 2H), 7.16 (t, J=7.70 Hz, 2H), 6.96 (t, J=7.15 Hz, 1H), 6.69 (br. s., 1H), 6.36 (d, J=9.35 Hz, 1H), 4.20 (d, J=12.10 Hz, 1H), 3.90 (dd, J=12.37, 7.97 Hz, 1H), 3.80-3.60 (m, 2H), 3.36 (t, J=9.62 Hz, 1H), 3.18 (br. s., 1H), 2.99 (br. s., 1H), 2.19 (d, J=10.45 Hz, 1H), 2.11-1.96 (m, 2H), 1.96-1.77 (m, 3H), 1.74-1.53 (m, 3H), 1.39-1.09 (m, 3H); 13C NMR (126 MHz, CDCl3) δ ppm 159.95, 158.21, 145.97, 144.94, 138.57, 135.54, 133.07, 128.87, 123.14, 119.06, 104.99, 99.91, 62.46, 52.65, 52.01, 45.58, 45.13, 31.89, 31.60, 29.01, 28.33, 27.30, 23.86.

Example 42

1-((1R,2R)-2-((S)-1-(4-Cyanophenyl)piperidin-3-ylamino)cyclohexyl)-3-(4-fluorophenyl)urea

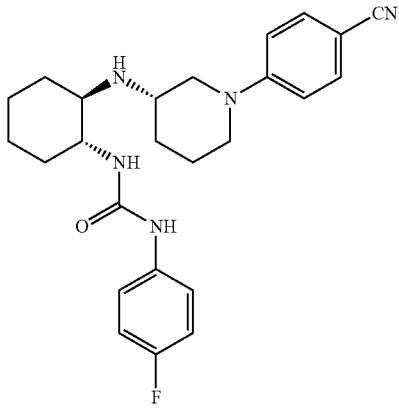 [SMILES: N#Cc1ccc(N2CCC[C@H](N[C@@H]3CCCC[C@H]3NC(=O)Nc3ccc(F)cc3)C2)cc1]

1-((1R,2R)-2-((S)-1-(4-Cyanophenyl)piperidin-3-ylamino)cyclohexyl)-3-(4-fluorophenyl)urea was synthesized using 4-((S)-3-((1R,2R)-2-aminocyclohexylamino)piperidin-1-yl)benzonitrile (from intermediate D, Example 10) (44.5 mg, 0.15 mmol) and 1-fluoro-4-isocyanatobenzene (20.4 mg, 0.15 mmol) according to General Procedure G to give 46 mg (70.8%) of pale yellow solid. Anal. Calcd. for $C_{25}H_{30}FN_5O$ m/z 435.2, found: 436.2 (M+H)+; 1H NMR (400 MHz, DMSO-d6) δ ppm 8.52 (s, 1H), 7.41 (m, 4H), 7.06 (t, J=8.9 Hz, 2H), 6.93 (d, J=9.1 Hz, 2H), 6.05 (d, J=7.8 Hz, 1H), 3.88 (d, J=11.6 Hz, 1H), 3.76 (d, J=12.7 Hz, 1H), 3.26 (m, 1H), 2.79 (m, 1H), 2.59 (m, 1H), 2.42 (m, 1H), 1.89 (m, 1H), 1.68 (m, 3H), 1.60 (m, 1H), 1.46 (m, 1H), 1.22 (m, 4H), 1.11 (m, 1H).

Example 43

Benzyl (1R,2R)-2-((S)-1-(4-(benzo[d]oxazol-2-yl)phenyl)piperidin-3-ylamino)cyclohexylcarbamate

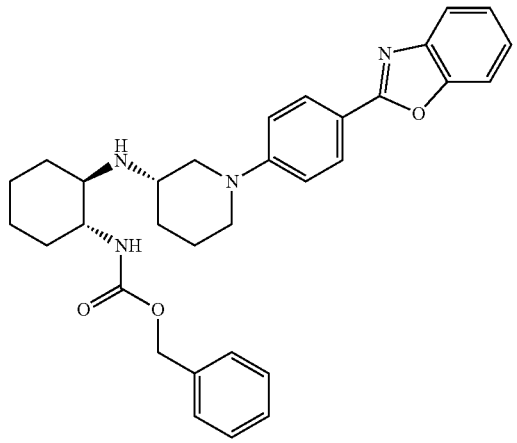 [SMILES: O=C(N[C@@H]1CCCC[C@H]1N[C@H]1CCCN(c2ccc(-c3nc4ccccc4o3)cc2)C1)OCc1ccccc1]

Benzyl (1R,2R)-2-((S)-1-(4-(benzo[d]oxazol-2-yl)phenyl)piperidin-3-ylamino)cyclohexylcarbamate was synthesized according to the procedure described for Example 15, using 2-(4-bromophenyl)benzo[d]oxazole in step A to give 4 mg of the title compound as an off-white solid. Anal. Calcd. for $C_{32}H_{36}N_4O_3$ m/z 524.5, found: 525.4 (M+H)+; 1H NMR (400 MHz, CDCl3) δ ppm 8.11 (d, J=8.6 Hz, 2H), 7.84-7.69 (m, 1H), 7.64-7.50 (m, 1H), 7.44-7.30 (m, 2H), 7.23-7.10 (m, 5H), 7.01 (d, J=8.6 Hz, 2H), 5.83-5.51 (s, 1H), 4.93-4.63 (m, 2H), 3.88-3.04 (m, 7H), 2.32-2.16 (m, 1H), 2.16-1.85 (m, 5H), 1.84-1.61 (m, 3H), 1.46-1.15 (m, 3H).

Example 44

Phenethyl (1R,2R)-2-((S)-1-(4-cyanophenyl)piperidin-3-ylamino)cyclohexylcarbamate

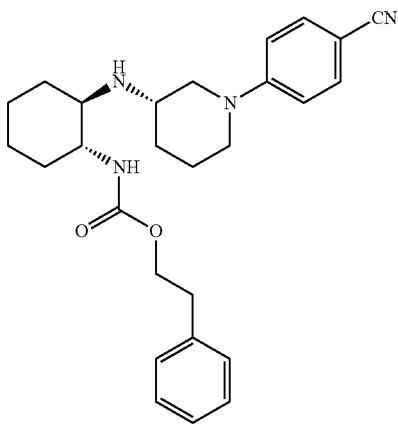 [SMILES: N#Cc1ccc(N2CCC[C@H](N[C@@H]3CCCC[C@H]3NC(=O)OCCc3ccccc3)C2)cc1]

Phenethyl(1R,2R)-2-((S)-1-(4-cyanophenyl)piperidin-3-ylamino)cyclohexylcarbamate was synthesized using 4-((S)-3-((1R,2R)-2-aminocyclohexylamino)piperidin-1-yl)benzonitrile (from intermediate D, Example 10) (50 mg, 0.17 mmol) and phenethyl carbonochloridate (52.9 mg, 0.18 mmol) according to General Procedure H to give 60 mg (80.4%) of pale yellow solid. Anal. Calcd. for $C_{27}H_{34}N_4O_2$ m/z 446.3, found: 447.2 (M+H)+; 1H NMR (400 MHz, DMSO-d6) δ ppm 7.54 (d, J=9 Hz, 2H), 7.24 (m, 5H), 6.98 (d, J=7 Hz, 3H), 4.13 (t, J=6.8 Hz, 2H), 3.89 (d, J=12.6 Hz, 1H), 3.76 (d, J=12.5 Hz, 1H), 3.05 (bs, 1H), 2.82 (m, 3H), 1.90 (m, 1H), 1.80 (m, 2H), 1.68 (m, 1H), 1.61 (m, 2H), 1.46 (m, 1H), 1.18-1.2 (m, 4H), 1.01 (m, 1H).

Example 45

1-((1R,2R)-2-((S)-1-(2-Cyanopyridin-4-yl)piperidin-3-ylamino)cyclohexyl)-3-phenylurea

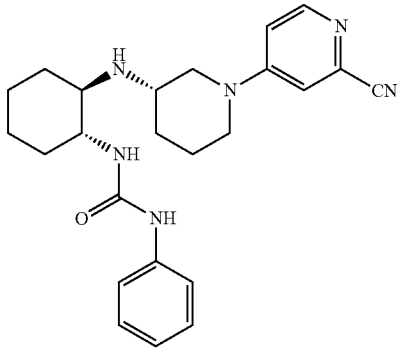 [SMILES: N#Cc1cc(N2CCC[C@H](N[C@@H]3CCCC[C@H]3NC(=O)Nc3ccccc3)C2)ccn1]

1-((1R,2R)-2-((S)-1-(2-Cyanopyridin-4-yl)piperidin-3-ylamino)cyclohexyl)-3-phenylurea was synthesized using 1-phenyl-3-((1R,2R)-2-(piperidin-3-ylamino)cyclohexyl)urea (from intermediate C, Example 1) (100 mg, 0.32 mmol) and 4-chloropicolinonitrile (44 mg, 0.15 mmol) according to General Procedure A to give 29.3 mg (22.1%) of pale brown oil. Anal. Calcd. for $C_{24}H_{30}N_6O$ m/z 418.2, found: 419.2 (M+H)+; 1H NMR (400 MHz, CD3OD) δ ppm 7.89 (d, J=6.5 Hz, 1H), 7.35 (d, J=2.7 Hz, 1H), 7.25 (m, 4H), 7.04 (m, 2H), 4.08 (m, 1H), 3.72 (m, 2H), 3.60 (m, 1H), 3.51 (m, 1H), 3.25 (m, 2H), 2.31 (m, 1H), 2.15-2.05 (m, 4H), 1.98-1.88 (m, 3H), 1.63-1.42 (m, 5H).

Example 46

2-((S)-3-((1R,2R)-2-(3-Phenylureido)cyclohexylamino)piperidin-1-yl)nicotinamide

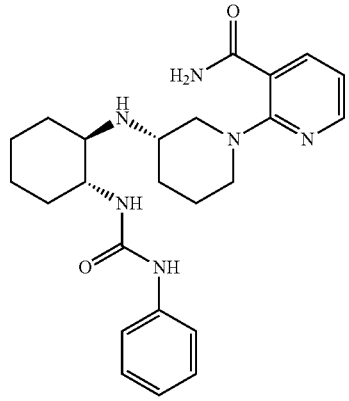 [SMILES: NC(=O)c1cccnc1N1CCC[C@H](N[C@@H]2CCCC[C@H]2NC(=O)Nc2ccccc2)C1]

2-((S)-3-((1R,2R)-2-(3-Phenylureido)cyclohexylamino)piperidin-1-yl)nicotinamide was synthesized using 1-phenyl-3-((1R,2R)-2-(piperidin-3-ylamino)cyclohexyl)urea (from intermediate C, Example 1) (100 mg, 0.32 mmol) and 2-chloronicotinamide (49 mg, 0.32 mmol) according to General Procedure A to give 9 mg (6.5%) of pale brown oil. Anal. Calcd. for $C_{24}H_{32}N_6O_2$ m/z 436.3, found: 437.2 (M+H)+; 1H NMR (400 MHz, CD3OD) δ ppm 8.2 (d, J=3.8 Hz, 1H), 7.65 (dd, J=2 Hz, 1H), 7.21 (m, 4H), 7.01 (m, 1H), 6.86 (m, 1H), 3.66 (m, 4H), 3.21 (m, 3H), 2.35 (m, 1H), 2.10 (m, 2H), 1.89 (m, 4H), 1.74 (m, 1H), 1.68 (d, J=1.68 Hz, 1H), 1.60 (m, 1H), 1.45 (m, 3H).

Example 47

1-((1R,2R)-2-((S)-1-(4-Nitrophenyl)piperidin-3-ylamino)cyclohexyl)-3-(6-(trifluoromethyl)pyridin-3-yl)urea

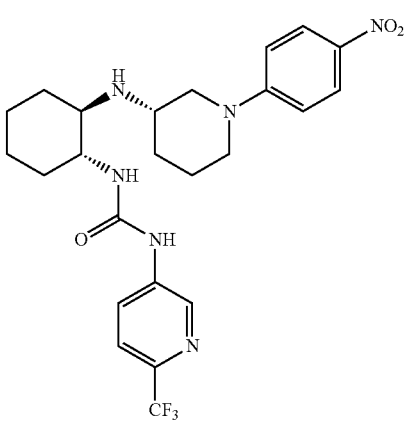 [SMILES: O=C(Nc1ccc(C(F)(F)F)nc1)N[C@@H]1CCCC[C@H]1N[C@H]1CCCN(c2ccc([N+](=O)[O-])cc2)C1]

1-((1R,2R)-2-((S)-1-(4-Nitrophenyl)piperidin-3-ylamino)cyclohexyl)-3-(6-(trifluoromethyl)pyridin-3-yl)urea was synthesized according to the procedure described in Example 2, using 5-isocyanato-2-(trifluoromethyl)pyridine (28.7 mg, 0.153 mmol) to give 43 mg (53.8% yield) of the title compound as a yellow solid. Anal. Calcd. for $C_{24}H_{29}F_3N_6O_3$ m/z 506.5, found: 507.3 (M+H)$^+$; $^1$H NMR (500 MHz, CDCl$_3$) δ ppm 9.76 (br. s., 1H), 9.58 (br. s., 1H), 9.12 (br. s., 1H), 8.81 (d, J=4.95 Hz, 1H), 7.67 (br. s., 1H), 7.55 (d, J=8.25 Hz, 1H), 7.47 (d, J=8.80 Hz, 2H), 7.42 (br. s., 1H), 6.52 (d, J=9.35 Hz, 2H), 3.80 (dd, J=13.47, 4.67 Hz, 1H), 3.70 (br. s., 1H), 3.59-3.45 (m, 3H), 3.46-3.31 (m, 3H), 3.19 (br. s., 1H), 2.30 (d, J=11.55 Hz, 1H), 2.22-2.03 (m, 3H), 1.99-1.74 (m, 4H), 1.73-1.51 (m, 2H), 1.39-1.31 (m, 2H).

Example 48

1-((1R,2R)-2-((S)-1-(4-Cyanophenyl)piperidin-3-ylamino)cyclohexyl)-3-p-tolylurea

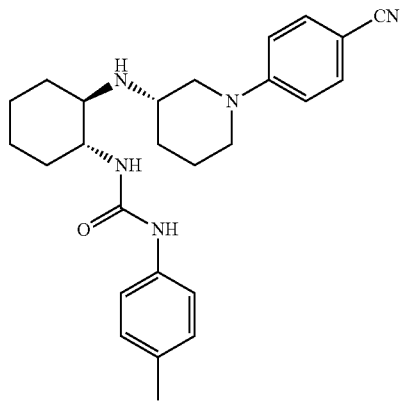 [SMILES: Cc1ccc(NC(=O)N[C@@H]2CCCC[C@H]2N[C@H]2CCCN(c3ccc(C#N)cc3)C2)cc1]

1-((1R,2R)-2-((S)-1-(4-Cyanophenyl)piperidin-3-ylamino)cyclohexyl)-3-p-tolylurea was synthesized using 4-((S)-3-((1R,2R)-2-aminocyclohexylamino)piperidin-1-yl)benzonitrile (from intermediate D, Example 10) (66 mg, 0.22 mmol) and 1-isocyanato-4-methylbenzene (29.4 mg, 0.22 mmol) according to General Procedure G to give 30 mg (31.4%) of white solid. Anal. Calcd. for $C_{26}H_{33}N_5O$ m/z 431.3, found: 432.2 (M+H)$^+$; $^1$H NMR (400 MHz, DMSO-d$_6$) δ ppm 8.38 (m, 2H), 7.39 (d, J=8.9 Hz, 2H), 7.25 (m, 2H), 7.03 (d, J=8.3 Hz, 2H), 6.93 (d, J=7.6 Hz, 2H), 6.02 (s, 1H), 3.81 (m, 2H), 2.22 (s, 3H), 1.91 (m, 3H), 1.64 (m, 4H), 1.48 (m, 2H), 1.2 (m, 5H), 1.19 (m, 1H).

Example 49

1-Phenyl-3-((1R,2R)-2-((S)-1-(5-(trifluoromethyl)pyridin-2-yl)piperidin-3-ylamino)cyclohexyl)urea

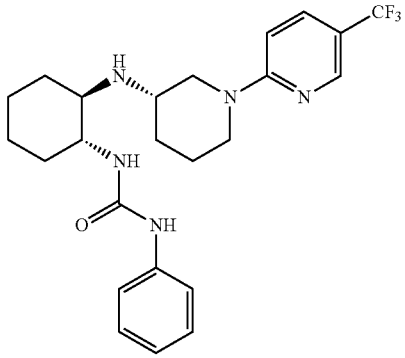 [SMILES: O=C(Nc1ccccc1)N[C@@H]1CCCC[C@H]1N[C@H]1CCCN(c2ccc(C(F)(F)F)cn2)C1]

1-Phenyl-3-((1R,2R)-2-((S)-1-(5-(trifluoromethyl)pyridin-2-yl)piperidin-3-ylamino)cyclohexyl)urea was synthesized using 1-phenyl-3-((1R,2R)-2-(piperidin-3-ylamino)cyclohexyl)urea (from intermediate C, Example 1) (100 mg, 0.32 mmol) and 2-fluoro-5-(trifluoromethyl)pyridine (57.4 mg, 0.35 mmol) according to General Procedure A to give 15 mg (10.3%) of white solid. Anal. Calcd. for $C_{24}H_{30}F_3N_5O$ m/z 461.2, found: 462.2 (M+H)$^+$; $^1$H NMR (400 MHz, CD$_3$OD) δ ppm 8.18 (m, 1H), 7.30 (m, 1H), 7.21 (m, 4H), 7.00 (m, 1H), 6.67 (d, J=8.9 Hz, 1H), 6.18 (d, J=5.4 Hz, 1H), 4.47 (m, 1H), 3.79 (m, 1H), 3.59 (m, 3H), 3.23 (m, 1H), 2.33 (m, 1H), 2.07 (m, 4H), 1.87 (m, 3H), 1.67 (d, J=7 Hz, 2H), 1.49 (m, 4H).

Example 50

1-((1R,2R)-2-(Methyl((S)-1-(4-nitrophenyl)piperidin-3-yl)amino)cyclohexyl)-3-phenylurea

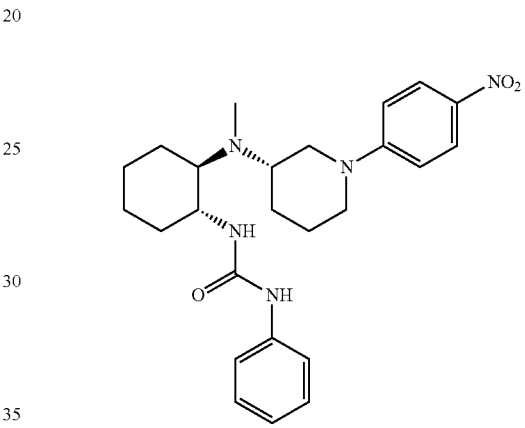

To a round bottom flask was added 1-((1R,2R)-2-((S)-1-(4-nitrophenyl)piperidin-3-ylamino)cyclohexyl)-3-phenylurea (prepared as described in Example 1) (30 mg, 0.069 mmol), formaldehyde (0.079 mL, 1.028 mmol) (37% in water), acetic acid (0.2 mL), CH$_2$Cl$_2$ (1 mL) and NaSO$_4$ (3 gms). The reaction was stirred at rt for 2 hrs. Then sodium cyanoborohydride (21.54 mg, 0.343 mmol) was added to the reaction and the reaction was stirred for an additional 1 hr. After this time, the reaction was quenched with water (2 ml). The reaction was partitioned between CH$_2$Cl$_2$ (15 ml) and saturated aqueous NaHCO$_3$ (10 ml). The organic layer was washed with water (10 ml) and saturated aqueous NaCl (10 ml). The organic layer was dried over MgSO$_4$, filtered and concentrated. The residue was purified by RP prep-HPLC (Method A). The desired fractions were concentrated to give the product, 1-((1R,2R)-2-(methyl((S)-1-(4-nitrophenyl)piperidin-3-yl)amino)cyclohexyl)-3-phenylurea (18 mg, 0.038 mmol, 55.2% yield) as a yellow solid. Anal. Calcd. for $C_{25}H_{33}N_5O_3$ m/z 451.5, found: 452.3 (M+H)$^+$; $^1$H NMR (500 MHz, CDCl$_3$) δ ppm 10.60 (br. s., 1H), 7.89 (d, J=8.80 Hz, 2H), 7.52 (br. s., 1H), 7.33 (d, J=8.25 Hz, 2H), 7.30-7.19 (m, 2H), 7.03 (t, J=7.15 Hz, 1H), 6.75 (d, J=8.80 Hz, 2H), 3.87-3.56 (m, 4H), 3.51-3.34 (m, 4H), 3.23-3.13 (m, 1H), 2.82 (br. s., 3H), 2.25-1.32 (m, 10H); $^{13}$C NMR (126 MHz, CDCl$_3$) δ ppm 158.25, 154.02, 139.91, 138.67, 128.85, 125.71, 123.04, 118.88, 114.37, 68.41, 60.22, 50.63, 48.67, 48.25, 32.33, 31.60, 25.29, 25.13, 24.18, 23.74, 22.28.

Example 51

1-(3-Chlorophenyl)-3-((1R,2R)-2-((S)-1-(4-cyanophenyl)piperidin-3-ylamino)cyclohexyl)urea

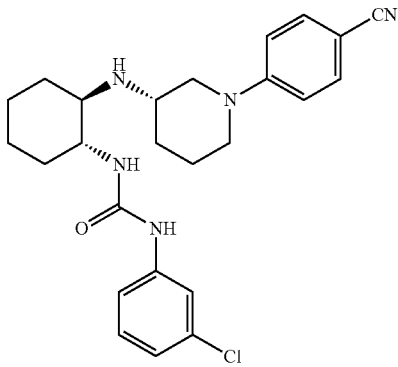 [SMILES: N#Cc1ccc(N2CCC[C@H](N[C@@H]3CCCC[C@H]3NC(=O)Nc3cccc(Cl)c3)C2)cc1]

1-(3-Chlorophenyl)-3-((1R,2R)-2-((S)-1-(4-cyanophenyl)piperidin-3-ylamino)cyclohexyl)urea was synthesized using 4-((S)-3-((1R,2R)-2-aminocyclohexylamino)piperidin-1-yl)benzonitrile (from intermediate D, Example 10) (60 mg, 0.20 mmol) and 1-chloro-3-isocyanatobenzene (30.9 mg, 0.20 mmol) according to General Procedure G to give 20 mg (22%) of a white solid. Anal. Calcd. for $C_{25}H_{30}ClN_5O$ m/z 451.2, found: 452.2 (M+H)$^+$; $^1$H NMR (400 MHz, DMSO-$d_6$) δ ppm 9.00 (s, 1H), 7.66 (s, 1H), 7.43 (d, J=8.9 Hz, 2H), 7.24 (t, J=8.0 Hz, 1H), 7.17 (d, J=8 Hz, 1H), 6.95 (m, 3H), 6.45 (bs, 1H), 3.88 (d, J=11.3 Hz, 1H), 3.72 (d, J=12.6 Hz, 1H), 2.84 (m, 4H), 1.97 (m, 4H), 1.68 (m, 3H), 1.50 (m, 4H), 1.25 (m, 2H).

Example 52

1-((1R,2R)-2-((S)-1-(4-Nitrophenyl)azepan-4-ylamino)cyclohexyl)-3-phenylurea

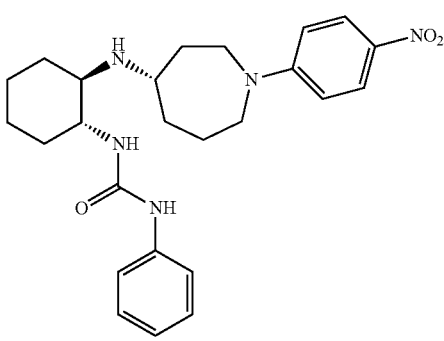 [SMILES: O=C(Nc1ccccc1)N[C@@H]1CCCC[C@H]1N[C@H]1CCCN(c2ccc([N+](=O)[O-])cc2)CC1]

A: 1-(4-Nitrophenyl)azepan-4-ol

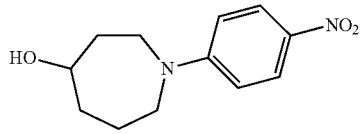 [SMILES: O=[N+]([O-])c1ccc(N2CCCC(O)CC2)cc1]

To a round bottom flask was added azepan-4-ol (300 mg, 2.60 mmol), 1-fluoro-4-nitrobenzene (368 mg, 2.60 mmol), $Cs_2CO_3$ (1018 mg, 3.13 mmol) and DMF (5 mL). The reaction was stirred at 100° C. for 10 hrs. The reaction was diluted with EtOAc (50 ml), washed with water (4×20 ml) and saturated aqueous NaCl (25 ml). The organic layer was dried over $MgSO_4$, filtered and concentrated. The resulting residue was purified using silica gel chromatography (ISCO system) eluting with a gradient of 0-100% EtOAc/He) to give the product, 1-(4-nitrophenyl)azepan-4-ol (480 mg, 2.032 mmol, 78% yield) as a light yellow solid. Anal. Calcd. for $C_{12}H_{16}N_2O_3$ m/z 236.2, found: 237.1 (M+H)$^+$; $^1$H NMR (400 MHz, CDCl$_3$) δ ppm 8.18-8.03 (m, 2H), 6.71-6.57 (m, 2H), 4.00 (br. s., 1H), 3.74-3.60 (m, 1H), 3.60-3.41 (m, 3H), 2.22-2.01 (m, 2H), 1.95-1.72 (m, 4H); $^{13}$C NMR (101 MHz, CDCl$_3$) δ ppm 153.41, 136.89, 126.38, 110.02, 69.88, 49.24, 44.00, 35.87, 34.96, 21.59.

B: 1-(4-Nitrophenyl)azepan-4-one

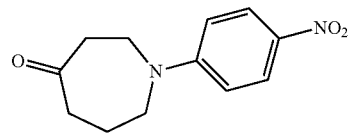 [SMILES: O=C1CCCN(c2ccc([N+](=O)[O-])cc2)CC1]

To a dry round bottom flask was added 2M oxalyl chloride (1.392 mL, 2.78 mmol) and $CH_2Cl_2$ (10 mL). The resulting solution was cooled to −78° C. DMSO (0.395 mL, 5.57 mmol) was then slowly added to the solution over 10 min. The reaction was stirred at −78° C. for 20 mins. Then 1-(4-nitrophenyl)azepan-4-ol (470 mg, 1.989 mmol) dissolved in $CH_2Cl_2$ (5 ml) was added to the reaction and the reaction was stirred at −78° C. for 1.5 hr. After this time, Et$_3$N (1.220 mL, 8.75 mmol) was added to the reaction mixture. The reaction mixture was then diluted with $CH_2Cl_2$ (30 ml). The reaction mixture was washed with water (20 ml) and saturated aqueous NaCl (20 ml). The organic layer was separated, dried over $MgSO_4$, filtered and concentrated. The resulting residue was purified using silica gel chromatography (ISCO system) eluting with a gradient of 0-100% EtOAc/Hex to give the product, 1-(4-nitrophenyl)azepan-4-one (392 mg, 1.673 mmol, 84% yield) as a yellow solid. Anal. Calcd. for $C_{12}H_{14}N_2O_3$ m/z 234.2, found: 235.1 (M+H)$^+$; $^1$H NMR (500 MHz, CDCl$_3$) δ ppm 8.12 (d, J=9.35 Hz, 2H), 6.66 (d, J=9.35 Hz, 2H), 3.95-3.83 (m, 2H), 3.83-3.72 (m, 2H), 2.92-2.66 (m, 4H), 2.02-1.86 (m, 2H); $^{13}$C NMR (126 MHz, CDCl$_3$) δ ppm 209.79, 151.25, 137.70, 126.52, 110.45, 51.82, 45.39, 42.64, 41.79, 23.88.

C: (1R,2R)—N1-(1-(4-Nitrophenyl)azepan-4-yl)cyclohexane-1,2-diamine

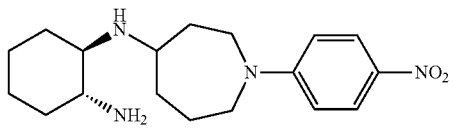 [SMILES: N[C@@H]1CCCC[C@H]1NC1CCCN(c2ccc([N+](=O)[O-])cc2)CC1]

To a round bottom flask under argon was added the (1R,2R)-cyclohexane-1,2-diamine (216 mg, 1.895 mmol), $CH_2Cl_2$ (10 mL), solid anhydrous $Na_2SO_4$ (10 gm). Argon was bubbled through the reaction mixture for 1 min and then the reaction was stirred under argon at rt for 1 hr. After this time, sodium triacetoxy borohydride (1 gm, 4.74 mmol) was added and the reaction was then stirred at rt for an additional 2 hrs. After this time, the reaction was quenched with saturated aqueous NaHCO₃ (3 ml). The reaction mixture was then diluted with CH₂Cl₂ (50 ml). The layers were separated and the organic layer was washed with water (50 ml) and saturated aqueous NaCl (50 ml). The organic layer was separated, dried over MgSO₄, filtered and concentrated to give the product, (1R,2R)—N1-(1-(4-nitrophenyl)azepan-4-yl)cyclohexane-1,2-diamine (300 mg, 0.902 mmol, 57.1% yield) as a yellow solid. Anal. Calcd. for $C_{18}F'_{28}N_4O_2$ m/z 332.4, found: 333.2 (M+H)⁺; ¹H NMR (500 MHz, CDCl₃) δ ppm 8.25-7.95 (m, 2H), 6.77-6.45 (m, 2H), 3.81-3.30 (m, 4H), 3.00-2.70 (m, 1H), 2.50-2.26 (m, 1H), 2.21-1.96 (m, 8H), 1.96-1.60 (m, 8H), 1.58-1.34 (m, 1H), 1.34-1.09 (m, 3H), 1.06-0.75 (m, 1H).

D: 1-((1R,2R)-2-((S)-1-(4-Nitrophenyl)azepan-4-ylamino)cyclohexyl)-3-phenylurea

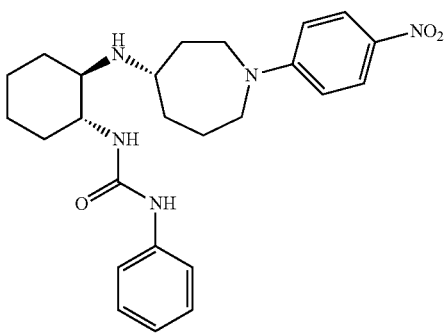 [SMILES: O=C(Nc1ccccc1)N[C@@H]1CCCC[C@H]1N[C@H]1CCCN(c2ccc([N+](=O)[O-])cc2)CC1]

To a round bottom flask was added (1R,2R)—N1-(1-(4-nitrophenyl)azepan-4-yl)cyclohexane-1,2-diamine (70 mg, 0.211 mmol), THF (3 mL), and Et₃N (0.029 mL, 0.211 mmol). To the resulting solution was added isocyanatobenzene (25.08 mg, 0.211 mmol). The reaction was stirred at rt overnight. After this time, the reaction mixture was concentrated. The resulting crude product was purified by RP prep-HPLC to give a mixture of 2 diastereomers. The mixture of two diastereomers was separated by chiral HPLC (chiral separation method A) to give the desired product, 1-((1R,2R)-2-((S)-1-(4-nitrophenyl)azepan-4-ylamino)cyclohexyl)-3-phenylurea (7 mg, 0.019 mmol, 6.7% yield) as a yellow solid. Anal. Calcd. for $C_{25}H_{33}N_5O_3$ m/z 451.5, found: 452.3 (M+H)⁺; ¹H NMR (500 MHz, CDCl₃) δ ppm 8.10 (d, J=9.35 Hz, 2H), 7.30-7.27 (m, 2H), 7.22 (t, J=7.70 Hz, 2H), 6.99 (t, J=7.15 Hz, 1H), 6.60 (d, J=9.35 Hz, 2H), 4.57 (br. s., 1H), 3.66-3.53 (m, 2H), 3.53-3.45 (m, 1H), 3.44-3.35 (m, 1H), 3.21 (d, J=4.95 Hz, 1H), 2.85-2.73 (m, 1H), 2.24 (td, J=10.31, 3.57 Hz, 1H), 2.09 (d, J=9.35 Hz, 2H), 1.97 (d, J=12.10 Hz, 1H), 1.90 (d, J=11.55 Hz, 2H), 1.73 (d, J=9.90 Hz, 2H), 1.69-1.61 (m, 2H), 1.44-1.34 (m, 2H), 1.23-1.07 (m, 3H); ¹³C NMR (126 MHz, CDCl₃) δ ppm 157.11, 153.29, 139.21, 136.84, 129.12, 126.49, 123.13, 120.06, 110.01, 60.75, 56.99, 56.15, 49.50, 45.82, 34.95, 33.49, 33.29, 32.63, 25.06, 24.85, 23.76.

Example 53

1-((1R,2R)-2-((S)-1-(4-Cyanophenyl)piperidin-3-ylamino)cyclohexyl)-3-m-tolylurea

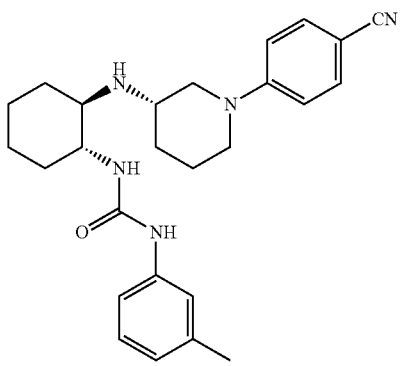

1-((1R,2R)-2-((S)-1-(4-Cyanophenyl)piperidin-3-ylamino)cyclohexyl)-3-m-tolylurea was synthesized using 4-((S)-3-((1R,2R)-2-aminocyclohexylamino)piperidin-1-yl)benzonitrile (from intermediate D, Example 10) (50 mg, 0.17 mmol) and 1-isocyanato-3-methylbenzene (22.3 mg, 0.17 mmol) according to General Procedure G to give 20 mg (27.7%) of a white solid. Anal. Calcd. for $C_{26}H_{33}N_5O$ m/z 431.3, found: 432.2 (M+H)⁺; ¹H NMR (400 MHz, DMSO-d₆) δ ppm 8.47 (s, 1H), 7.39 (d, J=8.9 Hz, 2H), 7.20 (s, 2H), 7.10 (t, J=8.1 Hz, 1H), 6.92 (d, J=8.9 Hz, 2H), 6.71 (d, J=7.4 Hz, 1H), 6.15 (d, J=7.6 Hz, 1H), 3.89 (d, J=11.1 Hz, 1H), 3.77 (d, J=13.2 Hz, 1H), 3.26 (d, J=8.9 Hz, 1H), 2.79 (m, 1H), 2.57 (m, 1H), 2.42 (m, 1H), 2.24 (s, 1H), 1.88 (m, 3H), 1.65 (m, 4H), 1.45 (m, 1H), 1.21 (m, 4H), 1.11 (m, 1H).

Example 54

1-((1R,2R)-2-((S)-1-(5-Cyanopyridin-2-yl)piperidin-3-ylamino)cyclohexyl)-3-phenylurea

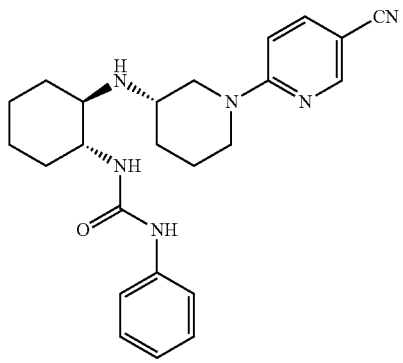

1-((1R,2R)-2-((S)-1-(5-Cyanopyridin-2-yl)piperidin-3-ylamino)cyclohexyl)-3-phenylurea (30 mg, 0.067 mmol) was synthesized as described in Example 1 using 6-fluoronicotinonitrile in step D. Anal. Calcd. for $C_{24}H_{30}N_6O$ m/z 418.5, found: 419.3 (M+H)⁺; ¹H NMR (500 MHz, CDCl₃) δ ppm 9.62 (br. s., 1H), 8.42 (br. s., 1H), 8.12 (s, 1H), 7.25-7.06 (m, 4H), 6.91 (t, J=7.15 Hz, 1H), 6.38 (d, J=8.80 Hz, 1H), 4.04 (d, J=12.65 Hz, 1H), 3.86-3.71 (m, 1H), 3.66-3.47 (m, 2H), 3.28 (d, J=9.35 Hz, 1H), 3.14 (br. s., 1H), 2.98 (br. s., 1H), 2.14 (d, J=10.45 Hz, 1H), 2.01-1.87 (m, 2H), 1.79 (t, J=13.47 Hz, 3H), 1.64 (d, J=10.45 Hz, 1H), 1.60-1.43 (m, 2H), 1.32-1.07 (m, 3H); $^{13}$C NMR (126 MHz, CDCl$_3$) δ ppm 158.65, 158.03, 152.06, 140.17, 138.31, 128.93, 123.43, 119.34, 117.89, 116.94, 114.63, 106.50, 97.63, 62.18, 52.65, 51.78, 45.37, 44.89, 31.58, 28.27, 27.44, 23.70, 22.69, 21.84.

Example 55

1-((1R,2R)-2-((S)-1-(4-Cyanophenyl)piperidin-3-ylamino)cyclohexyl)-3-(4-methoxyphenyl)urea

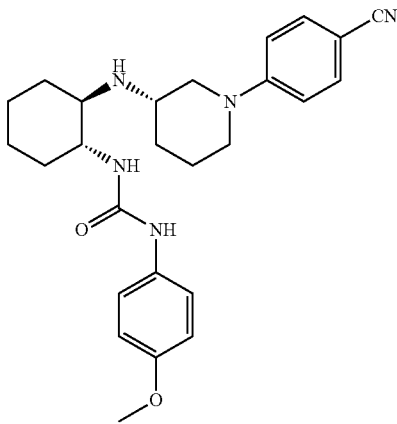 [SMILES: COc1ccc(NC(=O)N[C@@H]2CCCC[C@H]2N[C@H]2CCCN(c3ccc(C#N)cc3)C2)cc1]

1-((1R,2R)-2-((S)-1-(4-Cyanophenyl)piperidin-3-ylamino)cyclohexyl)-3-(4-methoxyphenyl)urea was synthesized using 4-((S)-3-((1R,2R)-2-aminocyclohexylamino)piperidin-1-yl)benzonitrile (from intermediate D, Example 10) (55 mg, 0.18 mmol) and 1-isocyanato-4-methoxybenzene (27.5 mg, 0.18 mmol) according to General Procedure G to give 20 mg (24.2%) of a white solid. Anal. Calcd. for C$_{26}$H$_{33}$N$_5$O$_2$ m/z 447.3, found: 448.2 (M+H)$^+$; $^1$H NMR (400 MHz, DMSO-d$_6$) δ ppm 8.28 (s, 1H), 7.41 (d, J=9 Hz, 2H), 7.29 (d, J=9 Hz, 2H), 6.92 (d, J=9 Hz, 2H), 6.82 (d, J=3 Hz, 2H), 5.95 (d, J=7.6 Hz, 1H), 3.89 (d, m, 1H), 3.77 (m, 1H), 3.70 (s, 3H), 3.26 (m, 1H), 2.79 (m, 1H), 2.60 (m, 1H), 2.40 (m, 1H), 1.89 (m, 3H), 1.68 (m, 1H), 1.60 (m, 2H), 1.45 (m, 1H), 1.23 (m, 6H), 1.10 (m, 1H).

Example 56

1-((1R,2R)-2-((S)-1-(4-Cyanophenyl)piperidin-3-ylamino)cyclohexyl)-3-(4-(trifluoromethyl)phenyl)urea

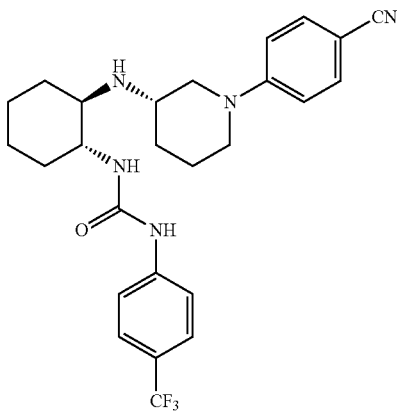 [SMILES: N#Cc1ccc(N2CCC[C@H](N[C@@H]3CCCC[C@H]3NC(=O)Nc3ccc(C(F)(F)F)cc3)C2)cc1]

1-((1R,2R)-2-((S)-1-(4-Cyanophenyl)piperidin-3-ylamino)cyclohexyl)-3-(4-(trifluoromethyl)phenyl)urea was synthesized using 4-((S)-3-((1R,2R)-2-aminocyclohexylamino)piperidin-1-yl)benzonitrile (from intermediate D, Example 10) (50 mg, 0.17 mmol) and 1-isocyanato-4-(trifluoromethyl)benzene (31.3 mg, 0.17 mmol) according to General Procedure G to give 18 mg (22.1%) of white solid. Anal. Calcd. for C$_{26}$H$_{30}$F$_3$N$_5$O m/z 458.2, found: 486.3 (M+H)$^+$; $^1$H NMR (400 MHz, CD$_3$OD) δ ppm 7.53 (d, J=8.8 Hz, 2H), 7.45 (d, J=8.6 Hz, 2H), 7.25 (d, J=9 Hz, 2H), 6.88 (d, J=9 Hz, 2H), 3.64 (m, 1H), 3.51 (m, 2H), 3.05 (m, 1H), 2.70 (m, 1H), 2.12 (m, 1H), 1.99 (m, 3H), 1.83 (m, 3H), 1.67 (m, 3H), 1.39 (m, 6H).

Example 57

Benzyl (1R,2R)-2-((S)-1-(4-(oxazol-5-yl)phenyl)piperidin-3-ylamino)cyclohexylcarbamate

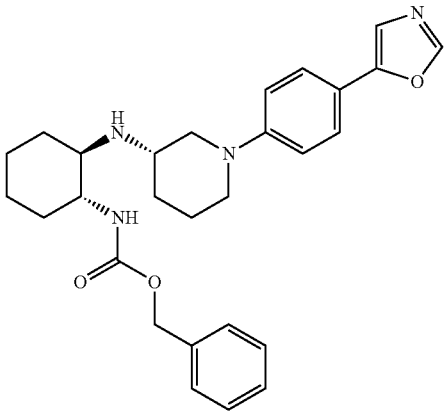 [SMILES: O=C(N[C@@H]1CCCC[C@H]1N[C@H]1CCCN(c2ccc(-c3cnco3)cc2)C1)OCc1ccccc1]

Benzyl (1R,2R)-2-((S)-1-(4-(oxazol-5-yl)phenyl)piperidin-3-ylamino)cyclohexylcarbamate was synthesized according to the method of Example 7, using 5-(4-bromophenyl)oxazole in step A to give 7.1 mg of the title compound as an off-white solid. Anal. Calcd. for C$_{28}$H$_{34}$N$_4$O$_3$ m/z 474.5, found: 475.3 (M+H)$^+$; $^1$H NMR (400 MHz, CDCl$_3$) δ ppm 7.93 (s, 1H), 7.51 (d, J=8.7 Hz, 2H), 7.26-7.21 (m, 3H), 7.20 (s, 1H), 7.16-7.06 (m, 2H), 7.00 (d, J=8.7 Hz, 2H), 5.73 (s, 1H), 4.76 (d, J=12.4 Hz, 1H), 4.56 (d, J=12.5 Hz, 1H), 3.63-3.35 (m, 4H), 3.35-3.14 (m, 2H), 3.13-2.97 (m, 1H), 2.29-2.05 (m, 2H), 2.02-1.84 (m, 4H), 1.84-1.63 (m, 4H), 1.42-1.18 (m, 2H).

Example 58

Benzyl (1R,2R)-2-((S)-3-methyl-1-(4-nitrophenyl)piperidin-3-ylamino)cyclohexylcarbamate

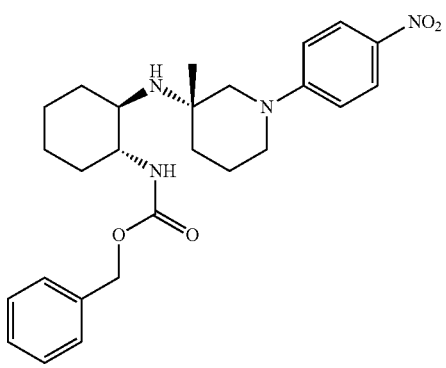 [SMILES: C[C@]1(N[C@@H]2CCCC[C@H]2NC(=O)OCc2ccccc2)CCCN(c2ccc([N+](=O)[O-])cc2)C1]

A: 1-Benzyl 3-ethyl piperidine-1,3-dicarboxylate

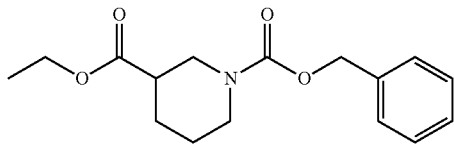 [SMILES: CCOC(=O)C1CCCN(C(=O)OCc2ccccc2)C1]

To a solution of ethyl piperidine-3-carboxylate (4 g, 25.4 mmol) in THF (30 mL) and water (30.0 mL) was added Na$_2$CO$_3$ (6.74 g, 63.6 mmol). The resulting suspension was stirred at rt for 20 min. After this time, benzyl carbonochloridate (4.12 g, 24.17 mmol) was added dropwise. After addition, the stirring solution became milky, and a white precipitate formed. After stirring at rt for 2 h, the reaction was partitioned between EtOAc and water. The separated aqueous phase was extracted with EtOAc (2×). The combined organics were washed with water and saturated aqueous NaCl. The organic layer was dried over Na$_2$SO$_4$, filtered and concentrated. The oily residue was purified using silica gel chromatography (ISCO system) eluting with a gradient of 0-40% EtOAc/Hex. The desired fractions were concentrated to afford the desired product, 1-benzyl 3-ethyl piperidine-1,3-dicarboxylate (5.68 g, 19.50 mmol, 77% yield) as a colorless oil. Anal. Calcd. for C$_{16}$H$_{21}$NO$_4$ m/z 291.3, found: 292.1 (M+H)$^+$; $^1$H NMR (400 MHz, CDCl$_3$) δ ppm 7.41-7.28 (m, 5H), 5.26-4.97 (m, 2H), 4.34-4.06 (m, 3H), 4.06-3.91 (m, 1H), 3.13 (br. s., 1H), 2.96-2.81 (m, 1H), 2.46 (br. s., 1H), 2.15-1.96 (m, 1H), 1.78-1.56 (m, 2H), 1.49 (br. s., 1H), 1.33-1.17 (m, 3H).

B: 1-Benzyl 3-ethyl 3-methylpiperidine-1,3-dicarboxylate

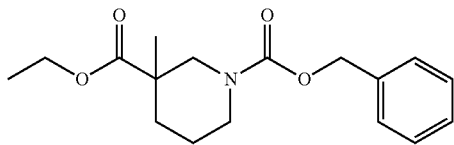 [SMILES: CCOC(=O)C1(C)CCCN(C(=O)OCc2ccccc2)C1]

To a solution of 1-benzyl 3-ethyl piperidine-1,3-dicarboxylate (2.107 g, 7.23 mmol) in dry THF (22 mL) and DMPU (1.4 mL, 1160 mmol) at −78° C. was added dropwise lithium bis(trimethylsilyl)amide (1.271 g, 7.59 mmol, 7.60 mL of 1M solution in THF). After addition, the reaction mixture was stirred at −60° C. for 1 h. Then iodomethane (0.520 mL, 8.32 mmol) in DMPU (0.344 mL, 2.86 mmol) was added dropwise. After addition, the reaction was stirred at −60° C. for 1.5 h, then slowly warmed up to −20° C. over approximately 1 hr. The reaction was quenched by the addition of saturated aqueous NH$_4$Cl. The reaction solution was extracted with EtOAc (2×). The combined organics were washed with saturated aqueous NH$_4$Cl and saturated aqueous NaCl. The organic layer was dried over Na$_2$SO$_4$, filtered and concentrated. The residue was purified using silica gel chromatography (ISCO system) eluting with a gradient of 0-30% EtOAc/Hex. The desired fractions were concentrated to give the product, benzyl 3-ethyl 3-methylpiperidine-1,3-dicarboxylate (1.66 gm, 5.44 mmol, 75.2% yield) as a light brown oil. Anal. Calcd. for C$_{17}$H$_{23}$NO$_4$ m/z 305.3, found: 306.2 (M+H)$^+$; $^1$H NMR (400 MHz, CDCl$_3$) δ ppm 7.44-7.27 (m, 5H), 5.20-5.09 (m, 2H), 4.24-4.04 (m, 2H), 3.99 (d, J=13.19 Hz, 1H), 3.59 (br. s., 1H), 3.27 (d, J=7.15 Hz, 1H), 3.13 (d, J=12.64 Hz, 1H), 2.16-1.95 (m, 1H), 1.74-1.52 (m, 2H), 1.51-1.39 (m, 1H), 1.25-1.07 (m, 6H).

C: Ethyl 3-methylpiperidine-3-carboxylate

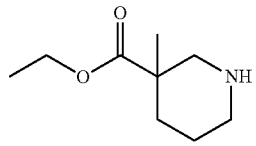

A suspension of 1-benzyl 3-ethyl 3-methylpiperidine-1,3-dicarboxylate (3.945 g, 12.92 mmol) and 5% Pd/C (800 mg) in ethyl acetate (20 mL) and methanol (20.00 mL) was vigorously stirred under a hydrogen balloon for 1.5 hr. The reaction mixture was filtered to remove the catalyst and the filtrate was concentrated to dryness to give the desired crude product ethyl 3-methylpiperidine-3-carboxylate (2.010 g, 11.74 mmol, 91% yield) as a colorless oily residue. Anal. Calcd. for C$_9$H$_{17}$NO$_2$ m/z 171.2, found: 172.2 (M+H)$^+$; $^1$H NMR (400 MHz, CDCl$_3$) δ ppm 4.25-4.06 (m, 2H), 3.31 (d, J=13.19 Hz, 1H), 2.93 (d, J=13.19 Hz, 1H), 2.59 (d, J=10.44 Hz, 1H), 2.41 (d, J=13.19 Hz, 1H), 2.23-2.11 (m, 1H), 1.68 (br. s., 1H), 1.52 (t, J=3.85 Hz, 1H), 1.46-1.31 (m, 2H), 1.27 (t, J=7.15 Hz, 3H), 1.10 (s, 3H).

D: Ethyl 3-methyl-1-(4-nitrophenyl)piperidine-3-carboxylate

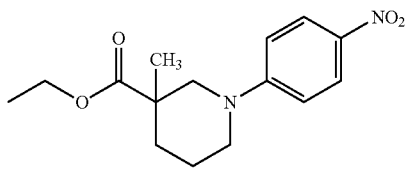 [SMILES: CCOC(=O)C1(C)CCCN(c2ccc([N+](=O)[O-])cc2)C1]

To a round bottom flask was added ethyl 3-methylpiperidine-3-carboxylate (2.040 g, 11.91 mmol), 1-fluoro-4-nitrobenzene (1.765 g, 12.51 mmol), DMF (20 ml) and K$_2$CO$_3$ (2.140 g, 15.49 mmol). The reaction was stirred at 65° C. for 6 hrs. After this time, the reaction was diluted with EtOAc. The resulting solution was washed with water (2×) and saturated aqueous NaCl. The organic layer was separated, dried over Na$_2$SO$_4$, filtered and concentrated. The resulting residue was purified using silica gel chromatography (ISCO system) eluting with a gradient of 0-30% EtOAc/Hex to give the product, ethyl 3-methyl-1-(4-nitrophenyl)piperidine-3-carboxylate (2.922 g, 9.90 mmol, 83% yield) as a yellow oily residue. Anal. Calcd. for C$_{15}$H$_{20}$N$_2$O$_4$ m/z 292.3, found: 293.2 (M+H)$^+$; $^1$H NMR (400 MHz, CDCl$_3$) δ ppm 8.10 (d, J=9.34 Hz, 2H), 6.87 (d, J=9.34 Hz, 2H), 4.18 (d, J=13.19 Hz, 1H), 4.11 (q, J=7.15 Hz, 2H), 3.80-3.58 (m, 1H), 3.00 (s, 1H), 2.90 (d, J=13.19 Hz, 1H), 2.40-2.23 (m, 1H), 1.75 (dd, J=8.52, 4.12 Hz, 2H), 1.42 (s, 1H), 1.26-1.14 (m, 6H).

E: 3-Methyl-1-(4-nitrophenyl)piperidine-3-carboxylic acid

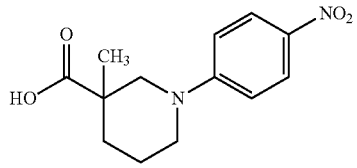 [SMILES: CC1(C(=O)O)CCCN(c2ccc([N+](=O)[O-])cc2)C1]

To a solution of ethyl 3-methyl-1-(4-nitrophenyl)piperidine-3-carboxylate (2.920 g, 9.99 mmol) in THF (12.50 mL) and MeOH (12.5 mL) was added 2 M aqueous solution of LiOH (25 mL, 50 mmol). The resulting yellow solution was stirred at rt for 22 hrs. The reaction was adjusted to pH=5 with 3N aqueous HCl. The solution was extracted with EtOAc (3×). The combined EtOAc extracts were washed with saturated aqueous NaCl (2×), dried over $Na_2SO_4$, filtered and concentrated. The obtained yellow solid was dried under high vacuum to give the desired product, 3-methyl-1-(4-nitrophenyl)piperidine-3-carboxylic acid (2.650 g, 9.53 mmol, 95% yield) as a yellow solid. Anal. Calcd. for $C_{13}H_{16}N_2O_4$ m/z 264.2, found: 265.1 $(M+H)^+$; $^1H$ NMR (400 MHz, $CDCl_3$) δ ppm 8.08 (d, J=9.34 Hz, 2H), 6.89 (d, J=9.34 Hz, 2H), 4.13 (d, J=12.64 Hz, 1H), 3.64 (ddd, J=12.50, 4.53, 4.40 Hz, 1H), 3.10-2.99 (m, 1H), 2.94 (d, J=13.19 Hz, 1H), 2.33-2.18 (m, 1H), 1.88-1.69 (m, 2H), 1.53-1.37 (m, 1H), 1.25 (s, 3H).

F: 3-Methyl-1-(4-nitrophenyl)piperidine-3-carboxamide

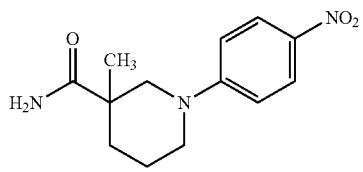 [SMILES: CC1(C(N)=O)CCCN(c2ccc([N+](=O)[O-])cc2)C1]

To a solution of 3-methyl-1-(4-nitrophenyl)piperidine-3-carboxylic acid (2.65 g, 10.03 mmol) in THF (45 ml) cooled at −5° C. (ice/NaCl bath) was added $Et_3N$ (1.537 mL, 11.03 mmol), followed by dropwise addition of isobutyl carbonochloridate (1.443 mL, 11.03 mmol). After addition, the resulting yellow suspension was stirred at −3° C. for 75 min and then 6.25 mL of a 28% aqueous ammonium hydroxide solution (50 mmol, 5.0 equiv.) was added. The reaction mixture was stirred at ~0° C. for 1.5 hrs. The reaction was quenched with water, the resulting mixture (pH>10) was extracted with EtOAc (3×). The combined organic phase was washed with water (2×), saturated aqueous NaCl (2×), dried over $Na_2SO_4$, filtered and concentrated. The crude product was crystallized from EtOAc to give the title compound, 3-methyl-1-(4-nitrophenyl)piperidine-3-carboxamide (777 mg, 2.95 mmol, 29.4% yield), as a brown solid. Anal. Calcd. for $C_{13}H_{17}N_3O_3$ m/z 263.2, found: 264.2 $(M+H)^+$; $^1H$ NMR (400 MHz, $CDCl_3$) δ ppm 8.20-8.02 (m, 2H), 7.06-6.85 (m, 2H), 3.91 (d, J=13.19 Hz, 1H), 3.64-3.49 (m, 1H), 3.16 (ddd, J=12.64, 8.25, 4.40 Hz, 1H), 3.09 (s, 2H), 3.06 (d, J=13.19 Hz, 1H), 2.09 (d, J=13.74 Hz, 1H), 1.91-1.72 (m, 2H), 1.62-1.48 (m, 1H), 1.25 (s, 3H).

G: Benzyl 3-methyl-1-(4-nitrophenyl)piperidin-3-ylcarbamate

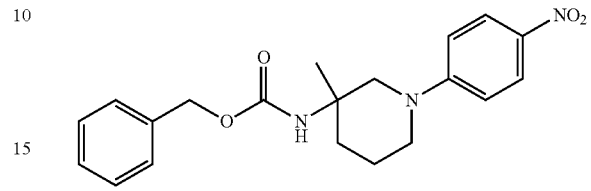

To a solution of 3-methyl-1-(4-nitrophenyl)piperidine-3-carboxamide (1.8538 g, 7.04 mmol) and phenylmethanol (7.61 g, 70.4 mmol) in $ClCH_2CH_2Cl$ (30 ml) cooled at 0° C. was added 1,8-diazabicyclo[5.4.0]undec-7-ene (3.18 mL, 21.12 mmol) dropwise, followed by 1-bromopyrrolidine-2,5-dione (1.378 g, 7.74 mmol) in portions. After addition, the resulting yellow mixture was stirred at 0° C. for 15 min, then at rt for 3.5 hrs, After this time, the reaction was determined not to be complete by LCMS analysis and an additional amount of NBS (138 mg) was added. The reaction was then allowed to stir for an additional 2.5 hrs. The reaction mixture was quenched by addition of water (50 mL) and then adjusted to pH=5 with 1N aqueous HCl. The solution was extracted with EtOAc (3×). The combined EtOAc extracts were washed with water, saturated aqueous NaCl, dried over $Na_2SO_4$, filtered and concentrated. The resulting residue was purified using silica gel chromatography (ISCO system) eluting with a gradient of 0-30% EtOAc/Hex to give the product, benzyl 3-methyl-1-(4-nitrophenyl)piperidin-3-ylcarbamate (2.274 g, 6.16 mmol, 87% yield) as a yellow oil. Anal. Calcd. for $C_{20}H_{23}N_3O_4$ m/z 369.4, found: 370.1 $(M+H)^+$; $^1H$ NMR (400 MHz, $CDCl_3$) δ ppm 8.06 (d, J=9.34 Hz, 2H), 7.37 (d, J=4.40 Hz, 1H), 7.34-7.27 (m, 4H), 6.81 (d, J=9.34 Hz, 2H), 5.09-4.93 (m, 2H), 4.74 (s, 1H), 4.18-4.07 (m, 1H), 3.74-3.62 (m, 1H), 3.11-3.02 (m, 2H), 2.04-1.99 (m, 1H), 1.81-1.68 (m, 2H), 1.58-1.51 (m, 1H), 1.44 (s, 3H).

H: (S)-Benzyl 3-methyl-1-(4-nitrophenyl)piperidin-3-ylcarbamate

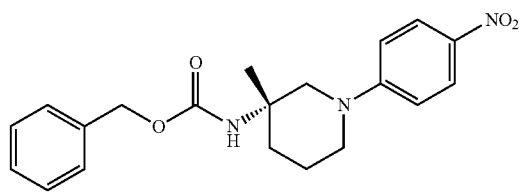 [SMILES: C[C@]1(NC(=O)OCc2ccccc2)CCCN(c2ccc([N+](=O)[O-])cc2)C1]

(S)-Benzyl 3-methyl-1-(4-nitrophenyl)piperidin-3-ylcarbamate (0.527 gm, 1.427 mmol) was separated from its enantiomer using chiral separation method B using benzyl 3-methyl-1-(4-nitrophenyl)piperidin-3-ylcarbamate (1.178 gm, 3.19 mmol). Anal. Calcd. for $C_{20}H_{23}N_3O_4$ m/z 369.4, found: 370.1 $(M+H)^+$; $^1H$ NMR (400 MHz, $CDCl_3$) δ ppm 8.03 (d, J=9.89 Hz, 2H), 7.39-7.16 (m, 5H), 6.80 (d, J=8.79 Hz, 2H), 5.12-4.91 (m, 2H), 4.79 (br. s., 1H), 4.13 (d, J=11.54 Hz, 1H), 3.68 (d, J=13.19 Hz, 1H), 3.14-2.94 (m, 2H), 2.02 (d, J=13.19 Hz, 1H), 1.87-1.63 (m, 2H), 1.63-1.47 (m, 1H), 1.43 (s, 3H).

I: (S)-3-Methyl-1-(4-nitrophenyl)piperidin-3-amine

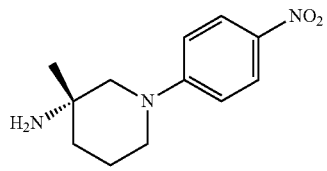 [SMILES: C[C@]1(N)CCCN(c2ccc([N+](=O)[O-])cc2)C1]

To a solution of (S)-benzyl 3-methyl-1-(4-nitrophenyl)piperidin-3-ylcarbamate (525 mg, 1.421 mmol) in $CH_2Cl_2$ (5 ml) cooled at 0° C. was added iodotrimethylsilane (0.290 mL, 2.132 mmol) dropwise. After addition, the orange colored solution was stirred at 0° C. for 15 min, then at rt for 1 hr. The reaction was quenched by addition of 4.3 mmol of HCl (1.1 mL of 4N HCl in dioxane) in MeOH (5 mL). The mixture was then concentrated and the dark reddish residue was partitioned between ether and water. The ether layer was extracted with 0.2 N aqueous HCl. The combined acidic aqueous solution was extracted with ether (1×), then basified at 0° C. with 1N aqueous NaOH to pH=10. The aqueous phase was extracted with $CH_2Cl_2$ (3×). The combined $CH_2Cl_2$ extracts were washed with saturated aqueous NaCl, dried over $Na_2SO_4$, filtered and concentrated to give the desired product, (S)-3-methyl-1-(4-nitrophenyl)piperidin-3-amine (277 mg, 1.177 mmol, 83% yield) as a dark reddish oil. Anal. Calcd. for $C_{12}H_{17}N_3O_2$ m/z 235.2, found: 236.0 (M+H)+; $^1$H NMR (400 MHz, chloroform-d) δ ppm 8.10 (d, J=9.34 Hz, 2H), 6.83 (d, J=9.34 Hz, 2H), 3.62-3.50 (m, 1H), 3.32 (d, J=12.64 Hz, 1H), 3.18 (s, 1H), 3.12 (d, J=13.19 Hz, 1H), 1.82 (d, J=4.95 Hz, 1H), 1.75 (s, 1H), 1.69-1.54 (m, 2H), 1.18 (s, 3H).

J: Benzyl (1R,2R)-2-((S)-3-methyl-1-(4-nitrophenyl)piperidin-3-ylamino)cyclohexylcarbamate

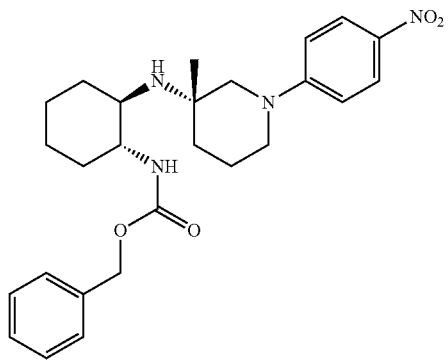 [SMILES: C[C@]1(N[C@@H]2CCCC[C@H]2NC(=O)OCc2ccccc2)CCCN(c2ccc([N+](=O)[O-])cc2)C1]

A solution of benzyl 7-azabicyclo[4.1.0]heptane-7-carboxylate (170 mg, 0.733 mmol) in $CH_2Cl_2$ (1 mL) was added to a 25 mL flask containing (S)-3-methyl-1-(4-nitrophenyl)piperidin-3-amine (115 mg, 0.489 mmol). Then lithium bis(trifluoromethylsulfonyl)amide (28.1 mg, 0.098 mmol) was added in one portion. The resulting greenish orange mixture was stirred at 45° C. under argon for 3 days. The reaction was cooled to rt and diluted with $CH_2Cl_2$. Then saturated aqueous $NaHCO_3$ solution (4 mL) was added to the reaction and the reaction was stirred at rt for 30 min. The separated aqueous layer was extracted with $CH_2Cl_2$ (3×). The combined organic layers were washed with saturated aqueous NaCl, dried over $Na_2SO_4$, filtered and concentrated. The residue was purified using ISCO column eluting with a gradient of 50-100% EtOAc/Hex. Two diastereomers were separated. The slower eluting fraction which had shorter Rf was the desired product. The fractions containing the desired product were concentrated to give the title compound, benzyl (1R,2R)-2-((S)-3-methyl-1-(4-nitrophenyl)piperidin-3-ylamino)cyclohexylcarbamate (37 mg, 0.079 mmol, 16.2% yield) as a yellow oil. Anal. Calcd. for $C_{26}H_{34}N_4O_4$ m/z 466.5, found: 467.3 (M+H)+; $^1$H NMR (400 MHz, $CDCl_3$) δ ppm 8.08-7.96 (m, 2H), 7.39-7.29 (m, 5H), 6.75 (d, J=9.34 Hz, 2H), 5.13-5.01 (m, 2H), 3.38-3.28 (m, 1H), 3.24 (d, J=12.64 Hz, 1H), 3.19-3.07 (m, 2H), 2.98 (d, J=12.64 Hz, 1H), 2.43-2.29 (m, 1H), 2.21-2.09 (m, 1H), 2.02-1.91 (m, 1H), 1.88-1.77 (m, 1H), 1.67-1.57 (m, 4H), 1.55-1.44 (m, 3H), 1.35-1.15 (m, 4H), 1.07 (s, 3H).

The following compounds were made through an array synthesis using general procedures G, H or I:

| Example | Structure |
|---|---|
| Example 59 | ![structure] |
| Example 60 | ![structure] |
| Example 61 | ![structure] |

-continued
| Example | Structure |
|---|---|
| Example 62 | 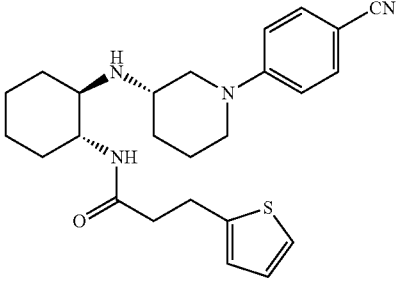 [SMILES: N#Cc1ccc(N2CCC[C@H](N[C@@H]3CCCC[C@H]3NC(=O)CCc3cccs3)C2)cc1] |
| Example 63 | 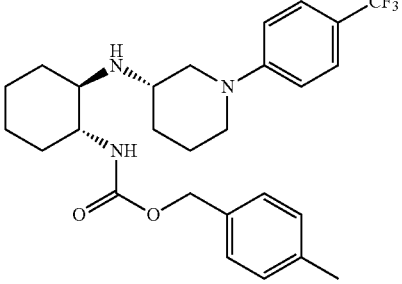 |
| Example 64 | 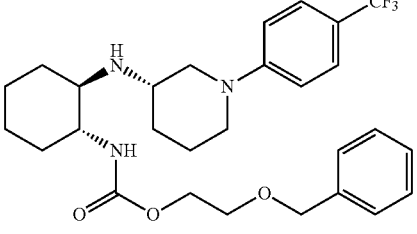 |
| Example 65 | 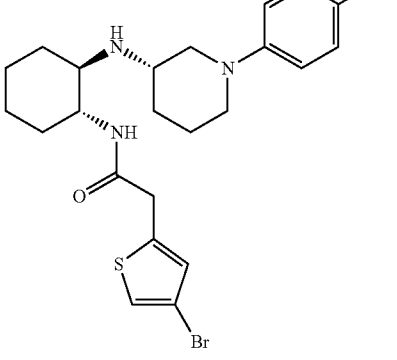 |
| Example 66 | 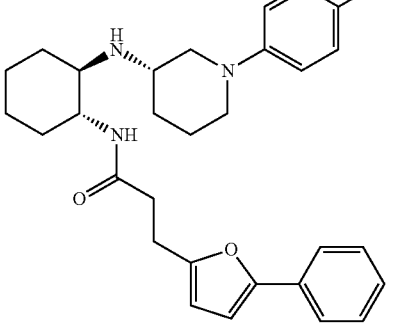 |
-continued
| Example | Structure |
|---|---|
| Example 67 | 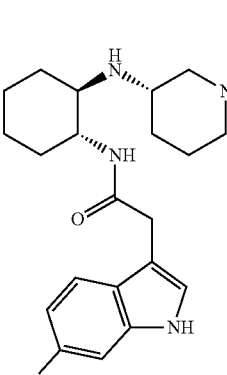 |
| Example 68 | 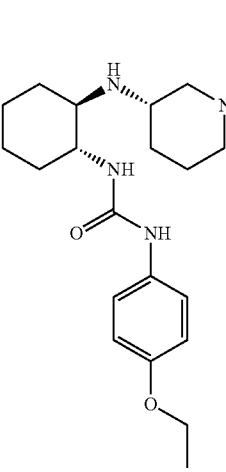 |
| Example 69 | 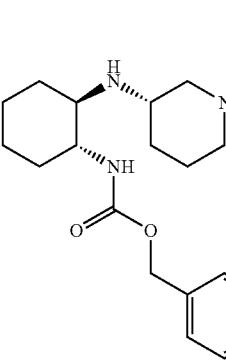 |

| Example | Structure |
|---|---|
| Example 70 | 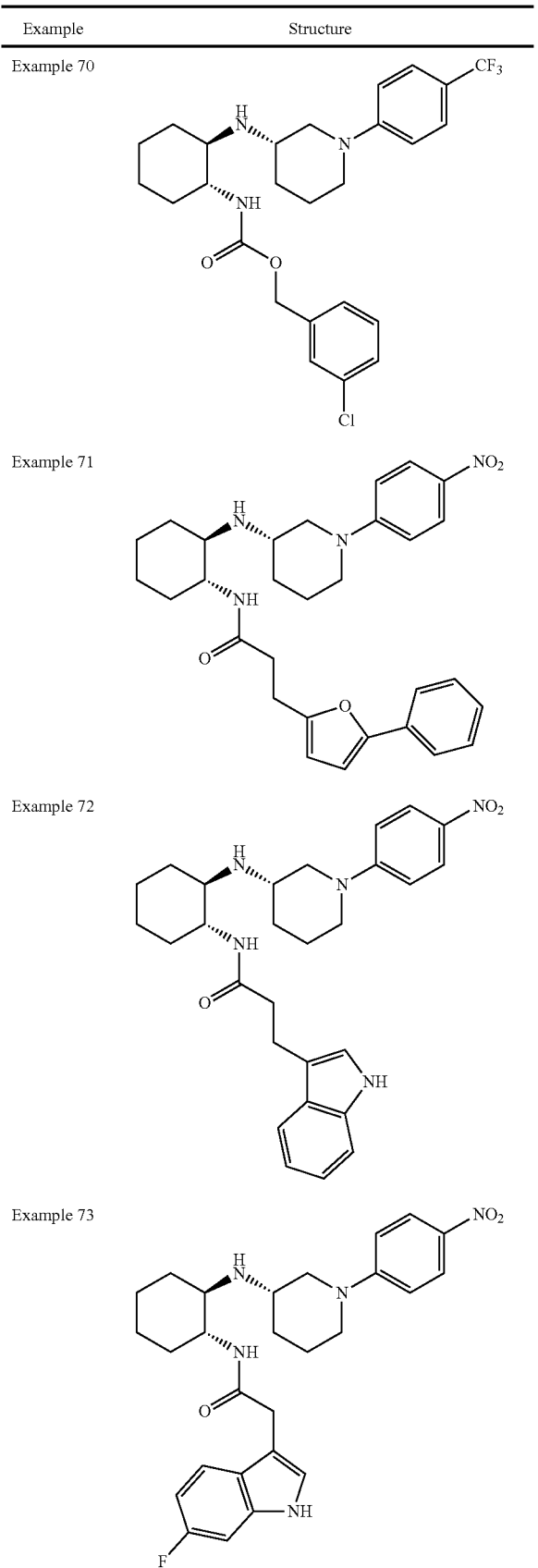 |
| Example 71 | |
| Example 72 | |
| Example 73 | |
| Example | Structure |
|---|---|
| Example 74 | 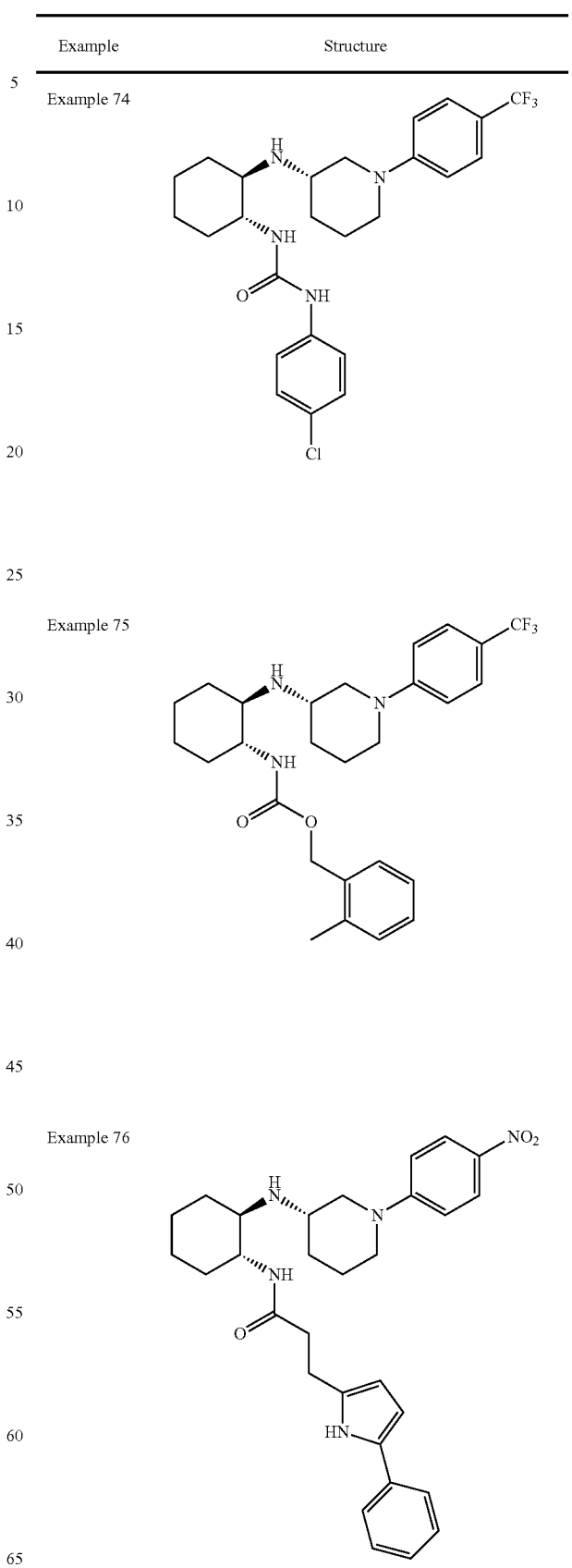 |
| Example 75 | |
| Example 76 | |

| Example | Structure |
|---|---|
| Example 77 | (structure) |
| Example 78 | (structure) |
| Example 79 | (structure) |
| Example 80 | (structure) |
| Example 81 | (structure) |
| Example 82 | (structure) |
| Example 83 | (structure) |
| Example 84 | (structure) |

| Example | Structure |
|---|---|
| Example 85 | 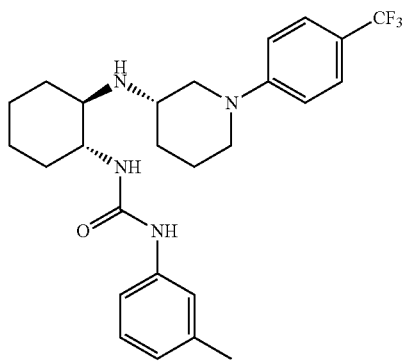 [SMILES: Cc1cccc(NC(=O)N[C@@H]2CCCC[C@H]2N[C@H]2CCCN(c3ccc(C(F)(F)F)cc3)C2)c1] |
| Example 86 | 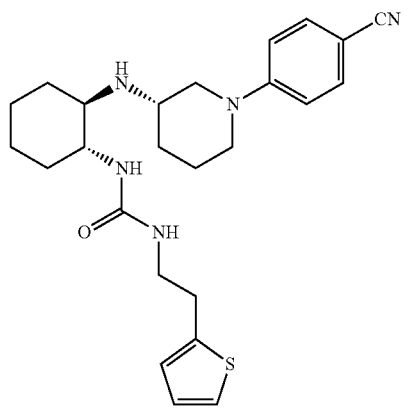 [SMILES: N#Cc1ccc(N2CCC[C@H](N[C@@H]3CCCC[C@H]3NC(=O)NCCc3cccs3)C2)cc1] |
| Example 87 | 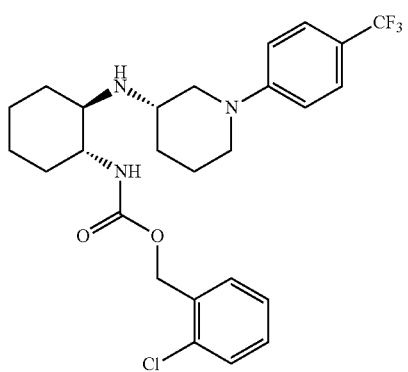 [SMILES: O=C(N[C@@H]1CCCC[C@H]1N[C@H]1CCCN(c2ccc(C(F)(F)F)cc2)C1)OCc1ccccc1Cl] |
| Example 88 | 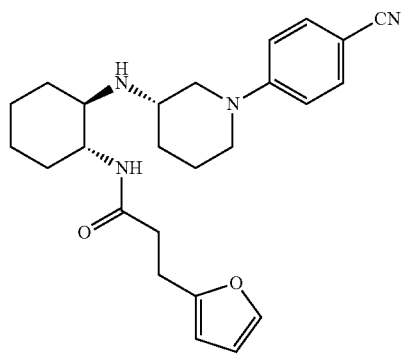 [SMILES: N#Cc1ccc(N2CCC[C@H](N[C@@H]3CCCC[C@H]3NC(=O)CCc3ccco3)C2)cc1] |
| Example | Structure |
|---|---|
| Example 89 | 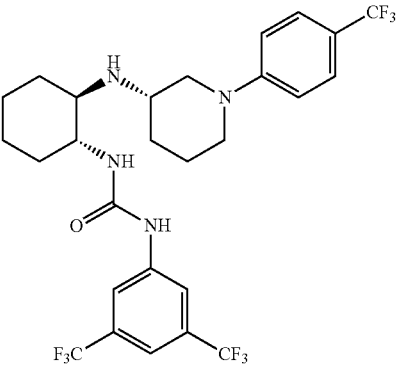 [SMILES: O=C(Nc1cc(C(F)(F)F)cc(C(F)(F)F)c1)N[C@@H]1CCCC[C@H]1N[C@H]1CCCN(c2ccc(C(F)(F)F)cc2)C1] |
| Example 90 | 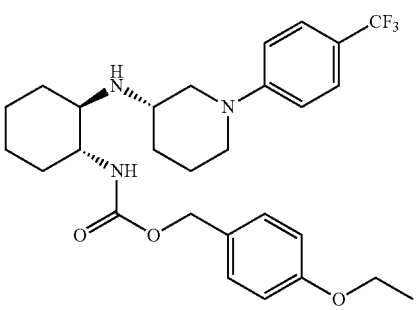 [SMILES: CCOc1ccc(COC(=O)N[C@@H]2CCCC[C@H]2N[C@H]2CCCN(c3ccc(C(F)(F)F)cc3)C2)cc1] |
The following compounds are made through library synthesis using the General Procedures H and I. The two diastereomers are not separated.
| Example | Structure |
|---|---|
| Example 91 | 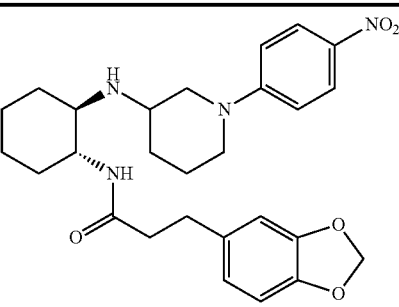 |
| Example 92 | 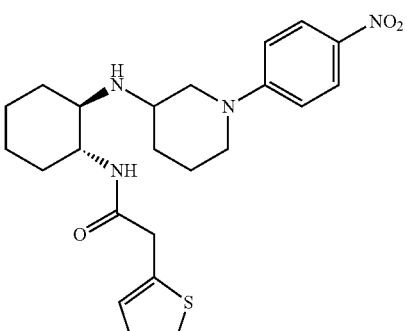 |

-continued

| Example | Structure |
|---|---|
| Example 93 | *(cyclohexane-1,2-diamine with N-(4-nitrophenyl)piperidin-3-yl amine and 2-(4-methoxyphenyl)acetamide)* |
| Example 94 | *(cyclohexane-1,2-diamine with N-(4-nitrophenyl)piperidin-3-yl amine and 2-(4-bromophenyl)acetamide)* |
| Example 95 | *(cyclohexane-1,2-diamine with N-(4-nitrophenyl)piperidin-3-yl amine and 2-(4-trifluoromethylphenyl)acetamide)* |
| Example 96 | *(cyclohexane-1,2-diamine with N-(4-nitrophenyl)piperidin-3-yl amine and 3-(furan-2-yl)propanamide)* |

-continued

| Example | Structure |
|---|---|
| Example 97 | *(cyclohexane-1,2-diamine with N-(4-nitrophenyl)piperidin-3-yl amine and 2-(4-chlorophenyl)acetamide)* |
| Example 98 | *(cyclohexane-1,2-diamine with N-(4-nitrophenyl)piperidin-3-yl amine and 2-(4-phenoxyphenyl)acetamide)* |
| Example 99 | *(cyclohexane-1,2-diamine with N-(4-nitrophenyl)piperidin-3-yl amine and 3-(4-trifluoromethylphenyl)propanamide)* |

-continued
| Example | Structure |
|---|---|
| Example 100 | 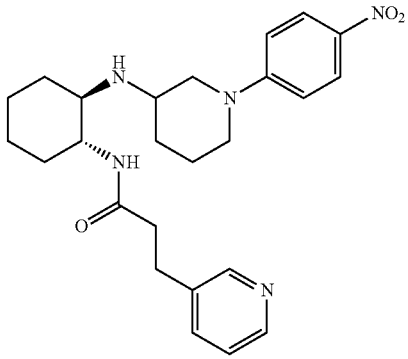 [SMILES: O=C(CCc1cccnc1)N[C@@H]1CCCC[C@H]1NC1CCCN(c2ccc([N+](=O)[O-])cc2)C1] |
| Example 101 | 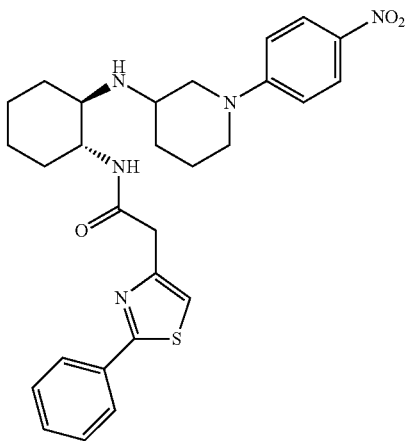 [SMILES: O=C(Cc1csc(-c2ccccc2)n1)N[C@@H]1CCCC[C@H]1NC1CCCN(c2ccc([N+](=O)[O-])cc2)C1] |
| Example 102 | 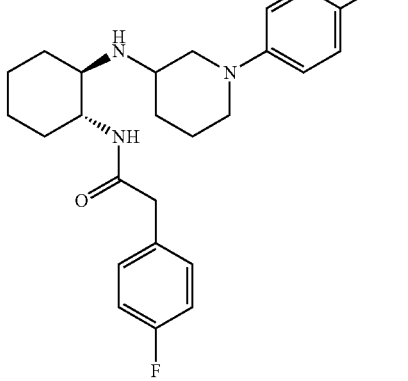 |
-continued
| Example | Structure |
|---|---|
| Example 103 | 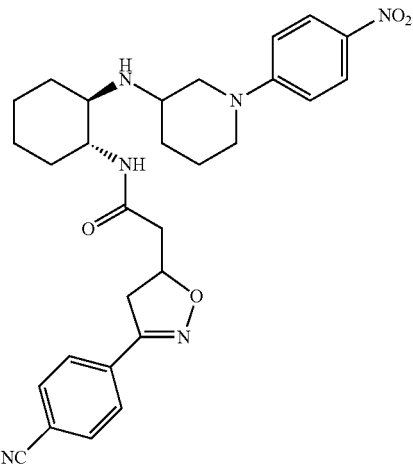 [SMILES: N#Cc1ccc(C2=NOC(CC(=O)N[C@@H]3CCCC[C@H]3NC3CCCN(c4ccc([N+](=O)[O-])cc4)C3)C2)cc1] |
| Example 104 | 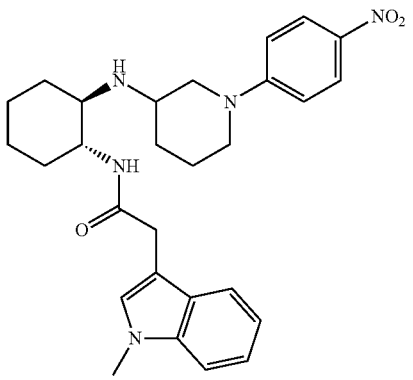 [SMILES: Cn1cc(CC(=O)N[C@@H]2CCCC[C@H]2NC2CCCN(c3ccc([N+](=O)[O-])cc3)C2)c2ccccc21] |
| Example 105 | 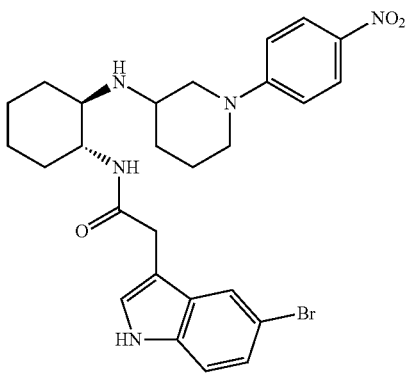 [SMILES: O=C(Cc1c[nH]c2ccc(Br)cc12)N[C@@H]1CCCC[C@H]1NC1CCCN(c2ccc([N+](=O)[O-])cc2)C1] |
| Example 106 | 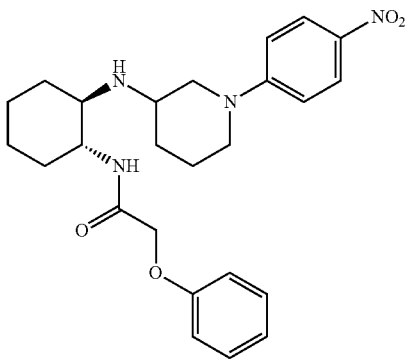 [SMILES: O=C(COc1ccccc1)N[C@@H]1CCCC[C@H]1NC1CCCN(c2ccc([N+](=O)[O-])cc2)C1] |

-continued

| Example | Structure |
|---|---|
| Example 107 | 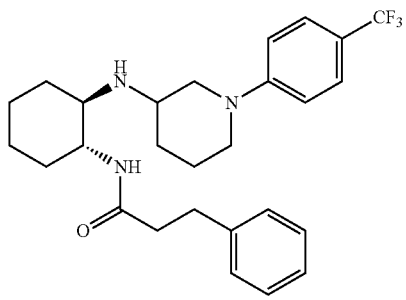 |
| Example 108 | 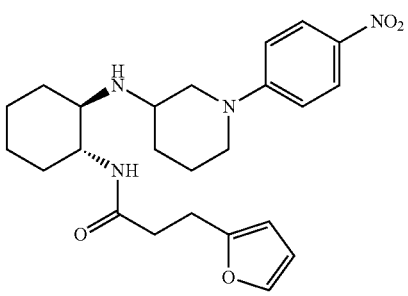 [SMILES: O=C(CCc1ccco1)N[C@@H]1CCCC[C@H]1NC1CCCN(c2ccc([N+](=O)[O-])cc2)C1] |
| Example 109 | 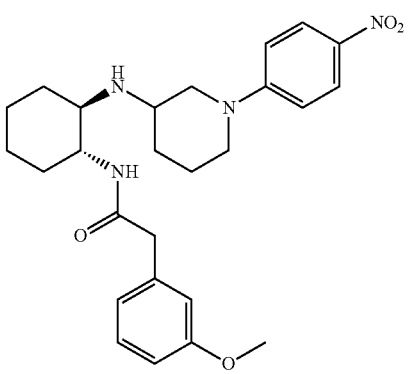 [SMILES: COc1cccc(CC(=O)N[C@@H]2CCCC[C@H]2NC2CCCN(c3ccc([N+](=O)[O-])cc3)C2)c1] |
| Example 110 | 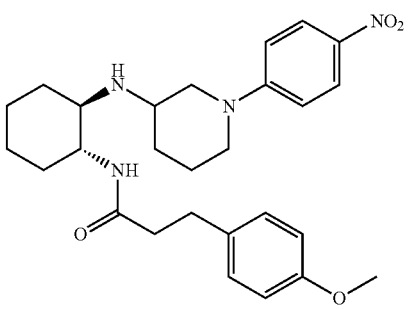 [SMILES: COc1ccc(CCC(=O)N[C@@H]2CCCC[C@H]2NC2CCCN(c3ccc([N+](=O)[O-])cc3)C2)cc1] |

-continued

| Example | Structure |
|---|---|
| Example 111 | 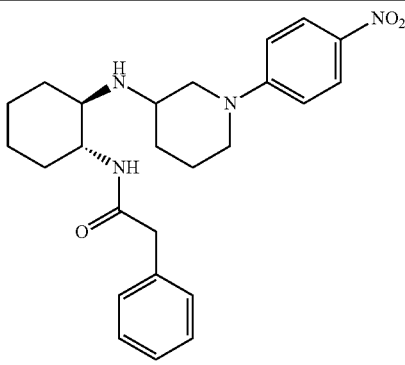 |
| Example 112 | 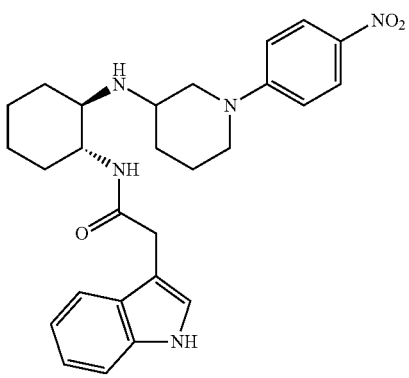 [SMILES: O=C(Cc1c[nH]c2ccccc12)N[C@@H]1CCCC[C@H]1NC1CCCN(c2ccc([N+](=O)[O-])cc2)C1] |

What is claimed:
1. A compound of formula Ia

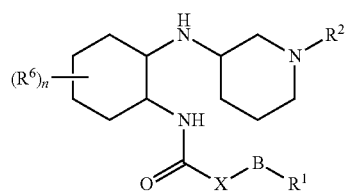

wherein
X is $CH_2$, O, or NH;
B is absent or is —$(CH_2)_m$—;
R is H or ($C_1$-$C_6$)alkyl;
$R^1$ is ($C_6$)aryl or 5- to 8-membered cycloalkyl or 5- to 8-membered heteroaryl, said heteroaryl containing 1-4 heteroatoms selected from N, O, and S, wherein the cycloalkyl, aryl and heteroaryl may be optionally substituted with one or more $R^3$;
$R^2$ is ($C_6$)aryl or 5- to 8-membered heteroaryl, said heteroaryl containing 1-4 heteroatoms selected from N, O, and S, wherein both the aryl and heteroaryl may be optionally substituted with one or more $R^4$, wherein $R^2$ is connected to ring A through the nitrogen atom;
$R^3$ is independently one or more halogen, —OH, —CN, —$NO_2$, —COOH, —$CO_2$($C_1$-$C_6$)alkyl, —$CF_3$, —$OCHF_2$, —$OCF_3$, —($C_1$-$C_6$)-alkyl, —($C_1$-$C_6$)-alkyloxy, —CON $R^9R^{10}$, —O(C=O)$NR^9R^{10}$, —$NR^9R^{10}$, —($C_1$-$C_6$)-alkylCOOH, —($C_1$-$C_6$)-alkyl-$CO_2$($C_1$-$C_6$)-alkyl, —($C_1$-$C_6$)-alkylOH, —($C_1$-$C_6$)-alkylCON $R^9R^{10}$, —$(C_{6-10})$aryl, a 5- to 8-membered heteroaryl, which contains 1-4 heteroatoms selected from N, O, and S; and a 5- to 10-membered heterocyclyl, which contains 1-4 heteroatoms selected from N, O, and S; wherein any alkyl, aryl, heteroaryl, and heterocyclyl may be optionally substituted with one or more substituents selected from the group consisting of: halo, —OH, cyano, nitro, —$CF_3$, —$OCF_3$, —$OCF_2$, $(C_1$-$C_6)$-alkyl, $(C_2$-$C_6)$-alkynyl, $(C_1$-$C_6)$-alkyloxy, —COOH, —$CO_2$$(C_1$-$C_6)$-alkyl, —$CONR^9R^{10}$, —$NR^9R^{10}$, —O(C═O)—$(C_1$-$C_6)$-alkyl, —O(C═O)$NR^9R^{10}$; —$(C_1$-$C_6)$-alkylCOOH, —$(C_1$-$C_6)$-alkylOH, —$(C_1$-$C_6)$-alkyl$CONR^9R^{10}$, —$(C_1$-$C_6)$-alkyl-$CO_2(C_1$-$C_6)$-alkyl, $(C_{6-10})$aryl, a 5- to 8-membered heteroaryl, which contains 1-4 heteroatoms selected from N, O, and S, a 5- to 10-membered heterocyclyl, which contains 1-4 heteroatoms selected from N, O, and S;

or $R^3$ and another $R^3$ can optionally be taken together with the carbon atom that they are attached to form a —$(C_4$-$C_8)$cycloalkyl, —$(C_6)$aryl, a 5- to 8-membered heterocyclyl, which contains 1-4 heteroatoms selected from N, O, and S, or a 5- to 8-membered heteroaryl ring, which contains 1-4 heteroatoms selected from N, O, and S, that may be optionally substituted with one or more substituents selected from the group consisting of: halo, —OH, cyano, nitro, —$CF_3$, —$OCF_3$, —$OCF_2$, $(C_1$-$C_6)$-alkyl, $(C_2$-$C_6)$-alkenyl, $(C_2$-$C_6)$-alkynyl, $(C_1$-$C_6)$-alkyloxy, —COOH, —$CO_2(C_1$-$C_6)$-alkyl, —$CONR^9R^{10}$, —$NR^9R^{10}$, —O(C═O)—$(C_1$-$C_6)$-alkyl, —O(C═O)$NR^9R^{10}$; —$(C_1$-$C_6)$-alkylCOOH, —$(C_1$-$C_6)$-alkylOH, —$(C_1$-$C_6)$-alkyl$CONR^9R^{10}$, —$(C_1$-$C_6)$-alkyl-$CO_2(C_1$-$C_6)$-alkyl, $(C_{6-10})$aryl, a 5- to 8-membered heteroaryl, which contains 1-4 heteroatoms selected from N, O, and S, a 5- to 10-membered heterocyclo, which contains 1-4 heteroatoms selected from N, O, and S; halo$(C_1$-$C_6)$alkyl, and halo$(C_1$-$C_6)$alkyloxy;

$R^4$ is halogen, —OH, $CF_3$, —$OCF_2$, —$OCF_3$, —CN, —$NO_2$, —COOH, $(C_1$-$C_6)$-alkyl, $(C_1$-$C_6)$-alkyloxy, —$CO(C_1$-$C_6)$-alkyl, —$CO_2(C_1$-$C_6)$-alkyl, —$CONR^9R^{10}$, —$NR^9R^{10}$, or a 5- to 10-membered heteroaryl containing 1-4 heteroatoms selected from N, O, and S, optionally substituted with one or more $R^5$;

$R^5$ is halogen, —OH, —$CF_3$, —$OCF_2$, —$OCF_3$, —CN, —$NO_2$, —$(C_1$-$C_6)$alkyl, or —$(C_1$-$C_6)$alkyloxy;

$R^6$ is halogen, —OH, $(C_1$-$C_6)$-alkyl or $(C_3$-$C_6)$-cycloalkyl;

$R^9$ and $R^{10}$, at each occurrence, are independently hydrogen or $(C_1$-$C_8)$-alkyl, wherein the alkyl may be optionally substituted with one or more $R^{11}$'s;

or $R^9$ and $R^{10}$ are taken together with the nitrogen to which both are attached to form a 3- to 8-membered ring, which may optionally contain 1-4 heteroatoms selected from N, O, and S and be optionally substituted with one or more $R^{11}$'s;

$R^{11}$ is halo, —OH, cyano, $(C_1$-$C_6)$-alkyl;

m is 1, 2, to 3;

n is 1, 2 or 3;

or a stereoisomer, tautomer, or pharmaceutically acceptable salt thereof.

2. The compound according to claim 1, wherein $R^2$ is $(C_6)$aryl or 5- to 6-membered heteroaryl, said heteroaryl containing 1-4 heteroatoms selected from N, and O, wherein both the aryl and heteroaryl may be optionally substituted with one or more $R^4$;

$R^4$ is fluoro, chloro, $CF_3$, —$OCF_2$, —$OCF_3$, —CN, —$NO_2$, or a 5- to 6-membered heteroaryl containing 1-4 heteroatoms selected from N, O, and S, optionally substituted with one or more $R^5$; and $R^5$ is halogen, —OH, —$CF_3$, —$OCF_2$, —$OCF_3$, —CN, —$(C_1$-$C_6)$alkyl, or —$(C_1$-$C_6)$alkyloxy;

or a stereoisomer, tautomer, or pharmaceutically acceptable salt thereof.

3. The compound according to claim 2, wherein $R^1$ is $(C_6)$aryl or 5- to 6-membered heteroaryl, said heteroaryl containing 1-4 heteroatoms selected from N, O, and S, wherein aryl and heteroaryl may be optionally substituted with one or more $R^3$;

$R^2$ is phenyl, pyridyl, pyrimidinyl, pyridazinyl, or pyrazinyl, substituted with one or more $R^4$;

$R^3$ is independently chosen from halogen, —OH, —CN, —$CF_3$, —$OCHF_2$, —$OCF_3$, —$(C_1$-$C_6)$alkyl, —$(C_1$-$C_6)$-alkyloxy, —$CONR^9R^{10}$, —O(C═O)$NR^9R^{10}$, —$(C_1$-$C_6)$-alkyl$CONR^9R^{10}$, —$(C_6$-$C_{10})$aryl, a 5- to 6-membered heteroaryl, which contains 1-4 heteroatoms selected from N, O, and S; and a 5- to 7-membered heterocyclyl, which contains 1-4 heteroatoms selected from N, O, and S; wherein any alkyl, aryl, heteroaryl, and heterocyclyl may be optionally substituted with one or more substituents selected from the group consisting of halo, —OH, cyano, —$CF_3$, —$OCF_3$, —$OCF_2$, $(C_1$-$C_6)$-alkyl, $(C_1$-$C_6)$-alkyloxy, —$CONR^9R^{10}$ and —O(C═O)$NR^9R^{10}$;

$R^4$ is fluoro, chloro, $CF_3$, —$OCF_2$, —$OCF_3$, —CN or —$NO_2$; or $R^4$ is tetrazole, oxadiazole, oxazole, pyrazole or isoxazole, optionally substituted with one or more $R^5$;

$R^5$ is halogen, —OH, —$CF_3$, —$OCF_2$, —$OCF_3$, —CN, methyl, ethyl, cyclopropyl, methoxy, ethoxy or cyclopropyloxy;

or a stereoisomer, tautomer, or pharmaceutically acceptable salt thereof.

4. A compound of formula Ib

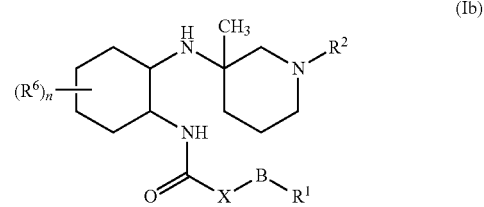

(Ib)

wherein

X is $CH_2$, O, or NH;

B is absent or is $(CH_2)_m$—;

R is H or $(C_1$-$C_6)$alkyl;

$R^1$ is $(C_6)$aryl or 5- to 8-membered cycloalkyl or 5- to 8-membered heteroaryl, said heteroaryl containing 1-4 heteroatoms selected from N, O, and S, wherein the cycloalkyl, aryl and heteroaryl may be optionally substituted with one or more $R^3$;

$R^2$ is $(C_6)$aryl or 5- to 8-membered heteroaryl, said heteroaryl containing 1-4 heteroatoms selected from N, O, and S, wherein both the aryl and heteroaryl may be optionally substituted with one or more $R^4$, wherein $R^2$ is connected to ring A through the nitrogen atom;

$R^3$ is independently one or more halogen, —OH, —CN, —$NO_2$, —COOH, —$CO_2(C_1$-$C_6)$alkyl, —$CF_3$, —$OCHF_2$, —$OCF_3$, —$(C_1$-$C_6)$-alkyl, —$(C_1$-$C_6)$-alkyloxy, —$CONR^9R^{10}$, —O(C═O)$NR^9R^{10}$, —$NR^9R^{10}$, —$(C_1$-$C_6)$-alkylCOOH, —$(C_1$-$C_6)$-alkyl-$CO_2(C_1$-$C_6)$-alkyl, —$(C_1$-$C_6)$-alkylOH, —$(C_1$-$C_6)$-alkyl$CONR^9R^{10}$, —$(C_{6-10})$aryl, a 5- to 8-membered heteroaryl, which contains 1-4 heteroatoms selected from N, O, and S; and a 5- to 10-membered heterocyclyl, which contains 1-4 heteroatoms selected from N, O, and S; wherein any alkyl, aryl, heteroaryl, and heterocyclyl may be optionally substituted with one or more substituents selected from the group consisting of: halo, —OH, cyano, nitro, —CF$_3$, —OCF$_3$, —OCF$_2$, ($C_1$-$C_6$)-alkyl, ($C_2$-$C_6$)-alkynyl, ($C_1$-$C_6$)-alkyloxy, —COOH, —CO$_2$($C_1$-$C_6$)-alkyl, —CONR$^9$R$^{10}$, —NR$^9$R$^{10}$, —O(C=O)—($C_1$-$C_6$)-alkyl, —O(C=O)NR$^9$R$^{10}$; —($C_1$-$C_6$)-alkylCOOH, —($C_1$-$C_6$)-alkylOH, —($C_1$-$C_6$)-alkylCONR$^9$R$^{10}$, —($C_1$-$C_6$)-alkyl-CO$_2$($C_1$-$C_6$)-alkyl, ($C_6$-$C_{10}$)aryl, a 5- to 8-membered heteroaryl, which contains 1-4 heteroatoms selected from N, O, and S, a 5- to 10-membered heterocyclyl, which contains 1-4 heteroatoms selected from N, O, and S;

or R$^3$ and another R$^3$ can optionally be taken together with the carbon atom that they are attached to form a —($C_4$-$C_8$)cycloalkyl, —($C_6$)aryl, a 5- to 8-membered heterocyclyl, which contains 1-4 heteroatoms selected from N, O, and S, or a 5- to 8-membered heteroaryl ring, which contains 1-4 heteroatoms selected from N, O, and S, that may be optionally substituted with one or more substituents selected from the group consisting of: halo, —OH, cyano, nitro, —CF$_3$, —OCF$_3$, —OCF$_2$, ($C_1$-$C_6$)-alkyl, ($C_2$-$C_6$)-alkenyl, ($C_2$-$C_6$)-alkynyl, ($C_1$-$C_6$)-alkyloxy, —COOH, —CO$_2$($C_1$-$C_6$)-alkyl, —CONR$^9$R$^{10}$, —NR$^9$R$^{10}$, —O(C=O)—($C_1$-$C_6$)-alkyl, —O(C=O)NR$^9$R$^{10}$; —($C_1$-$C_6$)-alkylCOOH, —($C_1$-$C_6$)-alkylOH, —($C_1$-$C_6$)-alkylCONR$^9$R$^{10}$, —($C_1$-$C_6$)-alkyl-CO$_2$($C_1$-$C_6$)-alkyl, ($C_{6-10}$)aryl, a 5- to 8-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;

R$^4$ is halogen, —OH, CF$_3$, —OCF$_2$, —CN, —NO$_2$, —COOH, ($C_1$-$C_6$)-alkyl, alkyloxy, —CO($C_1$-$C_6$)-alkyl, —CO$_2$($C_1$-$C_6$)-alkyl, —CONR$^9$R$^{10}$, —NR$^9$R$^{10}$, or a 5- to 10-membered heteroaryl containing 1-4 heteroatoms selected from N, O, and S, optionally substituted with one or more R$^5$;

R$^5$ is halogen, —OH, —CF$_3$, —OCF$_2$, —OCF$_3$, —CN, —NO$_2$, —($C_1$-$C_6$)alkyl, or —($C_1$-$C_6$)alkyloxy;

R$^6$ is halogen, —OH, ($C_1$-$C_6$)-alkyl or ($C_3$-$C_6$)-cycloalkyl;

R$^9$ and R$^{10}$, at each occurrence, are independently hydrogen or ($C_1$-$C_8$)-alkyl, wherein the alkyl may be optionally substituted with one or more R$^{11}$'s;

or R$^9$ and R$^{10}$ are taken together with the nitrogen to which both are attached to form a 3- to 8-membered ring, which may optionally contain 1-4 heteroatoms selected from N, O, and S and be optionally substituted with one or more R$^{11}$'s;

R$^{11}$ is halo, —OH, cyano, ($C_1$-$C_6$)-alkyl;

m is 1, 2, to 3;

n is 1, 2 or 3;

or a stereoisomer, tautomer, or pharmaceutically acceptable salt thereof.

5. The compound according to claim 4, wherein

R$^2$ is ($C_6$)aryl or 5- to 6-membered heteroaryl, said heteroaryl containing 1-4 heteroatoms selected from N, and O, wherein both the aryl and heteroaryl may be optionally substituted with one or more R$^4$;

R$^4$ is fluoro, chloro, CF$_3$, —OCF$_2$, —OCF$_3$, —CN, —NO$_2$, or a 5- to 6-membered heteroaryl containing 1-4 heteroatoms selected from N, O, and S, optionally substituted with one or more R$^5$;

R$^5$ is halogen, —OH, —CF$_3$, —OCF$_2$, —OCF$_3$, —CN, —($C_1$-$C_6$)alkyl, or —($C_1$-$C_6$)alkyloxy;

or a stereoisomer, tautomer, or pharmaceutically acceptable salt thereof.

6. The compound according to claim 5, wherein

R$^1$ is ($C_6$)aryl or 5- to 6-membered heteroaryl, said heteroaryl containing 1-4 heteroatoms selected from N, O, and S, wherein aryl and heteroaryl may be optionally substituted with one or more R$^3$;

R$^2$ is phenyl, pyridyl, pyrimidinyl, pyridazinyl, or pyrazinyl, substituted with one or more R$^4$;

R$^3$ is independently chosen from halogen, —OH, —CN, —CF$_3$, —OCHF$_2$, —OCF$_3$, —($C_1$-$C_6$)alkyl, —($C_1$-$C_6$)-alkyloxy, —CONR$^9$R$^{10}$, —O(C=O)NR$^9$R$^{10}$, —($C_1$-$C_6$)-alkylCONR$^9$R$^{10}$, —($C_6$-$C_{10}$)aryl, a 5- to 6-membered heteroaryl, which contains 1-4 heteroatoms selected from N, O, and S; and a 5- to 7-membered heterocyclyl, which contains 1-4 heteroatoms selected from N, O, and S; wherein any alkyl, aryl, heteroaryl, and heterocyclyl may be optionally substituted with one or more substituents selected from the group consisting of halo, —OH, cyano, —CF$_3$, —OCF$_3$, —OCF$_2$, ($C_1$-$C_6$)-alkyl, ($C_1$-$C_6$)-alkyloxy, —CONR$^9$R$^{10}$ and —O(C=O)NR$^9$R$^{10}$;

R$^4$ is fluoro, chloro, CF$_3$, —OCF$_2$, —CN or —NO$_2$; or

R$^4$ is tetrazole, oxadiazole, oxazole, pyrazole or isoxazole, optionally substituted with one or more R$^5$;

R$^5$ is halogen, —OH, —CF$_3$, —OCF$_2$, —OCF$_3$, —CN, methyl, ethyl, cyclopropyl, methoxy, ethoxy or cyclopropyloxy;

or a stereoisomer, tautomer, or pharmaceutically acceptable salt thereof.

7. A compound of formula Ic

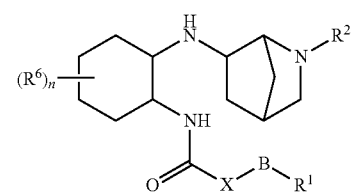

(Ic)

wherein

X is CH$_2$, O, or NH;

B is absent or is —(CH$_2$)$_m$—;

R is H or ($C_1$-$C_6$)alkyl;

R$^1$ is ($C_6$)aryl or 5- to 8-membered cycloalkyl or 5- to 8-membered heteroaryl, said heteroaryl containing 1-4 heteroatoms selected from N, O, and S, wherein the cycloalkyl, aryl and heteroaryl may be optionally substituted with one or more R$^3$;

R$^2$ is ($C_6$)aryl or 5- to 8-membered heteroaryl, said heteroaryl containing 1-4 heteroatoms selected from N, O, and S, wherein both the aryl and heteroaryl may be optionally substituted with one or more R$^4$, wherein R$^2$ is connected to ring A through the nitrogen atom;

R$^3$ is independently one or more halogen, —OH, —CN, —NO$_2$, —COOH, —CO$_2$($C_1$-$C_6$)alkyl, —CF$_3$, —OCHF$_2$, —OCF$_3$, —($C_1$-$C_6$)-alkyl, —($C_1$-$C_6$)-alkyloxy, —CON R$^9$R$^{10}$, —O(C=O)NR$^9$R$^{10}$, —NR$^9$R$^{10}$, —($C_1$-$C_6$)-alkylCOOH, —($C_1$-$C_6$)-alkyl-CO$_2$($C_1$-$C_6$)-alkyl, —($C_1$-$C_6$)-alkylOH, —($C_1$-$C_6$)-alkylCON R$^9$R$^{10}$, —($C_{6-10}$)aryl, a 5- to 8-membered heteroaryl, which contains 1-4 heteroatoms selected from N, O, and S; and a 5- to 10-membered heterocyclyl, which contains 1-4 heteroatoms selected from N, O, and S; wherein any alkyl, aryl, heteroaryl, and heterocyclyl may be optionally substituted with one or more substituents selected from the group consisting of: halo, —OH, cyano, nitro, —$CF_3$, —$OCF_3$, —$OCF_2$, ($C_1$-$C_6$)-alkyl, ($C_2$-$C_6$)-alkynyl, ($C_1$-$C_6$)-alkyloxy, —COOH, —$CO_2$($C_1$-$C_6$)-alkyl, —$CONR^9R^{10}$, —$NR^9R^{10}$, —O(C=O)—($C_1$-$C_6$)-alkyl, —O(C=O)$NR^9R^{10}$; —($C_1$-$C_6$)-alkylCOOH, —($C_1$-$C_6$)-alkylOH, —($C_1$-$C_6$)-alkyl$CONR^9R^{10}$, —($C_1$-$C_6$)-alkyl-$CO_2$($C_1$-$C_6$)-alkyl, ($C_{6-10}$)aryl, a 5- to 8-membered heteroaryl, which contains 1-4 heteroatoms selected from N, O, and S, a 5- to 10-membered heterocyclyl, which contains 1-4 heteroatoms selected from N, O, and S;

or $R^3$ and another $R^3$ can optionally be taken together with the carbon atom that they are attached to form a —($C_4$-$C_8$)cycloalkyl, —($C_6$)aryl, a 5- to 8-membered heterocyclyl, which contains 1-4 heteroatoms selected from N, O, and S, or a 5- to 8-membered heteroaryl ring, which contains 1-4 heteroatoms selected from N, O, and S, that may be optionally substituted with one or more substituents selected from the group consisting of: halo, —OH, cyano, nitro, —$CF_3$, —$OCF_3$, —$OCF_2$, ($C_1$-$C_6$)-alkyl, ($C_2$-$C_6$)-alkenyl, ($C_2$-$C_6$)-alkynyl, ($C_1$-$C_6$)-alkyloxy, —COOH, —$CO_2$($C_1$-$C_6$)-alkyl, —$CONR^9R^{10}$, —$NR^9R^{10}$, —O(C=O)—($C_1$-$C_6$)-alkyl, —O(C=O)$NR^9R^{10}$; —($C_1$-$C_6$)-alkylCOOH, —($C_1$-$C_6$)-alkylOH, —($C_1$-$C_6$)-alkyl$CONR^9R^{10}$, —($C_1$-$C_6$)-alkyl-$CO_2$($C_1$-$C_6$)-alkyl, ($C_{6-10}$)aryl, a 5- to 8-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;

$R^4$ is halogen, —OH, $CF_3$, —$OCF_2$, —$OCF_3$, —CN, —$NO_2$, —COOH, ($C_1$-$C_6$)-alkyl, ($C_1$-$C_6$)-alkyloxy, —CO($C_1$-$C_6$)-alkyl, —$CO_2$($C_1$-$C_6$)-alkyl, —$CONR^9R^{10}$, —$NR^9R^{10}$, or a 5- to 10-membered heteroaryl containing 1-4 heteroatoms selected from N, O, and S, optionally substituted with one or more $R^5$;

$R^5$ is halogen, —OH, —$CF_3$, —$OCF_2$, —$OCF_3$, —CN, —$NO_2$, —($C_1$-$C_6$)alkyl, or —($C_1$-$C_6$)alkyloxy;

$R^6$ is halogen, —OH, ($C_1$-$C_6$)-alkyl or ($C_3$-$C_6$)-cycloalkyl;

$R^9$ and $R^{10}$, at each occurrence, are independently hydrogen or ($C_1$-$C_8$)-alkyl, wherein the alkyl may be optionally substituted with one or more $R^{11}$'s;

or $R^9$ and $R^{10}$ are taken together with the nitrogen to which both are attached to form a 3- to 8-membered ring, which may optionally contain 1-4 heteroatoms selected from N, O, and S and be optionally substituted with one or more $R^{11}$'s;

$R^{11}$ is halo, —OH, cyano, ($C_1$-$C_6$)-alkyl;

m is 1, 2, to 3;

n is 1, 2 or 3;

or a stereoisomer, tautomer, or pharmaceutically acceptable salt thereof.

8. The compound according to claim 7, wherein $R^2$ is ($C_6$)aryl or 5- to 6-membered heteroaryl, said heteroaryl containing 1-4 heteroatoms selected from N, and O, wherein both the aryl and heteroaryl may be optionally substituted with one or more $R^4$;

$R^4$ is fluoro, chloro, $CF_3$, —$OCF_3$, —CN, —$NO_2$, or a 5- to 6-membered heteroaryl containing 1-4 heteroatoms selected from N, O, and S, optionally substituted with one or more $R^5$; and $R^5$ is halogen, —OH, —$CF_3$, —$OCF_2$, —$OCF_3$, —CN, —($C_1$-$C_6$)alkyl, or —($C_1$-$C_6$)alkyloxy;

or a stereoisomer, tautomer, or pharmaceutically acceptable salt thereof.

9. The compound according to claim 8, wherein $R^1$ is ($C_6$)aryl or 5- to 6-membered heteroaryl, said heteroaryl containing 1-4 heteroatoms selected from N, O, and S, wherein aryl and heteroaryl may be optionally substituted with one or more $R^3$;

$R^2$ is phenyl, pyridyl, pyrimidinyl, pyridazinyl, or pyrazinyl, substituted with one or more $R^4$;

$R^3$ is independently chosen from halogen, —OH, —CN, —$CF_3$, —$OCHF_2$, —$OCF_3$, —($C_1$-$C_6$)alkyl, —($C_1$-$C_6$)-alkyloxy, —$CONR^9R^{10}$, —O(C=O)$NR^9R^{10}$, —($C_1$-$C_6$)-alkyl$CONR^9R^{10}$, —($C_6$-$C_{10}$)aryl, a 5- to 6-membered heteroaryl, which contains 1-4 heteroatoms selected from N, O, and S; and a 5- to 7-membered heterocyclyl, which contains 1-4 heteroatoms selected from N, O, and S; wherein any alkyl, aryl, heteroaryl, and heterocyclyl may be optionally substituted with one or more substituents selected from the group consisting of halo, —OH, cyano, —$CF_3$, —$OCF_3$, —$OCF_2$, ($C_1$-$C_6$)-alkyl, ($C_1$-$C_6$)-alkyloxy, —$CONR^9R^{10}$ and —O(C=O)$NR^9R^{10}$;

$R^4$ is fluoro, chloro, $CF_3$, —$OCF_2$, —$OCF_3$, —CN or —$NO_2$; or $R^4$ is tetrazole, oxadiazole, oxazole, pyrazole or isoxazole, optionally substituted with one or more $R^5$;

$R^5$ is halogen, —OH, —$CF_3$, —$OCF_2$, —$OCF_3$, —CN, methyl, ethyl, cyclopropyl, methoxy, ethoxy or cyclopropyloxy;

or a stereoisomer, tautomer, or pharmaceutically acceptable salt thereof.

10. A pharmaceutical composition comprising one or more compounds according to claim 1 and optionally a pharmaceutically acceptable carrier.

* * * * *